US012365895B2

United States Patent
Elmer et al.

(10) Patent No.: US 12,365,895 B2
(45) Date of Patent: Jul. 22, 2025

(54) VARIANT RNAI AGAINST ALPHA-SYNUCLEIN

(71) Applicant: Genzyme Corporation, Cambridge, MA (US)

(72) Inventors: Bradford Elmer, Bridgewater, NJ (US); Brenda Richards, Bridgewater, NJ (US); Martine Latta-Mahieu, Paris (FR); Maria Carmen Obinu, Paris (FR); Véronique Taupin, Paris (FR); Véronique Blanchard, Paris (FR)

(73) Assignee: Genzyme Corporation, Cambridge, MA (US)

( * ) Notice: Subject to any disclaimer, the term of this patent is extended or adjusted under 35 U.S.C. 154(b) by 1140 days.

(21) Appl. No.: 17/265,489

(22) PCT Filed: Aug. 2, 2019

(86) PCT No.: PCT/US2019/044924
§ 371 (c)(1),
(2) Date: Feb. 2, 2021

(87) PCT Pub. No.: WO2020/028816
PCT Pub. Date: Feb. 6, 2020

(65) Prior Publication Data
US 2021/0309999 A1    Oct. 7, 2021

Related U.S. Application Data

(60) Provisional application No. 62/714,616, filed on Aug. 3, 2018.

(51) Int. Cl.
*C12N 15/113* (2010.01)
*C12N 15/86* (2006.01)

(52) U.S. Cl.
CPC ............ *C12N 15/113* (2013.01); *C12N 15/86* (2013.01); *C12N 2310/14* (2013.01); *C12N 2320/32* (2013.01); *C12N 2750/14143* (2013.01); *C12N 2830/38* (2013.01); *C12N 2830/42* (2013.01); *C12N 2830/50* (2013.01)

(58) Field of Classification Search
CPC .. C12N 15/113; C12N 15/86; C12N 2310/14; C12N 2320/32; C12N 2750/14143
See application file for complete search history.

(56) References Cited

U.S. PATENT DOCUMENTS

| | | | |
|---|---|---|---|
| 8,283,151 B2 | 10/2012 | Schmidt | |
| 10,450,563 B2 | 10/2019 | Stanek | |
| 2005/0137155 A1 | 6/2005 | Mcswiggen | |
| 2012/0066783 A1 | 3/2012 | Kay | |
| 2012/0164106 A1 | 6/2012 | Schaffer | |
| 2013/0323226 A1 | 12/2013 | Wilson | |
| 2018/0073022 A1* | 3/2018 | Freier | A61P 25/16 |
| 2023/0414710 A1 | 12/2023 | Miller | |

FOREIGN PATENT DOCUMENTS

| | | | |
|---|---|---|---|
| CN | 107438671 A | 12/2017 | |
| JP | 2014501507 A | 1/2014 | |
| JP | 2018506304 A | 3/2018 | |
| RU | 2014138989 A | 4/2016 | |
| TW | 201704470 A | 2/2017 | |
| WO | 2003042397 A2 | 5/2003 | |
| WO | 2003042397 A3 | 2/2004 | |
| WO | 2008150897 A2 | 12/2008 | |
| WO | 2010029303 A1 | 3/2010 | |
| WO | WO-2012027713 A2 * | 3/2012 | ........... C12N 15/113 |
| WO | 2012068405 A2 | 5/2012 | |
| WO | 2015168666 A2 | 11/2015 | |
| WO | 2016130589 A2 | 8/2016 | |
| WO | 2020028816 A1 | 2/2020 | |

OTHER PUBLICATIONS

Bofill-De Ros, Xavier, and Shuo Gu. "Guidelines for the optimal design of miRNA-based shRNAs." Methods 103 (2016): 157-166. (Year: 2016).*
Terasawa, Kazuya, Kazuharu Shimizu, and Gozoh Tsujimoto. "Synthetic pre-miRNA-based shRNA as potent RNAi triggers." Journal of nucleic acids 2011 (2011). (Year: 2011).*
GenBankSNCA (Accession NM_001146055, *Homo sapiens* synuclein alpha (SNCA), transcript variant 3, mRNA, https://www.ncbi.nlm.nih.gov/nuccore/225690603?sat=46&satkey=73571735, retrieved Dec. 12, 2024, publibly available Jun. 14, 2017, pp. 1/1-1/5) (Year: 2017).*
Alagia, Adele, and Ramon Eritja. "siRNA and RNAi optimization." Wiley Interdisciplinary Reviews: RNA 7.3 (2016): 316-329. (Year: 2016).*
Alba, R. et al. (Oct. 2005). "Gutless Adenovirus: Last-Generation Adenovirus for Gene Therapy," Gene Ther. 12 (Suppl 1):S18-27.
Alvarez-Fischer, D. et al. (Mar. 2008). "Characterization Of The Striatal 6-OHDA Model Of Parkinson's Disease In Wild Type And Alpha-Synuclein-Deleted Mice," Experimental Neurology 210(1):182-193.
Baek, S.T. et al. (Jun. 18, 2014). "Off-Target Effect Of Doublecortin Family Shrna On Neuronal Migration Associated With Endogenous Microrna Dysregulation," Neuron 82(6):1255-1262.
Boudreau, R.L. et al. (Jan. 2013, e-pub. Aug. 31, 2012). "siSPOTR: A Tool for Designing Highly Specific and Potent Simnas for Human and Mouse," Nucleic Acids Res. 41(1):e9, 12 pages.

(Continued)

*Primary Examiner* — Ekaterina Poliakova-Georgantas
*Assistant Examiner* — John Charles McKillop
(74) *Attorney, Agent, or Firm* — MORRISON & FOERSTER LLP

(57) ABSTRACT

Provided herein are RNAi molecules for treating neurodegenerative synucleinopathies. In some embodiments, the RNAi molecules target expression of alpha-synuclein (SNCA). Further provided herein are expression constructs, vectors (e.g. rAAV), cells, viral particles, and pharmaceutical compositions containing the RNAi. Yet further provided herein are methods and kits related to the use of the RNAi, for example, to treat neurodegenerative synucleinopathies including Parkinson's disease, multiple system atrophy, and dementia with Lewy bodies.

12 Claims, 11 Drawing Sheets

Specification includes a Sequence Listing.

(56) References Cited

OTHER PUBLICATIONS

Cole, N.B. et al. (Mar. 11, 2005). "Metal-Catalyzed Oxidation Of A-Synuclein: Helping To Define The Relationship Between Oligomers, Protofibrils, And Filaments," Journal Of Biological Chemistry 280(10):9678-9690.

Dauer, W. et al. (Oct. 29, 2002). "Resistance Of Alpha-Synuclein Null Mice To The Parkinsonian Neurotoxin MPTP," Proceedings of the National Academy of Sciences of the United States of America 99 (22):14524-14529.

Drolet, R.E. et al. (Sep. 2004). "Mice Lacking Alpha-Synuclein Have An Attenuated Loss Of Striatal Dopamine Following Prolonged Chronic MPTP Administration," Neuroloxicology 25(5):761-769.

Finch, P.W. et al. (Dec. 1997). "Altered Expression Of Keratinocyte Growth Factor And Its Receptor In Psoriasis," The American Journal Of Pathology 151(6):1619, 10 pages.

International Preliminary Report on Patentability, mailed Nov. 13, 2019, filed Aug. 2, 2019 for App. No. PCT/US2019/044924, 7 pages.

International Search Report and Written Opinion of the International Searching Authority, mailed Nov. 13, 2019, filed Aug. 2, 2019 for App. No. PCT/US2019/044924, 10 pages.

Javed, H. et al. (Apr. 2016). "Development of Nonviral Vectors Targeting the Brain as a Therapeutic Approach For Parkinson's Disease and Other Brain Disorders," Molecular Therapy: The Journal Of The American Society Of Gene Therapy 24(4):746-758.

Klivenyi, P. et al. (Mar. 1, 2006). "Mice Lacking Alpha-Synuclein Are Resistant To Mitochondrial Toxins," Neurobiology Of Disease 21(3):541-548.

Lagos-Quintana, M. et al. (Apr. 30, 2002). "Identification of tissue-specific MicroRNAs from Mouse," Curr. Biol. 12:735-739.

Lim, Y. et al. (Jul. 6, 2011). "α-Syn Suppression Reverses Synaptic And Memory Defects In A Mouse Model Of Dementia With Lewy Bodies," Journal Of Neuroscience 31(27):10076-10087.

Mittal, S. et al. (Sep. 1, 2017, e-pub Sep. 1, 2018). "β2-Adrenoreceptor Is A Regulator Of The A-Synuclein Gene Driving Risk Of Parkinson's Disease," Science 357(6354):891-898.

Piccioli, P. et al. (Aug. 1995). "Neuroantibodies: Ectopic Expression of a Recombinant Anti-Substance P Antibody in the Central Nervous System of Transgenic Mice," Neuron 15:373-384.

Schildknecht, S. et al. (2013). "Generation Of Genetically-Modified Human Differentiated Cells For Toxicological Tests And The Study Of Neurodegenerative Diseases," Altex 30(4):427-444.

Terasawa, K. et al. (2011, e-pub Jul. 12, 2011). "Synthetic Pre-miRNA-Based shRNA as Potent RNAi Triggers", Journal of Nucleic Acids 2011:131579, 6 pages.

Ubhi, K. et al. (Apr. 21, 2010, e-pub Mar. 8, 2011). "Alpha-Synuclein Deficient Mice Are Resistant To Toxin-Induced Multiple System Atrophy," Neuroreport 21(6):457-462.

Sapru, M.K. et al. (2006, e-pub. Jan. 7, 2006). "Silencing Of Human Alpha-Synuclein In Vitro And In Rat Brain Using Lentiviral-Mediated RNAi," Experimental Neurology 198(2):382-390.

\* cited by examiner

FIG. 1A
FIG. 1B
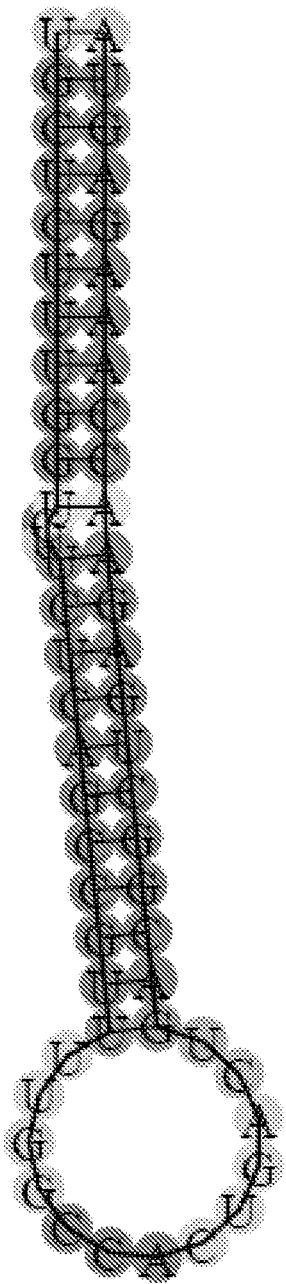
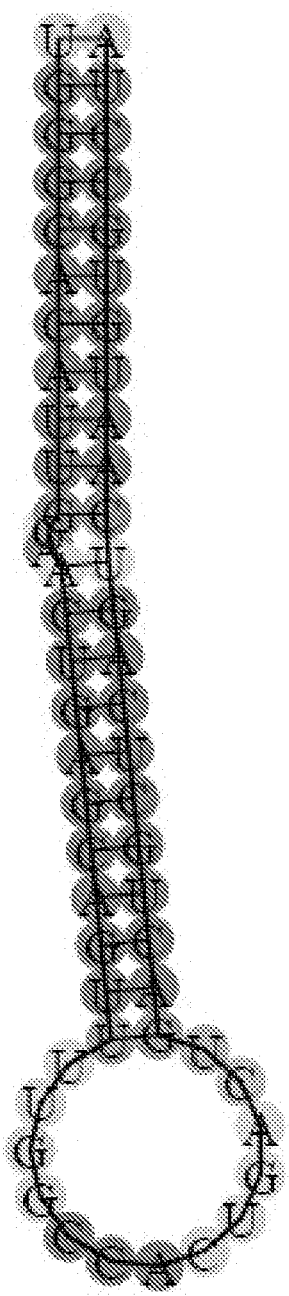

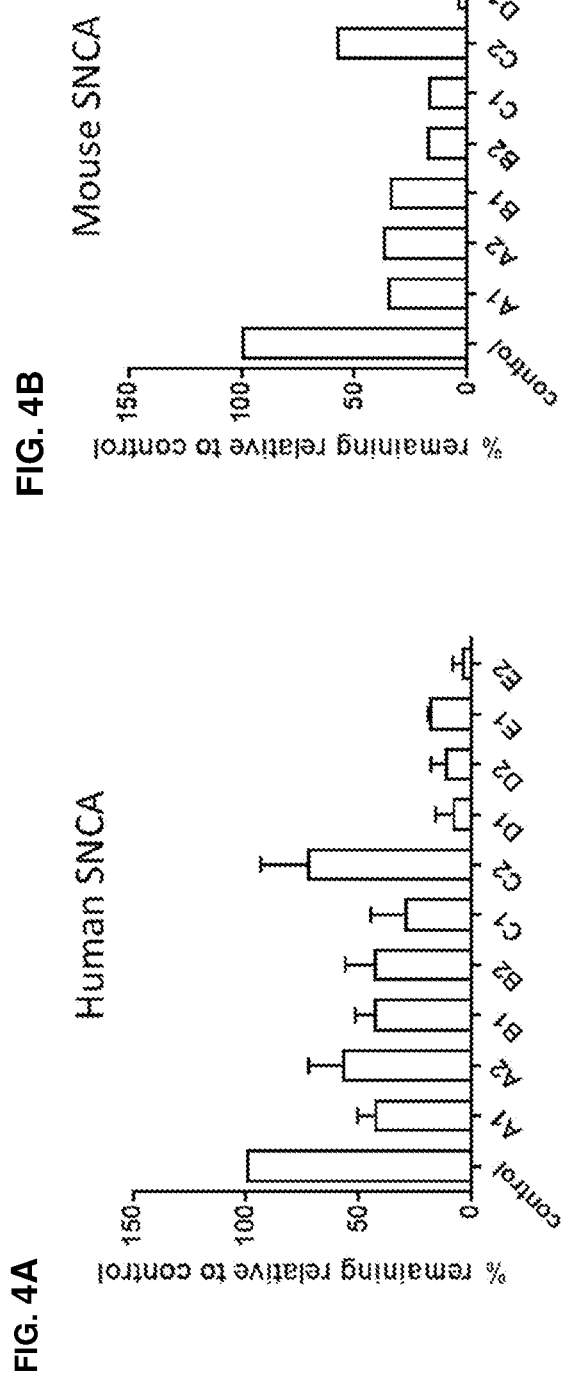
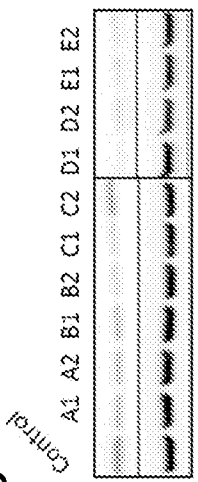
FIG. 4A
FIG. 4B
FIG. 4C
FIG. 4D

VARIANT RNAI AGAINST ALPHA-SYNUCLEIN

CROSS-REFERENCE TO RELATED APPLICATIONS

This application is a National Phase application under 35 U.S.C. § 371 of International Application No. PCT/US2019/044924, filed Aug. 2, 2019, which claims the priority benefit of U.S. Provisional Application No. 62/714,616, filed Aug. 3, 2018, the disclosure of each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792016500SEQLIST.TXT, date recorded: Feb. 2, 2021, size: 18,694 bytes).

FIELD OF THE INVENTION

The present disclosure relates to variant RNAi molecules. In some aspects, the disclosure relates to variant RNAi against alpha-synuclein.

BACKGROUND

Long-term neuroprotective therapy is of considerable interest for the treatment of neurodegenerative synucleinopathies like Parkinson's disease or multiple system atrophy (MSA). RNA interference (RNAi) is a mechanism whereby target mRNAs are reduced by introducing RNA (siRNA) that is complementary to the target. The siRNA sequence can also be inserted into an artificial miRNA scaffold ("shmiRNA") which allows for constitutive, polymerase II-based expression while also eliminating the neuronal toxicity associated with the introduction of siRNA or shRNA in the brain (1).

A hurdle to the clinical development of RNAi is the potential for off-target silencing where the seed region of the RNAi (typically nucleotides 1-7 or 1-8) pairs with sequences in non-target mRNAs in the 3' untranslated region (UTR) leading to transcript destabilization. Attempts to reduce off-target silencing include the use of algorithms to identify candidate seed sequences with high specificity for the target mRNA with minimal off-target potential (Boudreau R L et al., (2012) *Nucl. Acids Res.* 41 (1): e9) and placing an internal bulge in the guide region of the RNAi (Terasawa et al., (2011) *Journal of nucleic acids* 2011:131579).

Multiple lines of evidence demonstrate that increased levels of alpha-synuclein (SNCA) are neurotoxic, while reduction is neuroprotective (2-9). Hence, therapeutic strategies that reduce SNCA levels could potentially halt progression and alleviate symptoms of neurodegenerative diseases. There remains a need for such a therapeutic strategy utilizing RNAi mechanism.

This present application meets such a need by providing variant RNAi molecules against SNCA and methods for using thereof in the treatment and prevention of neurodegenerative diseases. The present application also provides methods for screening or identifying RNAi molecules against SNCA and construct for preparing these RNAi molecules.

BRIEF SUMMARY

In some aspects, the invention provides an RNAi comprising a first strand and a second strand, wherein a) the first strand and the second strand form a duplex; b) the first strand comprises a guide region, wherein the guide region comprises a nucleic acid having at least about 90% identity to the sequence 5'-UGCUCUUUGGUCUUCUCAGCC-3' (SEQ ID NO:24) or at least about 90% identity to the sequence 5'-UGGGCACAUUGGAACUGAGCA-3' (SEQ ID NO: 8); and c) the second strand comprises a non-guide region. In some embodiments, the guide region comprises the nucleic acid sequence 5'-UGCUCUUUGGUCUUCUCAGCC-3' (SEQ ID NO: 24) and the non-guide region comprises the sequence 5'-GGCUGAGAACCAAAGAGUA-3' (SEQ ID NO:53). In some embodiments, the first strand comprises a nucleic acid sequence having about 90% identity to SEQ ID NO:24 or about 90% identity to SEQ ID NO:53. In some embodiments, the guide region comprises the nucleic acid sequence 5'-UGGGCACAUUGGAACUGAGCA-3' (SEQ ID NO:8) and the non-guide region comprises the sequence 5'-UGCUCAGUCAAUGUGCCUA-3' (SEQ ID NO:37). In some embodiments, the second strand comprises a nucleic acid sequence having about 90% identity to SEQ ID NO:37 or about 90% identity to SEQ ID NO:37. In some embodiments, the first strand and the second strand are linked by means of a RNA linker capable of forming a loop structure. In some embodiments, the RNA linker comprises from 4 to 50 nucleotides. In some embodiments, the loop structure comprises 4 to 20 nucleotides. In some embodiments, the RNAi comprises 5' to 3' the second strand, the RNA linker, and the first strand. In some embodiments, the RNAi comprises 5' to 3' the first strand, the RNA linker, and the second strand. In some embodiments, the RNAi comprises the nucleic acid sequence of SEQ ID NO:61 or SEQ ID NO: 63. In some embodiments, the RNAi comprises a nucleotide sequence about 90% identical to the nucleotide sequence of SEQ ID NO: 61 or SEQ ID NO:63. In some embodiments, the RNAi is a small inhibitory RNA (siRNA), a microRNA (miRNA), or a small hairpin RNA (shRNA).

In some embodiments of the above aspect and embodiments the RNAi targets RNA encoding a polypeptide associated with a neurodegenerative synucleinopathy. In some embodiments, the polypeptide is alpha-synuclein (SNCA). In some embodiments, the alpha synuclein is human alpha-synuclein. In some embodiments, the neurodegenerative synucleinopathy is Parkinson's disease (PD), multiple system atropy (MSA), or dementia with Lewy bodies (DLB).

In some embodiments of the above aspect and embodiments, the invention provides an expression construct comprising nucleic acid encoding the RNAi described herein. In some embodiments, the nucleic acid encoding the RNAi comprises a miRNA scaffold. In some embodiments, the nucleic acid encoding the RNAi is operably linked to a promoter. In some embodiments, the promoter is selected from a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a 13-actin promoter. In some embodiments, the expression construct further comprises an intron. In some embodiments, the intron is a CBA intron or an hEF1alpha intron. In some embodiments, the intron is a chimeric intron. In some embodiments, the expression vector is a self-complementary vector and the intron is a delta chimeric intron. In some embodiments, the expression construct further comprises a polyadenylation signal. In some embodiments, the polyadenylation signal is a bovine growth hormone polyadenylation signal, an SV40 polyadenylation signal, or a HSV TK polyadenylation signal.

In some embodiments, the invention provides a vector comprising any of the expression constructs described herein. In some embodiments, the vector is a recombinant adeno-associated virus (rAAV) vector. In some embodiments, the expression construct is flanked by one or more AAV inverted terminal repeat (ITR) sequences. In some embodiments, the expression construct is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the vector further comprises a stuffer nucleic acid. In some embodiments, the stuffer nucleic acid is located upstream or downstream of the nucleic acid encoding the RNAi. In some embodiments, the vector is a self-complementary rAAV vector. In some embodiments, the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments, the invention provides a cell comprising any of the rAAV vectors as described herein.

In some embodiments, the invention provides a recombinant AAV particle comprising any of the rAAV vectors as described herein. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, AAV2-HBKO, AAVDJ8, AAVPHP.B, AAVPHP.eB, AAVBR1, AAVHSC15, AAVHSC17, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In some embodiments, the ITR and the capsid of the rAAV viral particle are derived from different AAV serotypes. In some embodiments, the ITR is derived from AAV2 and the capsid of the rAAV particle is derived from AAV1.

In some embodiments, the invention provides a composition comprising any of the rAAV particles described herein. In some embodiments, the composition further comprises a pharmaceutically acceptable carrier.

In some embodiments, the invention provides a kit comprising any of the RNAi described herein. In some embodiments, the invention provides a kit comprising any of the AAV particles described herein. In some embodiments, the invention provides a kit comprising any of the compositions described herein. In some embodiments, the kit further comprises instructions for use.

In some aspects, the invention provides methods for treating a neurodegenerative synucleinopathy in a mammal comprising administering to the mammal an RNAi comprising a first strand comprising a first nucleic acid having at least about 90% identity to the sequence 5'-UGCUCUUUG-GUCUUCUCAGCC-3' (SEQ ID NO:24) or a first strand comprising a first nucleic acid having at least about 90% identity to the sequence 5'-UGGGCACAUUG-GAACUGAGCA-3' (SEQ ID NO:8), and a second strand comprising a second nucleic acid. In some embodiments, the second nucleic acid comprises nucleic acid having at least about 90% identity to the sequence the sequence 5'-GGCUGAGAACCAAAGAGUA-3' (SEQ ID NO:53) or nucleic acid having at least about 90% identity to the sequence 5'-E1passenger-3' (SEQ ID NO:37).

In some aspects, the invention provides methods for treating a neurodegenerative synucleinopathy in a mammal comprising administering to the mammal an RNAi comprising a first strand comprising a first nucleic acid having at least about 90% identity to the sequence 5'-UGCUCUUUG-GUCUUCUCAGCC-3' (SEQ ID NO:24) and a second strand comprising a second nucleic acid having at least about 90% identity to the sequence 5'-GGCUGAGAAC-CAAAGAGUA-3' (SEQ ID NO:53) or a first strand comprising a first nucleic acid having at least about 90% identity to the sequence 5'-UGGGCACAUUGGAACUGAGCA-3' (SEQ ID NO:8) and a second strand comprising a second nucleic acid having at least about 90% identity to the sequence 5'-UGCUCAGUCAAUGUGCCUA-3' (SEQ ID NO:37).

In some aspects, the invention provides methods for inhibiting the expression of alpha-synuclein in a mammal with a neurodegenerative disease comprising administering to the mammal an RNAi comprising a first strand comprising a first nucleic acid having at least about 90% identity to the sequence 5'-UGCUCUUUGGUCUUCUCAGCC-3' (SEQ ID NO:24) or a first strand comprising a nucleic acid having at least about 90% identity to the sequence 5'-UGGGCACAUUGGAACUGAGCA-3' (SEQ ID NO:8), and a second strand comprising a second nucleic acid. In some embodiments, the second nucleic acid comprises nucleic acid having at least about 90% identity to the sequence 5'-GGCUGAGAACCAAAGAGUA-3' (SEQ ID NO: 53) or nucleic acid having at least about 90% identity to the sequence 5'-UGCUCAGUCAAUGUGCCUA-3' (SEQ ID NO:37).

In some aspects, the invention provides methods for inhibiting the expression of alpha-synuclein in a mammal with a neurodegenerative disease comprising administering to the mammal an RNAi comprising a first strand comprising a first nucleic acid having at least about 90% identity to the sequence 5'-UGCUCUUUGGUCUUCUCAGCC-3' (SEQ ID NO:24) and a second strand comprising a second nucleic acid having at least about 90% identity to the sequence 5'-GGCUGAGAACCAAAGAGUA-3' (SEQ ID NO:53) or a first strand comprising a first nucleic acid having at least about 90% identity to the sequence 5'-UGGGCACAUUGGAACUGAGCA-3' (SEQ ID NO:8) and a second strand comprising a second nucleic acid having at least about 90% identity to the sequence 5'-UGCUCA-GUCAAUGUGCCUA-3' (SEQ ID NO:37).

In some embodiments of the above methods, the first strand comprises the nucleic acid sequence having the sequence of SEQ ID NO:24 or nucleic acid having the sequence of SEQ ID NO:8. In some embodiments, the second strand comprises the nucleic acid having the sequence of SEQ ID NO:53 or the nucleic acid having the sequence of SEQ ID NO:37. In some embodiments, the first strand and the second strand are linked by means of a RNA linker capable of forming a loop structure. In some embodiments, the RNA linker comprises from 4 to 50 nucleotides. In some embodiments, the loop structure comprises 4 to 20 nucleotides. In some embodiments, the RNAi comprises 5' to 3' the second strand, the RNA linker, and the first strand. In some embodiments, the RNAi comprises 5' to 3' the first strand, the RNA linker, and the second strand. In some embodiments, the RNAi comprises the nucleic acid sequence of SEQ ID NO: 61 or SEQ ID NO:63. In some embodiments, the RNAi comprises a nucleotide sequence about 90% identical to the nucleotide sequence of SEQ ID NO: 61 or SEQ ID NO:63. In some embodiments, the RNAi is a small inhibitory RNA (siRNA), a microRNA (miRNA), or a small hairpin RNA (shRNA).

In some embodiments of the above methods the RNAi targets RNA encoding a polypeptide associated with a neurodegenerative synucleinopathy. In some embodiments, the polypeptide is alpha-synuclein (SNCA). In some embodiments, the alpha synuclein is human alpha-synuclein. In some embodiments, the neurodegenerative synucleinopathy is Parkinson's disease (PD), multiple system atropy (MSA), or dementia with Lewy bodies (DLB).

In some embodiments of the above methods, the invention provides an expression construct comprising nucleic acid encoding the RNAi described herein. In some embodiments, the nucleic acid encoding the RNAi comprises a miRNA scaffold. In some embodiments, the nucleic acid encoding the RNAi is operably linked to a promoter. In some embodiments, the promoter is selected from a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a 13-actin promoter. In some embodiments, the expression construct further comprises an intron. In some embodiments, the intron is a CBA intron or an hEF1alpha intron. In some embodiments, the intron is a chimeric intron. In some embodiments, the expression vector is a self-complementary vector and the intron is a delta chimeric intron. In some embodiments, the expression construct further comprises a polyadenylation signal. In some embodiments, the polyadenylation signal is a bovine growth hormone polyadenylation signal, an SV40 polyadenylation signal, or a HSV TK polyadenylation signal.

In some embodiments of the above methods, the invention provides a vector comprising any of the expression constructs described herein. In some embodiments, the vector is a recombinant adeno-associated virus (rAAV) vector. In some embodiments, the expression construct is flanked by one or more AAV inverted terminal repeat (ITR) sequences. In some embodiments, the expression construct is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the vector further comprises a stuffer nucleic acid. In some embodiments, the stuffer nucleic acid is located upstream or downstream of the nucleic acid encoding the RNAi. In some embodiments, the vector is a self-complementary rAAV vector. In some embodiments, the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments of the above methods, the invention provides a recombinant AAV particle comprising any of the rAAV vectors as described herein. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, AAV2-HBKO, AAVDJ8, AAVPHP.B, AAVPHP.eB, AAVBR1, AAVHSC15, AAVHSC17, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In some embodiments, the ITR and the capsid of the rAAV viral particle are derived from different AAV serotypes. In some embodiments, the ITR is derived from AAV2 and the capsid of the rAAV particle is derived from AAV1. In some embodiments, the rAAV particle is in a composition. In some embodiments, the composition further comprises a pharmaceutically acceptable carrier.

All references cited herein, including patent applications and publications, are incorporated by reference in their entirety.

BRIEF DESCRIPTION OF THE DRAWINGS

FIG. 1A shows the structure if D1 shmiRNA (SEQ ID NO:61) and FIG. 1B shows the structure of E1 shmiRNA (SEQ ID NO:63).

FIGS. 4A-D show RNAi-mediated reduction of mouse or human alpha-synuclein protein in vitro. Diagrams of quantitative analysis of SNCA in whole cell extracts of HEK293T cells 72 hours post-transfection with plasmids encoding the indicated RNAi sequences in siRNA format and human SNCA cDNA (FIG. 4A) or mouse SNCA cDNA (FIG. 4B). SNCA protein levels were normalized to beta tubulin, and normalized to control (non-targeting control RNAi) to calculate percent knockdown as shown in the western blotting images for human SNCA (FIG. 4C) and mouse SNCA (FIG. 4D).

(FIG. 5A) Cell viability measured via Cell Titer Blue® assay 48 hours post-rotenone treatment and demonstrated significant neuroprotection by both D1 and E1 RNAi sequences (38% and 40% respectively), but not with the control RNAi sequence. % mean neuroprotection is calculated at % change from control.

(FIG. 5B) Reactive oxygen species measured as an additional readout of rotenone-induced toxicity.

DETAILED DESCRIPTION

Figure 2:
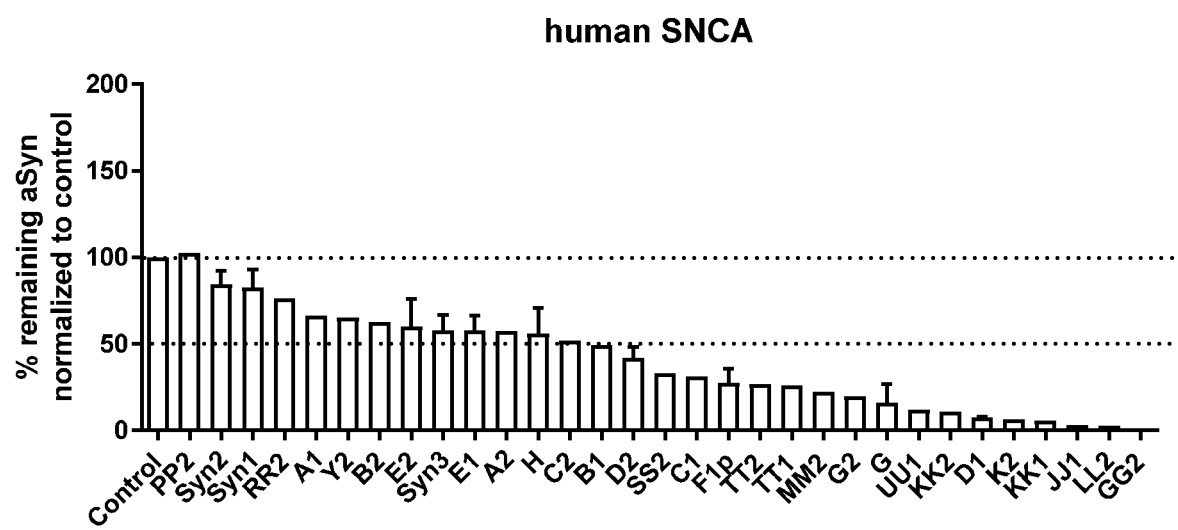
FIG. 2 shows RNAi-mediated reduction of human SNCA in vitro. Quantification of SNCA in whole cell extracts of HEK293T cells 72 hours post-transfection with plasmids encoding the indicated RNAi sequences in shmiRNA format and human SNCA cDNA. SNCA levels were normalized to GAPDH loading control, and normalized to control (non-targeting control RNAi) to calculate percent knockdown.

In some aspects, the disclosure provides RNAi for treating neurodegenerative synucleinopathies. In some embodiments, the neurodegenerative synucleinopathy is Parkinson's disease or multiple system atrophy (MSA). In some embodiments, the RNAi targets alpha-synuclein. In some embodiments, the RNAi reduces expression of alpha-synuclein. In some embodiments, the RNAi comprises a first strand comprising a first nucleic acid comprising the sequence 5'-UGCUCUUUGGUCUUCUCAGCC-3' (SEQ ID NO:24). In some embodiments, the RNAi comprises a first strand comprising a first nucleic acid comprising the sequence 5'-UGCUCUUUGGUCUUCUCAGCC-3' (SEQ ID NO:24) and a second strand comprising a second nucleic acid comprising the sequence 5'-GGCUGAGAAC-CAAAGAGUA-3' (SEQ ID NO: 53). In some embodiments, the RNAi comprises a first strand comprising a first nucleic acid comprising the sequence 5'-UGGGCA-CAUUGGAACUGAGCA-3' (SEQ ID NO:8). In some embodiments, the RNAi comprises a first strand comprising a first nucleic acid comprising the sequence 5'-UGGGCA-CAUUGGAACUGAGCA-3' (SEQ ID NO:8) and a second strand comprising a second nucleic acid comprising the sequence 5'-UGCUCAGUCAAUGUGCCUA-3' (SEQ ID NO:37). In some aspects, the disclosure provides expression constructs, vectors (e.g., recombinant AAV vectors), cells, viral particles (e.g., AAV particles), and pharmaceutical compositions comprising an RNAi of the present disclosure. In further aspects, the disclosure provides methods for treating neurodegenerative synucleinopathies, inhibiting the expression of SNCA, and inhibiting the accumulation of SNCA in a cell in a mammal comprising administering to the mammal a pharmaceutical composition comprising an RNAi of the present disclosure. In still further aspects, the disclosure provides for the use of a pharmaceutical composition comprising an RNAi of the present disclosure to treat neurodegenerative synucleinopathies (e.g., ameliorate the symptoms of neurodegenerative synucleinopathies), inhibit the expression of SNCA, or inhibit the accumulation of SNCA in a cell in a mammal with neurodegenerative synucleinopathies. In some embodiments, the synucleinopathy is Parkinson's disease, multiple system atropy or dementia with Lewy bodies.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); PCR 2: A Practical Approach (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate ($P-NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one and in some embodiments two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, and in embodiments two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV vector can be in any of a number of forms, including, but not limited to, plasmids, linear artificial chromosomes, complexed with lipids, encapsulated within liposomes, and encapsidated in a viral particle, particularly an AAV particle. A rAAV vector can be packaged into an AAV virus capsid to generate a "recombinant adeno-associated viral particle (rAAV particle)".

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as miRNA, siRNA, or shRNA.

"Chicken β-actin (CBA) promoter" refers to a polynucleotide sequence derived from a chicken β-actin gene (e.g., *Gallus gallus* beta actin, represented by GenBank Entrez Gene ID 396526). As used herein, "chicken β-actin promoter" may refer to a promoter containing a cytomegalovirus (CMV) early enhancer element, the promoter and first exon and intron of the chicken β-actin gene, and the splice acceptor of the rabbit beta-globin gene, such as the sequences described in Miyazaki, J. et al. (1989) *Gene* 79 (2): 269-77. As used herein, the term "CAG promoter" may be used interchangeably. As used herein, the term "CMV early enhancer/chicken beta actin (CAG) promoter" may be used interchangeably.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.,* 10:1031-1039; Veldwijk et al. (2002) *Mol. Ther.,* 6:272-278.

The term "vector genome (vg)" as used herein may refer to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques. For example, a recombinant AAV vector genome may include at least one ITR sequence flanking a promoter, a stuffer, a sequence of interest (e.g., an RNAi), and a polyadenylation sequence. A complete vector genome may include a complete set of the polynucleotide sequences of a vector. In some embodiments, the nucleic acid titer of a viral vector may be measured in terms of vg/mL. Methods suitable for measuring this titer are known in the art (e.g., quantitative PCR).

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting the expression of a gene may refer to any act leading to a blockade, reduction, elimination, or any other antagonism of expression of the gene, including reduction of mRNA abundance (e.g., silencing mRNA transcription), degradation of mRNA, inhibition of mRNA translation, and so forth. In some embodiments, inhibiting the expression of SNCA may refer a blockade, reduction, elimination, or any other antagonism of expression of SNCA, including reduction of SNCA mRNA abundance (e.g., silencing SNCA mRNA transcription), degradation of SNCA mRNA, inhibition of SNCA mRNA translation, and so forth. As another example, inhibiting the accumulation of a protein in a cell may refer to any act leading to a blockade, reduction, elimination, or other antagonism of expression of the protein, including reduction of mRNA abundance (e.g., silencing mRNA transcription), degradation of mRNA, inhibition of mRNA translation, degradation of the protein, and so forth. In some embodiments, inhibiting the accumulation of SNCA protein in a cell refers to a blockade, reduction, elimination, or other antagonism of expression of the SNCA protein in a cell, including reduction of SNCA mRNA abundance (e.g., silencing SNCA mRNA transcription), degradation of SNCA mRNA, inhibition of SNCA mRNA translation, degradation of the SNCA protein, and so forth The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in Mclaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.*, 144:113-124; or in Fisher et al. (1996) *J. Virol.*, 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

"AAV helper functions" refer to functions that allow AAV to be replicated and packaged by a host cell. AAV helper functions can be provided in any of a number of forms, including, but not limited to, helper virus or helper virus genes which aid in AAV replication and packaging. Other AAV helper functions are known in the art such as genotoxic agents.

A "helper virus" for AAV refers to a virus that allows AAV (which is a defective parvovirus) to be replicated and packaged by a host cell. A helper virus provides "helper functions" which allow for the replication of AAV. A number of such helper viruses have been identified, including adenoviruses, herpesviruses and, poxviruses such as vaccinia and baculovirus. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Examples of adenovirus helper functions for the replication of AAV include E1A functions, E1B functions, E2A functions, VA functions and E4orf6 functions. Baculoviruses available from depositories include *Autographa californica* nuclear polyhedrosis virus.

A preparation of rAAV is said to be "substantially free" of helper virus if the ratio of infectious AAV particles to infectious helper virus particles is at least about $10^2:1$; at least about $10_4:1$, at least about $10^6:1$; or at least about $10^8:1$ or more. In some embodiments, preparations are also free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A preferred alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this disclosure, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

As used herein, the term "neurodegenerative synucleinopathy" refers to neurodegenerative disorders characterized by fibrillary aggregates of alpha-synuclein protein in the cytoplasm of selective populations of neurons and glia in both the central and peripheral nervous systems. Examples include, but are not limited to, Parkinson's disease (PD), multiple system atrophy (MSA-P and MSA-C), dementia with Lewy bodies (DLB), pure autonomic failure (PAF), Lewy body variant of Alzheimer's disease (LBVAD), Lewy body dysphagia, and incidental Lewy body disease.

As used herein, an "RNAi" may refer to any RNA molecule that induces RNA interference in a cell. Examples of RNAi include without limitation small inhibitory RNAs (siRNAs), microRNAs (miRNAs), and small hairpin RNAs (shRNAs).

"miRNA scaffold" may refer to a polynucleotide containing (i) a double-stranded sequence targeting a gene of interest for knockdown by RNAi and (ii) additional sequences that form a stem-loop structure resembling that of endogenous miRNAs. A sequence targeting a gene of interest for RNAi (e.g., a short, ~20-nt sequence) may be ligated to sequences that create a miRNA-like stem-loop and a sequence that base pairs with the sequence of interest to form a duplex when the polynucleotide is assembled into the miRNA-like secondary structure. As described herein, this duplex may hybridize imperfectly, e.g., it may contain one or more unpaired or mispaired bases. Upon cleavage of this polynucleotide by Dicer, this duplex containing the sequence targeting a gene of interest may be unwound and incorporated into the RISC complex. A miRNA scaffold may refer to the miRNA itself or to a DNA polynucleotide encoding the miRNA. An example of a miRNA scaffold is the miR-155 sequence (Lagos-*Quintana*, M. et al. (2002) *Curr. Biol.* 12:735-9). Commercially available kits for cloning a sequence into a miRNA scaffold are known in the art (e.g., the Invitrogen™ BLOCK-iT™ Pol II miR RNAi expression vector kit from Life Technologies, Thermo Fisher Scientific; Waltham, MA).

As used herein, a "bulge" refers to a region of nucleic acid that is non-complementary to nucleic acid opposite it in a duplex nucleic acid. For example, a bulge may refer to a nucleic acid sequence that is noncomplementary to nucleic acid opposite in a duplex nucleic acid where the bulge is flanked by regions of nucleic acid that are complementary to nucleic acid opposite in a duplex nucleic acid. In some examples, the bulge may be any of 1, 2, 3, 4, 5, 6, 7, 8, 9, 10 or greater than 10 bases in length. In some examples, the bulge may be the result of mispairing (e.g., the opposite strand contains a base that is noncomplementary) or the bulge may be the result of nonpairing (e.g., the opposite strand comprises nucleic acid complementary to nucleic acid flanking the bulge but the opposite strand does not contain nucleic acid opposite the bulge).

As used herein, the term "sense" nucleic acid is a nucleic acid comprising a sequence that encodes all or a part of a transgene. In some examples, mRNA for a transgene is a sense nucleic acid.

As used herein, "antisense" nucleic acid is a sequence of nucleic acid that is complementary to a "sense" nucleic acid. For example, an antisense nucleic acid may be complementary to an mRNA encoding a transgene.

As used herein, the "guide region" of an RNAi is the strand of the RNAi that binds the target mRNA, typically on the basis of complementarity. The region of complementarity may encompass the all or a portion of the guide region. Typically, the region of complementarity includes at least the seed region. In many cases, the antisense region of an RNAi is the guide region.

As used herein, the "passenger region," or "non-guide region," used interchangeably herein, of an RNAi is the region of the RNAi that is complementary to the guide region. In many cases, the sense region of an RNAi is the passenger region.

As used herein, the "seed region" of an RNAi (e.g., miRNA) is a region of about 1-8 nucleotides in length of a microRNA. In some examples, the seed region and the 3'-UTR of its target mRNA may be a key determinant in RNAi recognition.

As used herein, "off-target gene silencing" refers to the pairing of a seed region of an RNAi with sequences in 3'-UTRs of unintended mRNAs and directs translational repression and destabilization of those transcripts (e.g., reduces expression of the unintended mRNAs).

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the disclosure described herein include "comprising," "consisting," and/or "consisting essentially of" aspects and embodiments.

III. RNAi

In some aspects, the disclosure provides improved RNAi. In some embodiments, the RNAi is a small inhibitory RNA (siRNA), a microRNA (miRNA), or a small hairpin RNA (shRNA). A small inhibitory or interfering RNA (siRNA) is known in the art as a double-stranded RNA molecule of approximately 19-25 (e.g., 19-23) base pairs in length that induces RNAi in a cell. In some embodiments, the siRNA sequence can also be inserted into an artificial miRNA scaffold ("shmiRNA"). A small hairpin RNA (shRNA) is known in the art as an RNA molecule comprising approximately 19-25 (e.g., 19-23) base pairs of double stranded RNA linked by a short loop (e.g., ~4-11 nucleotides) that induces RNAi in a cell.

A microRNA (miRNA) is known in the art as an RNA molecule that induces RNAi in a cell comprising a short (e.g., 19-25 base pairs) sequence of double-stranded RNA linked by a loop and containing one or more additional sequences of double-stranded RNA comprising one or more bulges (e.g., mispaired or unpaired base pairs). As used herein, the term "miRNA" encompasses endogenous miRNAs as well as exogenous or heterologous miRNAs. In some embodiments, "miRNA" may refer to a pri-miRNA or a pre-miRNA. During miRNA processing, a pri-miRNA transcript is produced. The pri-miRNA is processed by Drosha-DGCR8 to produce a pre-miRNA by excising one or more sequences to leave a pre-miRNA with a 5'flanking region, a guide strand, a loop region, a non-guide strand, and a 3'flanking region; or a 5'flanking region, a non-guide strand, a loop region, a guide strand, and a 3'flanking region. The pre-miRNA is then exported to the cytoplasm and processed by Dicer to yield a siRNA with a guide strand and a non-guide (or passenger) strand. The guide strand is then used by the RISC complex to catalyze gene silencing, e.g., by recognizing a target RNA sequence complementary to the guide strand. Further description of miRNAs may be found, e.g., in WO 2008/150897. The recognition of a target sequence by a miRNA is primarily determined by pairing between the target and the miRNA seed sequence, e.g., nucleotides 1-8 (5' to 3') of the guide strand (see, e.g., Boudreau, R. L. et al. (2013) *Nucleic Acids Res.* 41: e9).

In the pri/pre-miRNA structure, the guide strand: non-guide strand interface in a duplex is formed in part through complementary base pairing (e.g., Watson-Crick base pairing). However, in some embodiments, this complementary base pairing does not extend through the entire duplex. In some embodiments, a bulge in the interface may exist at one or more nucleotide positions. As used herein, the term "bulge" may refer to a region of nucleic acid that is non-complementary to the nucleic acid opposite it in a duplex. In some embodiments, the bulge is formed when the regions of complementary nucleic acids bind to each other, whereas the regions of central non-complementary region do not bind. In some embodiments, the bulge is formed when the two strands of nucleic acid positioned between the two complementary regions are of different lengths. As described below, a bulge May 1 or more nucleotides. In some embodiments, the miRNA comprises an internal bulge generated by deleting 2 based from the passenger strand of the miRNA-bases 9-10, counting from the start of the passenger strand.

In another aspect, the RNAi described in this disclosure is inhibitory against alpha-synuclein (SNCA). In some embodiments, the SNCA is mouse SNCA. In some embodiments, the SNCA is human SNCA. In some embodiments, the RNAi targets RNA encoding SNCA. In some embodiments, the RNAi inhibits the expression of SNCA in a subject. In some embodiments, the RNAi inhibits the accumulation of SNCA in a subject. In some embodiments, the subject is a mammal. In some embodiments, the mammal is a human.

The safety of RNAi-based therapies can be hampered by the ability of small inhibitory RNAs (siRNAs) to bind to unintended mRNAs and reduce their expression, an effect known as off-target gene silencing. Off-targeting primarily occurs when the seed region (nucleotides 2-8 of the small RNA) pairs with sequences in 3'-UTRs of unintended mRNAs and directs translational repression and destabilization of those transcripts. Reduced off-targeting RNAi may be designed by substituting bases within the guide and nonguide sequences; e.g., by creating CpG motifs. Potential substitutions that may result in a significantly lower off-target score can be evaluated using the SiSPOTR algorithm, a specificity-focused siRNA design algorithm which identifies candidate sequences with minimal off-targeting potentials and potent silencing capacities (Boudreau et al, *Nucleic Acids Res.* 2013 January; 41 (1) e9. A reduced SiSPOTR score predicts sequences that have a lower number of potential human off targets compared parent RNAi molecules. In some embodiments of the disclosure, the RNAi is improved to reduce off-target gene silencing. In some embodiments, the RNAi comprises one or more CpG motifs. In some embodiments, the RNAi comprises one or more CpG motifs in a seed region.

In some embodiments, the first strand and the second strand are linked by means of a RNA (e.g., a RNA linker) capable of forming a loop structure. As is commonly known in the art, an RNA loop structure (e.g., a stem-loop or hairpin) is formed when an RNA molecule comprises two sequences of RNA that basepair together separated by a sequence of RNA that does not base pair together. For example, a loop structure may form in the RNA molecule A-B-C if sequences A and C are complementary or partially complementary such that they base pair together, but the bases in sequence B do not base pair together. In some embodiments, the loop sequence is 5'-GTTTTGGC-CACTGACTGAC-3' (SEQ ID NO:59) in DNA form or 5'-GUUUUGGCCACUGACUGAC-3' (SEQ ID NO:60) in RNA form.

In some embodiments, the RNA capable of forming a loop structure comprises from 4 to 50 nucleotides. In certain embodiments, the RNA capable of forming a loop structure comprises 13 nucleotides. In some embodiments, the number of nucleotides in the RNA capable of forming a loop is from 4 to 50 nucleotides or any integer therebetween. In some embodiments, from 0-50% of the loop can be complementary to another portion of the loop. As used herein, the term "loop structure" is a sequence that joins two complementary strands of nucleic acid. In some embodiments, 1-3 nucleotides of the loop structure are contiguous to the complementary strands of nucleic acid and may be complementary to 1-3 nucleotides of the distal portion of the loop structure. For example, the three nucleotides at the 5' end of the loop structure may be complementary to the three nucleotides at the 3' end of the loop structure.

In some embodiments, nucleic acid encoding an RNAi of the present disclosure comprises a heterologous miRNA scaffold. In some embodiments, use of a heterologous miRNA scaffold is used to modulate miRNA expression; for example, to increase miRNA expression or to decrease miRNA expression. Any miRNA scaffold known in the art may be used. In some embodiments, the miRNA scaffold is derived from a miR-155 scaffold (see, e.g., Lagos-Quintana, M. et al. (2002) *Curr. Biol.* 12:735-9 and the Invitrogen™ BLOCK-iT™ Pol II miR RNAi expression vector kit from Life Technologies, Thermo Fisher Scientific; Waltham, MA).

In some embodiments, the RNAi is selected from Table 1.

In some embodiments, the first strand comprises a nucleic acid sequence having more than about any of 75%, 80%, 85%, 90%, 95%, 96%, 97%, 98% or 99% identity to any guide sequences. In some embodiments, the first strand comprises a nucleic acid sequence having more than about any of 75%, 80%, 85%, 90%, 95%, 96%, 97%, 98% or 99% identity to any guide sequences but maintains the CpG motif. In some embodiments, the second strand comprises a nucleic acid sequence having more than about any of 75%, 80%, 85%, 90%, 95%, 96%, 97%, 98% or 99% identity to the corresponding passenger sequence. In some embodiments, the second strand comprises a nucleic acid sequence having more than about any of 75%, 80%, 85%, 90%, 95%, 96%, 97%, 98% or 99% identity to the corresponding passenger sequence but maintains the CpG motif.

TABLE 1

| SEQ ID. | Guide Sequence (First Strand) | SEQ ID. | Passenger Sequence (Second Strand) | Species Homology | Human off-target prediction |
|---|---|---|---|---|---|
| 1 | CAUCGGAACUGAGCACUUGUA | 30 | UACAAGUGCAGUUCCGAUG | hs, mq, ms | 562 |
| 2 | AGGUUCGUAGUCUUGAUACCCU | 31 | AAGGUUAGAAUGGCGGUUAA | hs | 518 |
| 3 | uUAACCGCCACUUUCUAACCUU | 32 | AAGGUUAGAAUGGCGGUUAA | hs | 530 |
| 4 | ACGUUGGAACUGAGCACUUGU | 33 | ACAAGUGCAGUUCCAACGU | hs, mq, ms | 882 |
| 5 | uUCCAACAUUUGUCACUUGCU | 34 | AGCAAGUGAAAUGUUGGAA | hs, mq, ms | 4016 |
| 6 | UCGUCCAACAUUUGUCACUUG | 35 | CAAGUGACAUGUUGGACGA | hs, mq, ms | 1190 |
| 7 | UGGGCGCAUUGGAACUGAGCA | 36 | UGCUCAGUCAAUGCGCCUA | hs, mq, ms | 1662 |
| 8 | UGGGCACAUUGGAACUGAGCA | 37 | UGCUCAGUCAAUGUGCCUA | hs, mq, ms | 4335 |
| 9 | GUCGUCGAAUGGCCACUCCCA | 38 | UGGGAGUGCAUUCGACGAU | hs, mq | nd |
| 10 | GGUUCGUAGUCUUGAUACCCUU | 39 | AAGGGUAUCAACUACGAACC | hs | 564 |
| 11 | uAGCAGCAGCCACAACUCCCU | 40 | AGGGAGUUGGCUGCUGCUA | hs, mq, ms | 6390 |
| 12 | uUCGAACAUUUGUCACUUGCU | 41 | AGCAAGUGAAAUGUUCGAA | hs, mq, ms | 852 |
| 13 | uAGCCGCCACAACUCCCUCCU | 42 | AGGAGGGAUGUGGCGGCUA | hs, mq, ms | 1253 |
| 14 | UGCGCUUUGGUCUUCUCAGCC | 43 | GGCUGAGAACCAAAGCGUA | hs, mq, ms | 798 |
| 15 | uAGCCGCAGCCACAACUCCCU | 44 | AGGGAGUUGGCUGCGGCUA | hs, mq, ms | 1253 |
| 16 | uAGCAGCCACAACUCCCUCCU | 45 | AGGAGGGAUGUGGCUGCUA | hs, mq, ms | 6390 |
| 17 | UCGGCACAUUGGAACUGAGCA | 46 | UGCUCAGUCAAUGUGCCGA | hs, mq, ms | 1249 |
| 18 | AUGACGGGGCACAUUGGAACU | 47 | AGUUCCAAUGCCCCGUCAU | hs, mq, ms | 1071 |
| 19 | AUGACUGGGCACAUUGGAACU | 48 | AGUUCCAAUGCCCAGUCAU | hs, mq, ms | 4604 |
| 20 | UAAGUCGUAGUCACUUAGGUG | 49 | CACCUAAGACUACGACUUA | hs, mq, ms | 866 |
| 21 | CUCCGCAGCAGCCACAACUCC | 50 | GGAGUUGUCUGCUGCGGAG | hs, mq, ms | 995 |
| 22 | UCAUGACUGGGCACAUUGGAA | 51 | UUCCAAUGCCCAGUCAUGA | hs, mq, ms | 3588 |
| 23 | AAAUACGUGGUAGUCACUUAG | 52 | CUAAGUGAACCACGUAUUU | hs, mq, ms | 1152 |
| 24 | UGCUCUUUGGUCUUCUCAGCC | 53 | GGCUGAGAACCAAAGAGUA | hs, mq, ms | 4560 |
| 25 | AACGUUUGUCACUUGCUCUUU | 54 | AAAGAGCAUGACAAACGUU | hs, mq, ms | 1990 |
| 26 | AAAUAAGUGGUAGUCACUUAG | 55 | CUAAGUGAACCACUUAUUU | hs, mq, ms | 5638 |

TABLE 1-continued

| SEQ ID. | Guide Sequence (First Strand) | SEQ ID. | Passenger Sequence (Second Strand) | Species Homology | Human off-target prediction |
|---|---|---|---|---|---|
| 27 | UUAGAAAUAAGUGGUAGUCAC | 56 | GUGACUACCUUAUUUCUAA | hs, mq, ms | 7503 |
| 28 | AAUACGUGGUAGUCACUUAGG | 57 | CCUAAGUGUACCACGUAUU | hs, mq, ms | 1149 |
| 29 | ACUGCGCACAUUGGAACUGAG | 58 | CUCAGUUCAUGUGCGCAGU | hs, mq, ms | 1355 |

Legend: Sequences are from 5' to 3'. Small letters indicate mismatches with the target sense strand in order to decrease the stability of the processed duplex at the 5' end of the guide strand. Hs = human; mq = rhesus macaque, ms = mouse. Human off target predictions are calculated from the siSPOTR algorithm (world wide web at https://sispotr.icts.uiowa.edu/sispotr/ tools.html) and represents predicted off target transcripts based complementarity to the seed sequence of the miRNA.

IV. Neurodegenerative Synucleinopathies

Neurodegenerative synucleinopathies are neurodegenerative diseases characterized by increased levels of alpha-synuclein (SNCA) protein in neurons, nerve fibers or glial cells. Main types of neurodegenerative synucleinopathies include dementia with Lewy bodies (DLB), Parkinson's disease, and multiple system atrophy (MSA).

Examples of neurodegenerative synucleinopathies include, but are not limited to, Parkinson's disease (PD), multiple system atrophy (MSA-P and MSA-C), dementia with Lewy bodies (DLB), pure autonomic failure (PAF), Lewy body variant of Alzheimer's disease (LBVAD), Lewy body dysphagia, and incidental Lewy body disease.

Multiple lines of evidence demonstrate that increased levels of alpha-synuclein are neurotoxic, while reduction is neuroprotective (Dauer, 2002; Drolet, 2004; Alvarez-Fischer, 2008; Klivenyi, 2005; Mittal, 2017; Javed, 2015; Cole, 2017; Ubhi, 2010; Lim, 2011). Provided in this disclosure is RNAi against SNCA.

V. Methods to Treat Neurodegenerative Synucleinopathies

In some aspects, the disclosure provides methods and compositions for treating Neurodegenerative synucleinopathies in a mammal comprising administering to the mammal a pharmaceutical composition of the present disclosure (e.g., a pharmaceutical composition comprising a viral particle of the present disclosure). In some aspects, the disclosure provides methods and compositions for inhibiting the expression of SNCA in a mammal with a neurodegenerative synucleinopathy comprising administering to the mammal a pharmaceutical composition of the present disclosure (e.g., a pharmaceutical composition comprising a viral particle of the present disclosure). In some aspects, the disclosure provides methods and compositions for inhibiting the accumulation of SNCA in a cell of a mammal with a neurodegenerative synucleinopathy comprising administering to the mammal a pharmaceutical composition of the present disclosure (e.g., a pharmaceutical composition comprising a viral particle of the present disclosure).

In some aspects, the disclosure provides methods and compositions for ameliorating a symptom of a neurodegenerative synucleinopathy, comprising administration of an effective amount of recombinant viral particles comprising a vector encoding an RNAi of the present disclosure to the nervous system of a mammal. In some embodiments, the symptoms of a neurodegenerative synucleinopathy include, but are not limited to, parkinsonism, impaired cognition, sleep disorders, visual hallucinations, impaired speech, constipation, pyramidal or cerebellar signs, anosmia, autonomic dysfunction such as orthostatic hypotension, decreased sweating, erectile dysfunction, urine retention or incontinence and pupillary dysfunction.

In some aspects, the disclosure provides methods to prevent or delay progression of a neurodegenerative synucleinopathy. Synucleinopathies like PD are typically diagnosed clinical by the presence of tremor, bradykinesia, stiffness, and postural instability. Differentiation from PD is typical performed by checking for additional signs such as orthostatic hypotension, pyramidal signs, cognitive changes or hallucinations. Additionally, some synucleinopathies can be diagnosed by brain imaging, for example by looking for abnormalities in brain regions such as the pons, cerebellum, putamen in MSA. Some synucleinopathies can be directly identified via genotyping for common mutations not necessarily limited the SNCA gene. Delay or prevention of disease progression could be defined by improvement in any of the following symptoms: motor function (bradykinesia, dyskinesia, dystonia, postural instability, stooped posture, tremor, myoclonus etc), cognition, sleep disorders, visual hallucinations, speech, constipation, pyramidal signs, anosmia, autonomic dysfunction such as orthostatic hypotension, decreased sweating, erectile dysfunction, urine retention or incontinence and pupillary dysfunction.

In some aspects of the disclosure, the methods and compositions are used for the treatment of humans with a neurodegenerative synucleinopathy. In some aspects, the disclosure provides an improved RNAi for targeting SNCA mRNA in a mammal with a neurodegenerative synucleinopathy. In some embodiments, the RNAi comprises a first strand comprising a first nucleic acid comprising the sequence 5'-UGCUCUUUGGUCUUCUCAGCC-3' (SEQ ID NO: 24) and a second strand comprising a second nucleic acid comprising the sequence 5'-GGCUGAGAAC-CAAAGAGUA-3' (SEQ ID NO:53), where the first strand and second strand form a duplex and wherein the A residue at residue 19 of SEQ ID NO:53 of the second strand does not form a basepair with a residue in the first strand. In some embodiments, the miRNA comprises an internal bulge generated by deleting 2 based from the passenger strand of the miRNA-bases 9-10, counting from the start of the passenger strand. In some embodiments, the first strand and the second strand are linked by a loop sequence. In some embodiments, the loop sequence is 5'-GUUUUGGCCACUGACUGAC-3' (SEQ ID NO:60).

In some embodiments, the RNAi comprises a first strand comprising a first nucleic acid comprising the sequence 5'-UGGGCACAUUGGAACUGAGCA-3' (SEQ ID NO:8) and a second strand comprising a second nucleic acid comprising the sequence 5'-UGCUCAGUCAAUGUGC-CUA-3' (SEQ ID NO:37), where the first strand and second strand form a duplex and wherein the A residue 19 of SEQ ID NO:37 of the second strand does not form a basepair with a residue in the first strand. In some embodiments, the miRNA comprises an internal bulge generated by deleting 2 based from the passenger strand of the miRNA-bases 9-10, counting from the start of the passenger strand. In some embodiments, the first strand and the second strand are linked by a loop sequence. In some embodiments, the loop sequence is 5'-GUUUUGGCCACUGACUGAC-3' (SEQ ID NO:60).

In some embodiments, the RNAi comprises a first strand comprising a first nucleic acid comprising the sequence 5'-UGCGCUUUGGUCUUCUCAGCC-3' (SEQ ID NO:14) and a second strand comprising a second nucleic acid comprising the sequence 5'-GGCUGAGAAC-CAAAGCGUA-3' (SEQ ID NO:43), where the first strand and second strand form a duplex and wherein the A residue at residue 19 of SEQ ID NO:43 of the second strand does not form a basepair with a residue in the first strand. In some embodiments, the miRNA comprises an internal bulge generated by deleting 2 based from the passenger strand of the miRNA-bases 9-10, counting from the start of the passenger strand. In some embodiments, the first strand and the second strand are linked by a loop sequence. In some embodiments, the loop sequence is 5'-GUUUUGGCCACUGACUGAC-3' (SEQ ID NO:60).

In some embodiments, the RNAi comprises a first strand comprising a first nucleic acid comprising the sequence 5'-UGGGCGCAUUGGAACUGAGCA-3' (SEQ ID NO:7) and a second strand comprising a second nucleic acid comprising the sequence 5'-UGCUCAGUCAAUGCGC-CUA-3' (SEQ ID NO:36), where the first strand and second strand form a duplex and wherein the A residue at residue 19 of SEQ ID NO:36 of the second strand does not form a basepair with a residue in the first strand. In some embodiments, the miRNA comprises an internal bulge generated by deleting 2 based from the passenger strand of the miRNA-bases 9-10, counting from the start of the passenger strand. In some embodiments, the first strand and the second strand are linked by a loop sequence. In some embodiments, the loop sequence is 5'-GUUUUGGCCACUGACUGAC-3' (SEQ ID NO:60).

In some embodiments, the RNAi comprises a first strand comprising a first nucleic acid comprising the sequence 5'-uUCCAACAUUUGUCACUUGCU-3' (SEQ ID NO:5) and a second strand comprising a second nucleic acid comprising the sequence 5'-AGCAAGUGAAAU-GUUCGAA-3' (SEQ ID NO:34), where the first strand and second strand form a duplex and wherein the A residue at residue 18 or residue 19 of SEQ ID NO:34 of the second strand does not form a basepair with a residue in the first strand. In some embodiments, the miRNA comprises an internal bulge generated by deleting 2 based from the passenger strand of the miRNA-bases 9-10, counting from the start of the passenger strand. In some embodiments, the first strand and the second strand are linked by a loop sequence. In some embodiments, the loop sequence is 5'-GUUUUGGCCACUGACUGAC-3' (SEQ ID NO:60).

In some embodiments of the disclosure, the RNAi is improved to reduce off-target gene silencing. In some embodiments, the RNAi comprises one or more CpG motifs. In some embodiments, the RNAi comprises one or more CpG motifs in a seed region.

In some embodiments the disclosure provides methods for treating a neurodegenerative synucleinopathy in a mammal comprising administering to the mammal an RNAi comprising a first strand comprising a first nucleic acid comprising the sequence 5'-UGCUCUUUGGUCUUCUCAGCC-3' (SEQ ID NO:24) and a second strand comprising a second nucleic acid comprising the sequence 5'-GGCUGAGAAC-CAAAGAGUA-3' (SEQ ID NO: 53), where the first strand and second strand form a duplex. In some embodiments, the miRNA comprises an internal bulge generated by deleting 2 based from the passenger strand of the miRNA-bases 9-10, counting from the start of the passenger strand. In some embodiments the disclosure provides methods for inhibiting the expression of SNCA in a mammal with a neurodegenerative synucleinopathy comprising administering to the mammal an RNAi comprising a first strand comprising a first nucleic acid comprising the sequence 5'-UGCUC-UUUGGUCUUCUCAGCC-3' (SEQ ID NO:24) and a second strand comprising a second nucleic acid comprising the sequence 5'-GGCUGAGAACCAAAGAGUA-3' (SEQ ID NO: 53), where the first strand and second strand form a duplex. In some embodiments the disclosure provides methods for inhibiting the accumulation of SNCA in a cell of a mammal with a neurodegenerative synucleinopathy comprising administering to the mammal an RNAi comprising a first strand comprising a first nucleic acid comprising the sequence 5'-UGCUCUUUGGUCUUCUCAGCC-3' (SEQ ID NO:24) and a second strand comprising a second nucleic acid comprising the sequence 5'-GGCUGAGAAC-CAAAGAGUA-3' (SEQ ID NO: 53), where the first strand and second strand form a duplex. In some embodiments, the miRNA comprises an internal bulge generated by deleting 2 based from the passenger strand of the miRNA-bases 9-10, counting from the start of the passenger strand. In some embodiments, the first strand comprises a nucleic acid sequence having more than about any of 75%, 80%, 85%, 90%, 95%, 96%, 97%, 98% or 99% identity to SEQ ID NO:24. In some embodiments, the second strand comprises a nucleic acid sequence having more than about any of 75%, 80%, 85%, 90%, 95%, 96%, 97%, 98% or 99% identity to SEQ ID NO:24 but maintains the CpG motif. In some embodiments, the first strand and the second strand are linked by a loop sequence. In some embodiments, the loop sequence is 5'-GUUUUGGCCACUGACUGAC-3' (SEQ ID NO:60).

In some embodiments the disclosure provides methods for treating a neurodegenerative synucleinopathy in a mammal comprising administering to the mammal an RNAi comprising a first strand comprising a first nucleic acid comprising the sequence 5'-UGGGCACAUUGGAACUGAGCA-3' (SEQ ID NO:8) and a second strand comprising a second nucleic acid comprising the sequence 5'-UGCUCAGU-CAAUGUGCCUA-3' (SEQ ID NO: 37), where the first strand and second strand form a duplex. In some embodiments the disclosure provides methods for inhibiting the expression of SNCA in a mammal with a neurodegenerative synucleinopathy comprising administering to the mammal an RNAi comprising a first strand comprising a first nucleic acid comprising the sequence 5'-UGGGCACAUUG-GAACUGAGCA-3' (SEQ ID NO:8) and a second strand comprising a second nucleic acid comprising the sequence 5'-UGCUCAGUCAAUGUGCCUA-3' (SEQ ID NO: 37), where the first strand and second strand form a duplex. In some embodiments the disclosure provides methods for inhibiting the accumulation of SNCA in a cell of a mammal with a neurodegenerative synucleinopathy comprising administering to the mammal an RNAi comprising a first strand comprising a first nucleic acid comprising the sequence 5'-5'-UGGGCACAUUGGAACUGAGCA-3'-3' (SEQ ID NO:8) and a second strand comprising a second nucleic acid comprising the sequence 5'-UGCUCAGU-CAAUGUGCCUA-3' (SEQ ID NO: 37), where the first strand and second strand form a duplex. In some embodiments, the miRNA comprises an internal bulge generated by deleting 2 based from the passenger strand of the miRNA-bases 9-10, counting from the start of the passenger strand. In some embodiments, the first strand comprises a nucleic acid sequence having more than about any of 75%, 80%, 85%, 90%, 95%, 96%, 97%, 98% or 99% identity to SEQ ID NO:8. In some embodiments, the second strand comprises a nucleic acid sequence having more than about any of 75%, 80%, 85%, 90%, 95%, 96%, 97%, 98% or 99% identity to SEQ ID NO:37. In some embodiments, the first strand and the second strand are linked by a loop sequence. In some embodiments, the loop sequence is 5'-GUUUUGGCCA-CUGACUGAC-3' (SEQ ID NO:60).

In some embodiments, the RNAi is a small inhibitory RNA (siRNA), a microRNA (miRNA), or a small hairpin RNA (shRNA). A small inhibitory or interfering RNA (siRNA) is known in the art as a double-stranded RNA molecule of approximately 19-25 (e.g., 19-23) base pairs in length that induces RNAi in a cell. A small hairpin RNA (shRNA) is known in the art as an RNA molecule comprising approximately 19-25 (e.g., 19-23) base pairs of double stranded RNA linked by a short loop (e.g., ~4-11 nucleotides) that induces RNAi in a cell.

In some embodiments, the miRNA comprises a guide sequence that is about 90% identical to SEQ ID NO:24. In some embodiments, the miRNA comprises a guide sequence that is about any of 90% identical, 91% identical, 92% identical, 93% identical, 94% identical, 95% identical, 96% identical, 97% identical, 98% identical, 99% identical, or 100% identical to SEQ ID NO: 24.

In some embodiments, the miRNA comprises a non-guide sequence that is about 90% identical to SEQ ID NO:24. In some embodiments, the miRNA comprises a non-guide sequence that is about any of 90% identical, 91% identical, 92% identical, 93% identical, 94% identical, 95% identical, 96% identical, 97% identical, 98% identical, 99% identical, or 100% identical to SEQ ID NO:53. Any RNAi described herein (e.g., as part of a rAAV vector) may find use, inter alia, in treating a neurodegenerative synucleinopathy. In another aspect, any RNAi described in Table 1 can be used in treating a neurodegenerative synucleinopathy.

In some embodiments, the miRNA comprises a guide sequence that is about 90% identical to SEQ ID NO:8. In some embodiments, the miRNA comprises a guide sequence that is about any of 90% identical, 91% identical, 92% identical, 93% identical, 94% identical, 95% identical, 96% identical, 97% identical, 98% identical, 99% identical, or 100% identical to SEQ ID NO: 8.

In some embodiments, the miRNA comprises a non-guide sequence that is about 90% identical to SEQ ID NO:37. In some embodiments, the miRNA comprises a non-guide sequence that is about any of 90% identical, 91% identical, 92% identical, 93% identical, 94% identical, 95% identical, 96% identical, 97% identical, 98% identical, 99% identical, or 100% identical to SEQ ID NO:37. Any RNAi described herein (e.g., as part of a rAAV vector) may find use, inter alia, in treating a neurodegenerative synucleinopathy. In another aspect, any RNAi described in Table 1 can be used in treating a neurodegenerative synucleinopathy.

In some embodiments, the first strand and the second strand are linked by means of RNA capable of forming a loop structure. As is commonly known in the art, an RNA loop structure (e.g., a stem-loop or hairpin) is formed when an RNA molecule comprises two sequences of RNA that basepair together separated by a sequence of RNA that does not base pair together. For example, a loop structure may form in the RNA molecule A-B-C if sequences A and C are complementary or partially complementary such that they base pair together, but the bases in sequence B do not base pair together.

In some embodiments, the RNA capable of forming a loop structure comprises from 4 to 50 nucleotides. In certain embodiments, the RNA capable of forming a loop structure comprises 13 nucleotides. In certain embodiments, the RNA capable of forming a loop structure comprises the nucleotide sequence of SEQ ID NO:60. In some embodiments, the vector genome comprises a nucleotide sequence that is at least about any of 80%, 85%, 90%, 91%, 92%, 93%, 94%, 95%, 96%, 97%, 98%, or 99% identical to the sequence of SEQ ID NO:60.

In some embodiments, delivery of recombinant viral particles is by injection of viral particles to the brain. In some embodiments, delivery of recombinant viral particles is by injection of viral particles to the striatum. Intrastriatal administration delivers recombinant viral particles to an area of the brain, the striatum (including the putamen and caudate nucleus), that is highly affected by a neurodegenerative synucleinopathy. In addition, and without wishing to be bound to theory, it is thought that recombinant viral particles (e.g., rAAV particles) injected into the striatum may be also dispersed (e.g., through retrograde transport) to other areas of the brain, including without limitation projection areas (e.g., the cortex or substantia nigra). In some embodiments, the recombinant viral particles are delivered by convection enhanced delivery (e.g., convection enhanced delivery to the striatum).

In some aspects, the disclosure provides methods for treating a neurodegenerative synucleinopathy in a mammal comprising administering to the mammal the pharmaceutical composition of the present disclosure. In some aspects, the disclosure provides methods for inhibiting the accumulation of SNCA in a cell of a mammal with a neurodegenerative synucleinopathy comprising administering to the mammal the pharmaceutical composition of the present disclosure. In some aspects, the disclosure provides methods for inhibiting the expression of SNCA in a mammal with a neurodegenerative synucleinopathy comprising administering to the mammal the pharmaceutical composition of the present disclosure. In some embodiments, the SNCA is a mutant SNCA (e.g., human SNCA mutations including one or more of A53T, E46K, A30P, G51D, H50Q, A53E, A29S, A18T, and duplications and triplications of the gene locus). In some embodiments, expression and/or accumulation of a wild-type SNCA is also inhibited. As described herein, and without wishing to be bound to theory, it is thought that inhibition of expression and/or accumulation of mutant SNCA in a mammal with a neurodegenerative synucleinopathy is highly beneficial, but the inhibition of expression and/or accumulation of wild-type SNCA in the same mammal as a side effect (e.g., of an RNAi of the present disclosure) may be well tolerated (e.g., produces few or no unintended side effects).

In some embodiments, a cell comprises a vector (e.g., a vector comprising an expression construct encoding an RNAi of the present disclosure). In some embodiments, the vector is a rAAV vector. In some embodiments, the vector is a recombinant adenoviral vector, a recombinant lentiviral vector or a recombinant herpes simplex virus (HSV) vector. In some embodiments, the cell is a central nervous system (CNS) cell. In some embodiments, the cell is a HEK293 cell.

In some embodiments, the administration of an effective amount of recombinant viral particles comprising a vector encoding an RNAi of the present disclosure transduces neurons (e.g., striatal neurons, such as spiny neurons) at or near the site of administration. In some embodiments, more than about any of 5%, 10%, 15%, 20%, 25%, 30%, 35%, 40%, 45%, 50%, 55%, 60%, 65%, 70%, 75% or 100% of neurons are transduced. In some embodiments, about 5% to about 100%, about 10% to about 50%, about 10% to about 30%, about 25% to about 75%, about 25% to about 50%, or about 30% to about 50% of the neurons are transduced. Methods to identify neurons transduced by recombinant viral particles expressing miRNA are known in the art; for example, immunohistochemistry, RNA detection (e.g., qPCR, Northern blotting, RNA-seq, in situ hybridization, and the like) or the use of a co-expressed marker such as enhanced green fluorescent protein can be used to detect expression.

In some embodiments of the disclosure, the methods comprise administration to the brain of a mammal an effective amount of recombinant viral particles comprising a vector encoding an RNAi of the present disclosure for treating a mammal, e.g., a human, with a neurodegenerative synucleinopathy. In some embodiments, the composition is injected to one or more locations in the brain to allow expression of an RNAi of the present disclosure in at least the neurons. In some embodiments, the composition is injected into any one of one, two, three, four, five, six, seven, eight, nine, ten or more than ten locations in the brain. In some embodiments, the composition is injected into the striatum. In some embodiments, the composition is injected into the dorsal striatum. In some embodiments, the composition is injected into the putamen. In some embodiments, the composition is injected into the caudate nucleus. In some embodiments, the composition is injected into the putamen and into the caudate nucleus. In some embodiments, administration routes may include CSF delivery via intracerebroventricular, cisterna *magna* or intrathecal injection. In some embodiments, administration may also include intravenous delivery of the viral vector.

In some embodiments, the recombinant viral particles are administered to one hemisphere of the brain. In some embodiments, the recombinant viral particles are administered to both hemispheres of the brain.

In some embodiments the recombinant viral particles are administered to more than one location simultaneously or sequentially. In some embodiment, multiple injections of recombinant viral particles are no more than one hour, two hours, three hours, four hours, five hours, six hours, nine hours, twelve hours or 24 hours apart.

In some embodiments, the disclosure provides a method for treating a human with a neurodegenerative synucleinopathy by administering an effective amount of a pharmaceutical composition comprising a recombinant viral vector encoding an RNAi of the present disclosure to suppress the activity of a mutant SNCA. In some embodiments, the pharmaceutical composition comprises one or more pharmaceutically acceptable excipients.

In some embodiments, the methods comprise administering an effective amount of a pharmaceutical composition comprising a recombinant viral vector encoding an RNAi of the present disclosure to suppress the activity of a mutant SNCA. In some embodiments, the viral titer of the viral particles (e.g., rAAV particles) is at least about any of $5\times10^{12}$, $6\times10^{12}$, $7\times10^{12}$, $8\times10^{12}$, $9\times10^{12}$, $10\times10^{12}$, $11\times10^{12}$, $15\times10^{12}$, $20\times10^{12}$, $25\times10^{12}$, $30\times10^{12}$, or $50\times10^{12}$ genome copies/mL. In some embodiments, the viral titer of the viral particles (e.g., rAAV particles) is about any of $5\times10^{12}$ to $6\times10^{12}$, $6\times10^{12}$ to $7\times10^{12}$, $7\times10^{12}$ to $8\times10^{12}$, $8\times10^{12}$ to $9\times10^{12}$, $9\times10^{12}$ to $10\times10^{12}$, $10\times10^{12}$ to $11\times10^{12}$, $11\times10^{12}$ to $15\times10^{12}$, $15\times10^{12}$ to $20\times10^{12}$, $20\times10^{12}$ to $25\times10^{12}$, $25\times10^{12}$ to $30\times10^{12}$, $30\times10^{12}$ to $50\times10^{12}$, or $50\times10^{12}$ to $100\times10^{12}$ genome copies/mL. In some embodiments, the viral titer of the viral particles (e.g., rAAV particles) is about any of $5\times10^{12}$ to $10\times10^{12}$, $10\times10^{12}$ to $25\times10^{12}$, or $25\times10^{12}$ to $50\times10^{12}$ genome copies/mL. In some embodiments, the viral titer of the viral particles (e.g., rAAV particles) is at least about any of $5\times10^{9}$, $6\times10^{9}$, $7\times10^{9}$, $8\times10^{9}$, $9\times10^{9}$, $10\times10^{9}$, $11\times10^{9}$, $15\times10^{9}$, $20\times10^{9}$, $25\times10^{9}$, $30\times10^{9}$, or $50\times10^{9}$ transducing units/mL. In some embodiments, the viral titer of the viral particles (e.g., rAAV particles) is about any of $5\times10^{9}$ to $6\times10^{9}$, $6\times10^{9}$ to $7\times10^{9}$, $7\times10^{9}$ to $8\times10^{9}$, $8\times10^{9}$ to $9\times10^{9}$, $9\times10^{9}$ to $10\times10^{9}$, $10\times10^{9}$ to $11\times10^{9}$, $11\times10^{9}$ to $15\times10^{9}$, $15\times10^{9}$ to $20\times10^{9}$, $20\times10^{9}$ to $25\times10^{9}$, $25\times10^{9}$ to $30\times10^{9}$, $30\times10^{9}$ to $50\times10^{9}$ or $50\times10^{9}$ to $100\times10^{9}$ transducing units/mL. In some embodiments, the viral titer of the viral particles (e.g., rAAV particles) is about any of $5\times10^{9}$ to $10\times10^{9}$, $10\times10^{9}$ to $15\times10^{9}$, $15\times10^{9}$ to $25\times10^{9}$, or $25\times10^{9}$ to $50\times10^{9}$ transducing units/mL. In some embodiments, the viral titer of the viral particles (e.g., rAAV particles) is at least any of about $5\times10^{10}$, $6\times10^{10}$, $7\times10^{10}$, $8\times10^{10}$, $9\times10^{10}$, $10\times10^{10}$, $11\times10^{10}$, $15\times10^{10}$, $20\times10^{10}$, $25\times10^{10}$, $30\times10^{10}$, $40\times10^{10}$ or $50\times10^{10}$ infectious units/mL. In some embodiments, the viral titer of the viral particles (e.g., rAAV particles) is at least any of about $5\times10^{10}$ to $6\times10^{10}$, $6\times10^{10}$ to $7\times10^{10}$, $7\times10^{10}$ to $8\times10^{10}$, $8\times10^{10}$ to $9\times10^{10}$, $9\times10^{10}$ to $10\times10^{10}$, $10\times10^{10}$ to $11\times10^{10}$, $11\times10^{10}$ to $15\times10^{10}$, $15\times10^{10}$ to $20\times10^{10}$, $20\times10^{10}$ to $25\times10^{10}$, $25\times10^{10}$ to $30\times10^{10}$, $30\times10^{10}$ to $40\times10^{10}$, $40\times10^{10}$ to $50\times10^{10}$, or $50\times10^{10}$ to $100\times10^{10}$ infectious units/mL. In some embodiments, the viral titer of the viral particles (e.g., rAAV particles) is at least any of about $5\times10^{10}$ to $10\times10^{10}$, $10\times10^{10}$ to $15\times10^{10}$, $15\times10^{10}$ to $25\times10^{10}$, or $25\times10^{10}$ to $50\times10^{10}$ infectious units/mL.

In some embodiments, the dose of viral particles administered to the individual is at least about any of $1\times10^{8}$ to about $1\times10^{13}$ genome copies/kg of body weight. In some embodiments, the dose of viral particles administered to the individual is about any of $1\times10^{8}$ to about $1\times10^{13}$ genome copies/kg of body weight.

In some embodiments, the total amount of viral particles administered to the individual is at least about any of $1\times10^{9}$ to about $1\times10^{14}$ genome copies. In some embodiments, the total amount of viral particles administered to the individual is about any of $1\times10^{9}$ to about $1\times10^{14}$ genome copies.

In some embodiments of the disclosure, the volume of the composition injected to the striatum is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount there in between.

In some embodiments, a first volume of the composition is injected into a first region of the brain, and a second volume of the composition is injected into a second region of the brain. For example, in some embodiments, a first volume of the composition is injected into the caudate nucleus, and a second volume of the composition is injected into the putamen. In some embodiments, a 1× volume of the composition is injected into the caudate nucleus, and a 1.5×, 2×, 2.5×, 3×, 3.5×, or 4× volume of the composition is injected into the putamen, where X is a volume that is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount therebetween.

Compositions of the disclosure (e.g., recombinant viral particles comprising a vector encoding an RNAi of the present disclosure) can be used either alone or in combination with one or more additional therapeutic agents for treating a neurodegenerative synucleinopathy. The interval between sequential administration can be in terms of at least (or, alternatively, less than) minutes, hours, or days.

Any RNAi, expression construct, vector, or cell described in this disclosure can be used in any method above. In some embodiments, any RNAi disclosed in Table 1, expression construct, vector, or cell comprising the RNAi in Table 1 can be used in any method described above.

V. RNAi Expression Constructs and Vectors

The disclosure provides expression constructs, vectors and viral particles for expression of the RNAi described herein.

In some embodiments, nucleic acid encoding an RNAi of the present disclosure comprises a heterologous miRNA scaffold. In some embodiments, use of a heterologous miRNA scaffold is used to modulate miRNA expression; for example, to increase miRNA expression or to decrease miRNA expression. Any miRNA scaffold known in the art may be used. In some embodiments, the miRNA scaffold is derived from a miR-155 scaffold (see, e.g., Lagos-Quintana, M. et al. (2002) *Curr. Biol.* 12:735-9 and the Invitrogen™ BLOCK-iT™ Pol II miR RNAi expression vector kit from Life Technologies, Thermo Fisher Scientific; Waltham, MA). In some embodiments, nucleic acid encoding an RNAi of the present disclosure comprises a miRNA scaffold. In some embodiments, miRNA scaffold comprises the sequence

```
                                    (SEQ ID NO: 67)
ctggaggcttgctgaaggctgtatgctgcaggacacaaggcctgttact
agcactcacatggaacaaatggc,
``` wherein the miRNA is inserted between the bolded gc residues.

In some embodiments, the miRNA in the scaffold comprises the sequence

```
                                    (SEQ ID NO: 68)
ctggaggcttgctgaaggctgtatgctgtacgatctaatatcgctcgtt ttggccactgactgacgagcgatatgatcgtacgacaggacacaaggcc tgttactagcactcacatggaacaaatggc
``` where the underlined regular text represents the 5'-flank, italics text represents the guide sequence, bolded text represents the loop, underlined italics represents the non-guide sequence and regular text represents the 3' flank.

In some embodiments, the RNAi targets RNA encoding a polypeptide associated with a neurodegenerative synucleinopathy. In some embodiments, the polypeptide is alpha-synuclein. Without wishing to be bound to theory, it is thought that an RNAi may be used to reduce or eliminate the expression and/or activity of a polypeptide whose gain-of-function has been associated with a neurodegenerative synucleinopathy. Non-limiting examples of a neurodegenerative synucleinopathy of the disclosure that may be treated by a therapeutic polypeptide or therapeutic nucleic acid of the disclosure (exemplary genes that may be targeted or supplied are provided in parenthesis for each disorder) include Parkinson's disease (SNCA), multiple system atrophy or MSA (SNCA), and dementia with Lewy bodies (SNCA).

In some embodiments, the transgene (e.g., an RNAi of the present disclosure) is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene*, 1991, 108 (2): 193-9) and the elongation factor 1-alpha promoter (EF1-alpha) promoter (Kim et al., *Gene*, 1990, 91 (2): 217-23 and Guo et al., *Gene Ther.*, 1996, 3 (9): 802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the disclosure provides a recombinant vector comprising nucleic acid encoding a heterologous transgene of the present disclosure operably linked to a CBA promoter. Exemplary promoters and descriptions may be found, e.g., in U.S. PG Pub. 20140335054. In some embodiments, the promoter is a CBA promoter, a minimum CBA promoter, a CMV promoter or a GUSB promoter. In some embodiments, the promoter is a hEF1a promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the 13-actin promoter, the phosphoglycerol kinase (PGK) promoter, and the EF1a promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, *Proc. Natl. Acad. Sci. USA*, 93:3346-3351 (1996)), the tetracycline-repressible system (Gossen et al, *Proc. Natl. Acad. Sci. USA*, 89:5547-5551 (1992)), the tetracycline-inducible system (Gossen et al, *Science*, 268:1766-1769 (1995), see also Harvey et al, *Curr. Opin. Chem. Biol.*, 2:512-518 (1998)), the RU486-inducible system (Wang et al, *Nat. Biotech.*, 15:239-243 (1997) and Wang et al, *Gene Ther.*, 4:432-441 (1997)) and the rapamycin-inducible system (Magari et al, *J. Clin. Invest.*, 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter, or fragment thereof, for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: neuronal such as neuron-specific enolase (NSE) promoter (Andersen et al., *Cell. Mol. Neurobiol.*, 13:503-15 (1993)), neurofilament light-chain gene promoter (Piccioli et al., *Proc. Natl. Acad. Sci. USA,* 88:5611-5 (1991)), and the neuron-specific vgf gene promoter (Piccioli et al., *Neuron,* 15:373-84 (1995)). In some embodiments, the tissue-specific promoter is a promoter of a gene selected from: neuronal nuclei (NeuN), glial fibrillary acidic protein (GFAP), adenomatous polyposis coli (APC), and ionized calcium-binding adapter molecule 1 (Iba-1). Other appropriate tissue specific promoters will be apparent to the skilled artisan. In some embodiments, the promoter is a chicken Beta-actin promoter.

In some embodiments, the promoter expresses the heterologous nucleic acid in a cell of the CNS. As such, in some embodiments, a therapeutic polypeptide or a therapeutic nucleic acid of the disclosure may be used to treat a disorder of the CNS. In some embodiments, the promoter expresses the heterologous nucleic acid in a brain cell. A brain cell may refer to any brain cell known in the art, including without limitation a neuron (such as a sensory neuron, motor neuron, interneuron, dopaminergic neuron, medium spiny neuron, cholinergic neuron, GABAergic neuron, pyramidal neuron, etc.), a glial cell (such as microglia, macroglia, astrocytes, oligodendrocytes, ependymal cells, radial glia, etc.), a brain parenchyma cell, microglial cell, ependemal cell, and/or a Purkinje cell. In some embodiments, the promoter expresses the heterologous nucleic acid in a neuron and/or glial cell. In some embodiments, the neuron is a medium spiny neuron of the caudate nucleus, a medium spiny neuron of the putamen, a neuron of the cortex layer IV and/or a neuron of the cortex layer V.

Various promoters that express transcripts (e.g., a heterologous transgene) in CNS cells, brain cells, neurons, and glial cells are known in the art and described herein. Such promoters can comprise control sequences normally associated with the selected gene or heterologous control sequences. Often, useful heterologous control sequences include those derived from sequences encoding mammalian or viral genes. Examples include, without limitation, the SV40 early promoter, mouse mammary tumor virus LTR promoter, adenovirus major late promoter (Ad MLP), a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, may also be used. Such promoter sequences are commercially available from, e.g., Stratagene (San Diego, CA). CNS-specific promoters and inducible promoters may be used. Examples of CNS-specific promoters include without limitation those isolated from CNS-specific genes such as myelin basic protein (MBP), glial fibrillary acid protein (GFAP), and neuron specific enolase (NSE). Examples of inducible promoters include DNA responsive elements for ecdysone, tetracycline, metallothionein, and hypoxia, inter alia.

The present disclosure contemplates the use of a recombinant viral genome for introduction of one or more nucleic acid sequences encoding for a RNAi as described herein or packaging into an AAV viral particle. The recombinant viral genome may include any element to establish the expression of a RNAi, for example, a promoter, a heterologous nucleic acid, an ITR, a ribosome binding element, terminator, enhancer, selection marker, intron, polyA signal, and/or origin of replication. In some embodiments, the rAAV vector comprises one or more of an enhancer, a splice donor/splice acceptor pair, a matrix attachment site, or a polyadenylation signal.

In some embodiments, the administration of an effective amount of rAAV particles comprising a vector encoding a RNAi transduces cells (e.g., CNS cells, brain cells, neurons, and/or glial cells) at or near the site of administration (e.g., the striatum and/or cortex) or more distal to the site of administration. In some embodiments, more than about any of 5%, 10%, 15%, 20%, 25%, 30%, 35%, 40%, 45%, 50%, 55%, 60%, 65%, 70%, 75% or 100% of neurons are transduced. In some embodiments, about 5% to about 100%, about 10% to about 50%, about 10% to about 30%, about 25% to about 75%, about 25% to about 50%, or about 30% to about 50% of the neurons are transduced. Methods to identify neurons transduced by recombinant viral particles expressing miRNA are known in the art; for example, immunohistochemistry, RNA detection (e.g., qPCR, Northern blotting, RNA-seq, in situ hybridization, and the like) or the use of a co-expressed marker such as enhanced green fluorescent protein can be used to detect expression.

In some aspects, the disclosure provides viral particles comprising a recombinant self-complementing genome (e.g., a self-complementary rAAV vector). AAV viral particles with self-complementing vector genomes and methods of use of self-complementing AAV genomes are described in U.S. Pat. Nos. 6,596,535; 7,125,717; 7,465,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a heterologous nucleic acid). In some embodiments, the vector comprises first nucleic acid sequence encoding the heterologous nucleic acid and a second nucleic acid sequence encoding a complement of the nucleic acid, where the first nucleic acid sequence can form intrastrand base pairs with the second nucleic acid sequence along most or all of its length.

In some embodiments, the first heterologous nucleic acid sequence encoding a RNAi and a second heterologous nucleic acid sequence encoding the complement of the RNAi are linked by a mutated ITR (e.g., the right ITR). In some embodiments, the ITR comprises the polynucleotide sequence 5'-CACTCCCTCTCTGCGCGCTCGCTCGCT-CACTGAGGCC GGGCGACCAAAGGTCGCC-CACGCCCGGGCTTTGCCCGGGCG-3' (SEQ ID NO:69). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

VI. Viral Particles and Methods of Producing Viral Particles

The disclosure provides, inter alia, recombinant viral particles comprising a nucleic acid encoding an RNAi of the present disclosure, as well as methods of use thereof to treat a disease or disorder in a mammal; e.g., a neurodegenerative synucleinopathy.

Viral Particles

The disclosure provides viral particles comprising the RNAi as disclosed herein. In some embodiments, the disclosure provides viral particles for delivering the RNAi of the disclosure as disclosed herein. For example, the disclosure provides methods of using recombinant viral particles to deliver RNAi to treat a disease or disorder in a mammal; e.g., rAAV particles comprising RNAi to treat a neurodegenerative synucleinopathy. In some embodiments, the recombinant viral particle is a recombinant AAV particle. In some embodiments, the viral particle is a recombinant AAV particle comprising a nucleic acid comprising a sequence an RNAi of the present disclosure flanked by one or two ITRs. The nucleic acid is encapsidated in the AAV particle. The AAV particle also comprises capsid proteins. In some embodiments, the nucleic acid comprises the coding sequence(s) of interest (e.g., nucleic acid an RNAi of the present disclosure) operatively linked components in the direction of transcription, control sequences including transcription initiation and termination sequences, thereby forming an expression construct. The expression construct is flanked on the 5' and 3' end by at least one functional AAV ITR sequences. By "functional AAV ITR sequences" it is meant that the ITR sequences function as intended for the rescue, replication and packaging of the AAV virion. See Davidson et al., PNAS, 2000, 97 (7) 3428-32; Passini et al., J. Virol., 2003, 77 (12): 7034-40; and Pechan et al., Gene Ther., 2009, 16:10-16, all of which are incorporated herein in their entirety by reference. For practicing some aspects of the disclosure, the recombinant vectors comprise at least all of the sequences of AAV essential for encapsidation and the physical structures for infection by the rAAV. AAV ITRs for use in the vectors of the disclosure need not have a wild-type nucleotide sequence (e.g., as described in Kotin, Hum. Gene Ther., 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., PNAS, 2002, 99 (18): 11854-6; Gao et al., PNAS, 2003, 100 (10): 6081-6; and Bossis et al., J. Virol., 2003, 77 (12): 6799-810. Use of any AAV serotype is considered within the scope of the present disclosure. In some embodiments, a rAAV vector is a vector derived from an AAV serotype, including without limitation, AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype or the like. In some embodiments, the nucleic acid in the AAV comprises an ITR of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype or the like. In some embodiments, the nucleic acid in the AAV further encodes an RNAi as described herein. In some embodiments the rAAV particle comprise an AAV1, an AAV2HBKO capsid (e.g., as described in WO2015168666), an AAV9 capsid, a PHP.B capsid, a PHP.eB capsid, or an Olig001 capsid.

For example, the nucleic acid in the AAV can comprise at least one ITR of any AAV serotype contemplated herein and can further encode an RNAi comprising a first strand and a second strand, wherein a) the first strand and the second form a duplex; b) the first strand comprises a guide region, and c) the second strand comprises a non-guide region, wherein the non-guide region comprises a two nucleotide deletion at bases 9 and 10 to create bulge in the guide strand. In some embodiments, the rAAV can comprise a first strand comprising a first nucleic acid comprising the sequence 5'-UGCUCUUUGGUCUUCUCAGCC-3' (SEQ ID NO: 24) and a second strand comprising a second nucleic acid comprising the sequence 5'-GGCUGAGAAC-CAAAGAGUA-3' (SEQ ID NO:53). In some embodiments, the rAAV can comprise a first strand comprising a first nucleic acid comprising the sequence 5'-UGGGCA-CAUUGGAACUGAGCA-3' (SEQ ID NO:8) and a second strand comprising a second nucleic acid comprising the sequence 5'-UGCUCAGUCAAUGUGCCUA-3' (SEQ ID NO: 37). In some embodiments, the nucleic acid in the AAV comprises 5' to 3' nucleic acid encoding the following: an ITR (e.g., an AAV2 ITR), a promoter, a nucleic acid encoding an RNAi as disclosed herein, a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a promoter, a nucleic acid encoding an RNAi comprising a first strand comprising a first nucleic acid comprising the sequence 5'-UGCUCUUUGGUCUUCUCAGCC-3' (SEQ ID NO:24) and a second strand comprising a second nucleic acid comprising the sequence 5'-GGCUGAGAAC-CAAAGAGUA-3' (SEQ ID NO: 53), a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a promoter, a nucleic acid encoding an RNAi comprising a first strand comprising a first nucleic acid comprising the sequence 5'-UGGGCACAUUG-GAACUGAGCA-3' (SEQ ID NO:8) and a second strand comprising a second nucleic acid comprising the sequence 5'-UGCUCAGUCAAUGUGCCUA-3' (SEQ ID NO: 37), a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a CBA promoter, a nucleic acid encoding an RNAi as disclosed herein, a polyadenylation signal (e.g., a bovine growth hormone polyA), and an AAV ITR (e.g., an AAV2 ITR). In some embodiments, the RNAi is selected from Table 1. In some embodiments, the nucleic acid in the AAV comprises 5' to 3' nucleic acid encoding the following: an ITR (e.g., an AAV2 ITR), a CBA promoter, a nucleic acid encoding an RNAi comprising a first strand comprising a first nucleic acid comprising the sequence 5'-UGCUCUUUGGUCUUCUCAGCC-3' (SEQ ID NO:24) and a second strand comprising a second nucleic acid comprising the sequence 5'-GGCUGAGAAC-CAAAGAGUA-3' (SEQ ID NO:53), a polyadenylation signal (e.g., a bovine growth hormone polyA), and an AAV ITR (e.g., an AAV2 ITR). In some embodiments, the nucleic acid in the AAV comprises 5' to 3' nucleic acid encoding the following: an ITR (e.g., an AAV2 ITR), a CBA promoter, a nucleic acid encoding an RNAi comprising a first strand comprising a first nucleic acid comprising the sequence 5'-UGGGCACAUUGGAACUGAGCA-3' (SEQ ID NO:8) and a second strand comprising a second nucleic acid comprising the sequence 5'-UGCUCAGUCAAUGUGC-CUA-3' (SEQ ID NO: 37), a polyadenylation signal (e.g., a bovine growth hormone polyA), and an AAV ITR (e.g., an AAV2 ITR). In some embodiments, the first and second strands are selected from Table 1.

In some embodiments, a vector may include a stuffer nucleic acid. In some embodiments, the stuffer nucleic acid may encode a green fluorescent protein. In some embodiments, the stuffer nucleic acid may be located between the promoter and the nucleic acid encoding the RNAi. In some embodiments, the stuffer nucleic acid is an A1AT stuffer nucleic acid.

In some embodiments, the nucleic acid in the AAV comprises the nucleic acid of SEQ ID NO:65. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:65. In further embodiments, the rAAV particle comprises capsid proteins of AAV1, AAV2, AAV3, AAV4, AAV5, AA6, AAV7, AAV8, AAV9, AAVrh.8, AAVrh8R, AAVrh.10, AAV11, AAV12, or mutants of these capsid proteins. In some embodiments, a mutant capsid protein maintains the ability to form an AAV capsid. In some embodiments, the rAAV particle comprises AAV5 tyrosine mutant capsid (Zhong L. et al., (2008) *Proc Natl Acad Sci USA* 105 (22): 7827-7832. In further embodiments, the rAAV particle comprises capsid proteins of an AAV serotype from Clades A-F (Gao, et al., *J. Virol.* 2004, 78 (12): 6381).

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. For example, in some embodiments a rAAV particle can comprise AAV1 capsid proteins and at least one AAV2 ITR or it can comprise AAV2 capsid proteins and at least one AAV1 ITR. Any combination of AAV serotypes for production of a rAAV particle is provided herein as if each combination had been expressly stated herein. In some embodiments, the invention provides rAAV particles comprising an AAV1 capsid and a rAAV vector of the present disclosure (e.g., an expression construct comprising nucleic acid encoding an RNAi of the present disclosure), flanked by at least one AAV2 ITR. In some embodiments, the invention provides rAAV particles comprising an AAV2 capsid. In some embodiments the rAAV particle comprise an AAV1, an AAV2HBKO capsid (e.g., as described in WO2015168666), an AAV9 capsid, a PHP.B capsid, a PHP.eB capsid, or an Olig001.

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,465,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., an RNAi of the present disclosure) and a second heterologous polynucleotide sequence (e.g., antisense strand of an RNAi of the present disclosure) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in miRNA or siRNA molecules. In some embodiments, the first heterologous polynucleotide sequence and a second heterologous polynucleotide sequence are linked by a mutated ITR (e.g., the right ITR). In some embodiments, the ITR comprises the polynucleotide sequence 5'-ttggccactccctctctgcgcgctcgctcgctcactga-ggccgcccgggcaaagcccgggcgtcgggcgacctttggtcgcccggcctc-agtgagcgagcgagcgcgcagagagggagtggccaactccatcactagg-ggttcct-3' (SEQ ID NO:70). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR. In some embodiments, the invention provides AAV viral particles comprising a recombinant viral genome comprising a functional AAV2 ITR, a first polynucleotide sequence encoding an RNAi of the present disclosure, a mutated AAV2 ITR comprising a deletion of the D region and lacking a functional terminal resolution sequence, a second polynucleotide sequence comprising the complementary sequence to the sequence encoding an RNAi of the present disclosure, of the first polynucleotide sequence and a functional AAV2 ITR.

Production of Viral Particles rAAV particles can be produced using methods known in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

Methods known in the art for production of rAAV vectors include but are not limited to transfection, stable cell line production, and infectious hybrid virus production systems which include adenovirus-AAV hybrids, herpesvirus-AAV hybrids (Conway, J E et al., (1997) *J. Virology* 71 (11): 8780-8789) and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a nucleic acid (such as a therapeutic nucleic acid) flanked by at least one AAV ITR sequences; and 5) suitable media and media components to support rAAV production. In some embodiments, the AAV rep and cap gene products may be from any AAV serotype. In general, but not obligatory, the AAV rep gene product is of the same serotype as the ITRs of the rAAV vector genome as long as the rep gene products may function to replicated and package the rAAV genome. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors. In some embodiments, the AAV helper functions are provided by adenovirus or HSV. In some embodiments, the AAV helper functions are provided by baculovirus and the host cell is an insect cell (e.g., *Spodoptera frugiperda* (Sf9) cells).

In some embodiments, rAAV particles may be produced by a triple transfection method, such as the exemplary triple transfection method provided infra. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified. As such, in some embodiments, the rAAV particle was produced by triple transfection of a nucleic acid encoding the rAAV vector, a nucleic acid encoding AAV rep and cap, and a nucleic acid encoding AAV helper virus functions into a host cell, wherein the transfection of the nucleic acids to the host cells generates a host cell capable of producing rAAV particles.

In some embodiments, rAAV particles may be produced by a producer cell line method, such as the exemplary producer cell line method provided infra (see also (referenced in Martin et al., (2013) *Human Gene Therapy Methods* 24:253-269). Briefly, a cell line (e.g., a HeLa cell line) may be stably transfected with a plasmid containing a rep gene, a capsid gene, and a promoter-heterologous nucleic acid sequence. Cell lines may be screened to select a lead clone for rAAV production, which may then be expanded to a production bioreactor and infected with an adenovirus (e.g., a wild-type adenovirus) as helper to initiate rAAV production. Virus may subsequently be harvested, adenovirus may be inactivated (e.g., by heat) and/or removed, and the rAAV particles may be purified. As such, in some embodiments, the rAAV particle was produced by a producer cell line comprising one or more of nucleic acid encoding the rAAV vector, a nucleic acid encoding AAV rep and cap, and a nucleic acid encoding AAV helper virus functions.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) an rAAV pro-vector comprising a nucleic acid encoding an RNAi of the present disclosure as described herein flanked by at least one AAV ITR, and (iii) an AAV helper function; and (b) recovering the rAAV particles produced by the host cell. In some embodiments, the RNAi comprises the nucleotide sequence of SEQ ID NO:61 (FIG. 1A) or SEQ ID NO:63 (FIG. 1B). In some embodiments, said at least one AAV ITR is selected from the group consisting of AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, said encapsidation protein is selected from the group consisting of AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub. 2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, or an AAV capsid described in U.S. Pat. No. 8,283,151 or International Publication No. WO/2003/042397. In some embodiments, the AAV capsid is an AAV2HBKO capsid as described in WO2015168666. In some embodiments, the AAV capsid is an AAV9 capsid. In some embodiments, the AAV capsid is a PHP.B, PHP.eB or an Olig001 capsid. In some embodiments, a mutant capsid protein maintains the ability to form an AAV capsid. In some embodiments, the encapsidation protein is an AAV5 tyrosine mutant capsid protein. In further embodiments, the rAAV particle comprises capsid proteins of an AAV serotype from Clades A-F. In some embodiments, the rAAV particles comprise an AAV1 capsid and a recombinant genome comprising AAV2 ITRs and nucleic acid encoding an RNAi of the present disclosure. In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

Numerous methods are known in the art for production of adenoviral vector particles. For example, for a gutted adenoviral vector, the adenoviral vector genome and a helper adenovirus genome may be transfected into a packaging cell line (e.g., a 293 cell line). In some embodiments, the helper adenovirus genome may contain recombination sites flanking its packaging signal, and both genomes may be transfected into a packaging cell line that expresses a recombinase (e.g., the Cre/loxP system may be used), such that the adenoviral vector of interest is packaged more efficiently than the helper adenovirus (see, e.g., Alba, R. et al. (2005) *Gene Ther.* 12 Suppl 1: S18-27). Adenoviral vectors may be harvested and purified using standard methods, such as those described herein.

Numerous methods are known in the art for production of lentiviral vector particles. For example, for a third-generation lentiviral vector, a vector containing the lentiviral genome of interest with gag and pol genes may be co-transfected into a packaging cell line (e.g., a 293 cell line) along with a vector containing a rev gene. The lentiviral genome of interest also contains a chimeric LTR that promotes transcription in the absence of Tat (see Dull, T. et al. (1998) *J. Virol.* 72:8463-71). Lentiviral vectors may be harvested and purified using methods (e.g., Segura M M, et al., (2013) *Expert Opin Biol Ther.* 13 (7): 987-1011) described herein.

Numerous methods are known in the art for production of HSV particles. HSV vectors may be harvested and purified using standard methods, such as those described herein. For example, for a replication-defective HSV vector, an HSV genome of interest that lacks all of the immediate early (IE) genes may be transfected into a complementing cell line that provides genes required for virus production, such as ICP4, ICP27, and ICP0 (see, e.g., Samaniego, L. A. et al. (1998) *J. Virol.* 72:3307-20). HSV vectors may be harvested and purified using methods described (e.g., Goins, W F et al., (2014) Herpes Simplex Virus Methods in Molecular Biology 1144:63-79).

Also provided herein are pharmaceutical compositions comprising a recombinant viral particle comprising a transgene encoding an RNAi of the present disclosure and a pharmaceutically acceptable carrier. The pharmaceutical compositions may be suitable for any mode of administration described herein. A pharmaceutical composition of a recombinant viral particle comprising a nucleic acid encoding an RNAi of the present disclosure can be introduced to the brain. For example, a recombinant viral particle comprising a nucleic acid encoding an RNAi of the present disclosure can be administered intrastriatally. Any of the recombinant viral particles of the present disclosure may be used, including rAAV, adenoviral, lentiviral, and HSV particles.

In some embodiments, the pharmaceutical compositions comprising a recombinant viral particle comprising a transgene encoding an RNAi of the present disclosure described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for injection into the brain of a mammal (e.g., intrastriatal administration). In some embodiments, the pharmaceutical compositions comprising a recombinant lentiviral particle described herein and a pharmaceutically acceptable carrier is suitable for injection into the brain of a mammal (e.g., intrastriatal administration). In some embodiments, the pharmaceutical compositions comprising a recombinant adenoviral particle described herein and a pharmaceutically acceptable carrier is suitable for injection into the brain of a mammal (e.g., intrastriatal administration). In some embodiments, the pharmaceutical compositions comprising a recombinant HSV particle described herein and a pharmaceutically acceptable carrier is suitable for injection into the brain of a mammal (e.g., intrastriatal administration).

Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

VII. Articles of Manufacture and Kits

Also provided are kits or articles of manufacture for use in the methods described herein. In aspects, the kits comprise the compositions described herein (e.g., a recombinant viral particle of the present disclosure, such as a rAAV particle comprising nucleic acid encoding an RNAi of the present disclosure) in suitable packaging. Suitable packaging for compositions (such as intrastriatal compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein. For example, in some embodiments, the kit comprises a composition of recombinant viral particles comprising a transgene encoding an RNAi of the present disclosure for delivery of at least $1\times10^9$ genome copies into the brain of a mammal (e.g., through intrastriatal administration) to a primate as described herein, a pharmaceutically acceptable carrier suitable for injection into the brain of a primate, and one or more of: a buffer, a diluent, a filter, a needle, a syringe, and a package insert with instructions for performing injections into the brain of a primate (e.g., intrastriatal administration). In some embodiments, the kit comprising instructions for treating a neurodegenerative synucleinopathy with the recombinant viral particles described herein. In some embodiments, the kit comprising instructions for using the recombinant viral particles described herein according to any one of the methods described herein VIII. Exemplary Embodiments 1. An RNAi comprising a first strand and a second strand, wherein a) the first strand and the second strand form a duplex; b) the first strand comprises a guide region, wherein the guide region comprises a nucleic acid having at least about 90% identity to the sequence 5'-UGCUCUUUGGU-CUUCUCAGCC-3' (SEQ ID NO:24) or at least about 90% identity to the sequence 5'-UGGGCACAUUG-GAACUGAGCA-3' (SEQ ID NO:8); and c) the second strand comprises a non-guide region.

2. The RNAi of embodiment 1, wherein the guide region comprises the nucleic acid sequence 5'-UGCUCUUUGGU-CUUCUCAGCC-3' (SEQ ID NO:24) and the non-guide region comprises the sequence 5'-GGCUGAGAAC-CAAAGAGUA-3' (SEQ ID NO:53).

3. The RNAi of embodiment 1, wherein the first strand comprises a nucleic acid sequence having about 90% identity to SEQ ID NO:24 or about 90% identity to SEQ ID NO:53.

4. The RNAi of embodiment 1, wherein the guide region comprises the nucleic acid sequence 5'-UGGGCACAUUG-GAACUGAGCA-3' (SEQ ID NO:8) and the non-guide region comprises the sequence 5'-UGCUCAGUCAAU-GUGCCUA-3' (SEQ ID NO:37).

5. The RNAi of embodiment 1, wherein the second strand comprises a nucleic acid sequence having about 90% identity to SEQ ID NO:37 or about 90% identity to SEQ ID NO:37.

6. The RNAi of any one of embodiments 1-5, wherein the first strand and the second strand are linked by means of a RNA linker capable of forming a loop structure.

7. The RNAi of embodiment 6, wherein the RNA linker comprises from 4 to 50 nucleotides.

8. The RNAi of embodiment 6 or 7, wherein the loop structure comprises 4 to 20 nucleotides.

9. The RNAi of any one of embodiments 6-8, wherein the RNAi comprises 5' to 3' the second strand, the RNA linker, and the first strand.

10. The RNAi of any one of embodiments 6-8, wherein the RNAi comprises 5' to 3' the first strand, the RNA linker, and the second strand.

11. The RNAi of embodiment 10, wherein the RNAi comprises the nucleic acid sequence of SEQ ID NO:61 or SEQ ID NO:63.

12. The RNAi of embodiment 11, wherein the RNAi comprises a nucleotide sequence about 90% identical to the nucleotide sequence of SEQ ID NO: 61 or SEQ ID NO:63.

13. The RNAi of any one of embodiments 1-12, wherein the RNAi is a small inhibitory RNA (siRNA), a microRNA (miRNA), or a small hairpin RNA (shRNA).

14. The RNAi of any one of embodiments 1-13, wherein the RNAi targets RNA encoding a polypeptide associated with a neurodegenerative synucleinopathy.

15. The RNAi of embodiment 14, wherein the polypeptide is alpha-synuclein (SNCA).

16. The RNAi of embodiment 15, wherein the alpha synuclein is human alpha-synuclein.

17. The RNAi of any one of embodiments 14-16, wherein the neurodegenerative synucleinopathy is Parkinson's disease (PD), multiple system atropy (MSA), or dementia with Lewy bodies (DLB).

18. An expression construct comprising nucleic acid encoding the RNAi of any one of embodiments 1-17.

19. The expression construct of embodiment 18 wherein the nucleic acid encoding the RNAi comprises a miRNA scaffold.

20. The expression construct of embodiment 18 or 19, wherein the nucleic acid encoding the RNAi is operably linked to a promoter.

21. The expression construct of embodiment 20, wherein the promoter is selected from a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a 13-actin promoter.

22. The expression construct of any one of embodiments 18-21, wherein the expression construct further comprises an intron.

23. The expression construct of embodiment 22, wherein the intron is a CBA intron or an hEF1alpha intron.

24. The expression construct of embodiment 22, wherein the intron is a chimeric intron.

25. The expression construct of embodiment 22, wherein the expression vector is a self-complementary vector and the intron is a delta chimeric intron.

26. The expression construct of any one of embodiments 18-25, wherein the expression construct further comprises a polyadenylation signal.

27. The expression construct of embodiment 26 wherein the polyadenylation signal is a bovine growth hormone polyadenylation signal, an SV40 polyadenylation signal, or a HSV TK polyadenylation signal.

28. A vector comprising the expression construct of any one of embodiments 18-27.

29. The vector of embodiment 28, wherein the vector is a recombinant adeno-associated virus (rAAV) vector.

30. The rAAV vector of embodiment 29, wherein the expression construct is flanked by one or more AAV inverted terminal repeat (ITR) sequences.

31. The rAAV vector of embodiment 30, wherein the expression construct is flanked by two AAV ITRs.

32. The rAAV vector of embodiment 30 or 31, wherein the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs.

33. The rAAV vector of any one of embodiments 30-32, wherein the AAV ITRs are AAV2 ITRs.

34. The rAAV vector of any one of embodiments 30-33, wherein the vector further comprises a stuffer nucleic acid.

35. The rAAV vector of embodiment 34, wherein the stuffer nucleic acid is located upstream or downstream of the nucleic acid encoding the RNAi.

36. The rAAV vector of any one of embodiments 30-35, wherein the vector is a self-complementary rAAV vector.

37. The rAAV vector of embodiment 36, wherein the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length.

38. The rAAV vector of embodiment 37, wherein the first nucleic acid sequence and the second nucleic acid sequence are linked by a mutated AAV ITR, wherein the mutated AAV ITR comprises a deletion of the D region and comprises a mutation of the terminal resolution sequence.

39. A cell comprising the rAAV vector of any one of embodiments 29-38.

40. A recombinant AAV particle comprising the rAAV vector of any one of embodiments 29-38.

41. The rAAV particle of embodiment 40, wherein the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, AAV2-HBKO, AAVDJ8, AAVPHP.B, AAVPHP.eB, AAVBR1, AAVHSC15, AAVHSC17, a goat AAV, AAV1/AAV2 chimeric, bovine AAV, or mouse AAV capsid rAAV2/HBoV1 serotype capsid.

42. The rAAV particle of embodiment 40 or 41, wherein the ITR and the capsid of the rAAV viral particle are derived from the same AAV serotype.

43. The rAAV particle of embodiment 40 or 41, wherein the ITR and the capsid of the rAAV viral particle are derived from different AAV serotypes.

44. The rAAV particle of embodiment 43, wherein the ITR is derived from AAV2 and the capsid of the rAAV particle is derived from AAV1.

45. A composition comprising the rAAV particle of any one of embodiments 40-44.

46. The composition of embodiment 45, wherein the composition further comprises a pharmaceutically acceptable carrier.

47. A kit comprising the RNAi of any one of embodiments 1-17.

48. A kit comprising the AAV particle of any one of embodiments 40-44.

49. A kit comprising the composition of embodiment 45 or 46.

50. The kit of any one of embodiments 47-49, further comprising instructions for use.

51. A method for treating a neurodegenerative synucleinopathy in a mammal comprising administering to the mammal an RNAi comprising a first strand comprising a first nucleic acid having at least about 90% identity to the sequence 5'-UGCUCUUUGGUCUUCUCAGCC-3' (SEQ ID NO:24) or a first strand comprising a first nucleic acid having at least about 90% identity to the sequence 5'-UGGGCACAUUGGAACUGAGCA-3' (SEQ ID NO:8), and a second strand comprising a second nucleic acid.

52. The method of embodiment 51, wherein the second nucleic acid comprises nucleic acid having at least about 90% identity to the sequence the sequence 5'-GGCUGAGAACCAAAGAGUA-3' (SEQ ID NO:53) or nucleic acid having at least about 90% identity to the sequence 5'-E1passenger-3' (SEQ ID NO:37).

53. A method for treating a neurodegenerative synucleinopathy in a mammal comprising administering to the mammal an RNAi comprising a first strand comprising a first nucleic acid having at least about 90% identity to the sequence 5'-UGCUCUUUGGUCUUCUCAGCC-3' (SEQ ID NO:24) and a second strand comprising a second nucleic acid having at least about 90% identity to the sequence 5'-GGCUGAGAACCAAAGAGUA-3' (SEQ ID NO:53) or a first strand comprising a first nucleic acid having at least about 90% identity to the sequence 5'-UGGGCACAUUG-GAACUGAGCA-3' (SEQ ID NO:8) and a second strand comprising a second nucleic acid having at least about 90% identity to the sequence 5'-UGCUCAGUCAAUGUGC-CUA-3' (SEQ ID NO:37).

54. A method for inhibiting the expression of alpha-synuclein in a mammal with a neurodegenerative disease comprising administering to the mammal an RNAi comprising a first strand comprising a first nucleic acid having at least about 90% identity to the sequence 5'-UGCUCUUUG-GUCUUCUCAGCC-3' (SEQ ID NO:24) or a first strand comprising a nucleic acid having at least about 90% identity to the sequence 5'-UGGGCACAUUGGAACUGAGCA-3' (SEQ ID NO:8), and a second strand comprising a second nucleic acid.

55. The method of embodiment 54, wherein the second nucleic acid comprises nucleic acid having at least about 90% identity to the sequence 5'-GGCUGAGAAC-CAAAGAGUA-3' (SEQ ID NO:53) or nucleic acid having at least about 90% identity to the sequence 5'-UGCUCA-GUCAAUGUGCCUA-3' (SEQ ID NO:37).

56. A method for inhibiting the expression of alpha-synuclein in a mammal with a neurodegenerative disease comprising administering to the mammal an RNAi comprising a first strand comprising a first nucleic acid having at least about 90% identity to the sequence 5'-UGCUCUUUG-GUCUUCUCAGCC-3' (SEQ ID NO:24) and a second strand comprising a second nucleic acid having at least about 90% identity to the sequence 5'-GGCUGAGAAC-CAAAGAGUA-3' (SEQ ID NO:53) or a first strand comprising a first nucleic acid having at least about 90% identity to the sequence 5'-UGGGCACAUUGGAACUGAGCA-3' (SEQ ID NO:8) and a second strand comprising a second nucleic acid having at least about 90% identity to the sequence 5'-UGCUCAGUCAAUGUGCCUA-3' (SEQ ID NO:37).

57. The method of any one of embodiments 51-56, wherein the first strand comprises the nucleic acid sequence having the sequence of SEQ ID NO:24 or nucleic acid having the sequence of SEQ ID NO:8.

58. The method of any one of embodiments 52, 53, 55, or 56, wherein the second strand comprises the nucleic acid having the sequence of SEQ ID NO:53 or the nucleic acid having the sequence of SEQ ID NO:37.

59. The method of any one of embodiments 51-58, wherein the first strand and the second strand are linked by means of a RNA linker capable of forming a loop structure.

60. The method of embodiment 59, wherein the RNA linker comprises from 4 to 50 nucleotides.

61. The method of embodiment 59 or 60, wherein the loop structure comprises 4 to 20 nucleotides.

62. The method of any one of embodiments 59-61, wherein the RNAi comprises 5' to 3' the second strand, the RNA linker, and the first strand.

63. The method of any one of embodiments 59-61, wherein the RNAi comprises 5' to 3' the first strand, the RNA linker, and the second strand.

64. The method of embodiment 63, wherein the RNAi comprises the nucleic acid sequence of SEQ ID NO:61 or SEQ ID NO:63.

65. The method of embodiment 64, wherein the RNAi comprises a nucleotide sequence about 90% identical to the nucleotide sequence of SEQ ID NO:61 or SEQ ID NO:63.

66. The method of any one of embodiments 51-65, wherein the RNAi is encoded on an expression construct.

67. The method of any one of embodiments 51-66, wherein the nucleic acid encoding the RNAi comprises a miRNA scaffold.

68. The method of any one of embodiments 51-67, wherein the nucleic acid encoding the RNAi is operably linked to a promoter.

69. The method of embodiment 68, wherein the promoter is capable of expressing the RNAi in the brain of a mammal.

70. The method of embodiment 69, wherein the promoter is selected from a cytomegalovirus (CMV) immediate early promoter, a RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), a E2F promoter, a telomerase (hTERT) promoter; a cytomegalovirus enhancer/chicken beta-actin/Rabbit β-globin (CAG) promoter, an elongation factor 1-alpha promoter (EF1-alpha) promoter and a human β-glucuronidase promoter.

71. The method of any one of embodiments 68-70, wherein the promoter is a hybrid chicken β-actin promoter (CBA) comprising a CMV enhancer and a chicken β-actin promoter.

72. The method of any one of embodiments 66-71, wherein the expression construct further comprises an intron.

73. The method of embodiment 72, wherein the intron is a CBA intron.

74. The method of embodiment 72, wherein the intron is a chimeric intron.

75. The method of embodiment 74, wherein the expression construct is a self-complementary vector and the intron is a delta chimeric intron.

76. The method of any one of embodiments 66-75, wherein the nucleic acid further comprises a polyadenylation signal.

77. The method of embodiment 76, wherein the polyadenylation signal is a bovine growth hormone polyadenylation signal.

78. The method of any one of embodiments 66-77, wherein the expression construct is encoded by a vector.

79. The method of embodiment 78, wherein the vector is a recombinant adeno-associated virus (rAAV) vector.

80. The method of embodiment 79, wherein the expression construct is flanked by one or more AAV inverted terminal repeat (ITR) sequences.

81. The method of embodiment 80, wherein the expression construct is flanked by two AAV ITRs.

82. The method of embodiment 80 or 81, wherein the AAV ITRs are AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs.

83. The method of any one of embodiments 80-82, wherein the AAV ITRs are AAV2 ITRs.

84. The method of embodiment 83, wherein the rAAV vector comprises 5' to 3' an AAV2 ITR, a promoter, an intron, nucleic acid encoding the RNAi, a polyadenylation signal, and an AAV2 ITR.

85. The method of embodiment 84, wherein the promoter is a CBA promoter.

86. The method of embodiment 84, wherein the intron is a chimeric intron, a delta chimeric intron or an abbreviated chimeric intron chimeric.

87. The method of embodiment 86, wherein the chimeric intron is a CBA+rabbit beta globin intron.

88. The method of any one of embodiments 84-87, wherein the polyadenylation signal is a bovine growth hormone polyadenylation signal.

89. The method of embodiment 83, wherein the rAAV vector comprises 5' to 3' an AAV2 ITR, the CBA promoter, a chimeric intron, nucleic acid encoding the RNAi, a bovine growth hormone polyadenylation signal, and an AAV2 ITR.

90. The method of embodiment 89, wherein the vector further comprise a stuffer nucleic acid.

91. The method of embodiment 90, wherein the stuffer nucleic acid comprises intron 1 of the human A1AT gene.

92. The method of any one of embodiments 79-91, wherein the vector is a self-complementary vector.

93. The method of embodiment 92, wherein the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length.

94. The method of embodiment 93, wherein the first nucleic acid sequence and the second nucleic acid sequence are linked by a mutated AAV ITR, wherein the mutated AAV ITR comprises a deletion of the D region and comprises a mutation of the terminal resolution sequence.

95. The method of any one of embodiments 79-94, wherein the vector is encapsidated in a rAAV particle.

96. The method of embodiment 95, wherein the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV2 V708K, AAV2-HBKO, AAVDJ8, AAVPHP.B, AAVPHP.eB, AAVBR1, AAVHSC15, AAVHSC17, goat AAV, AAV1/AAV2 chimeric, bovine AAV, mouse AAV, or rAAV2/HBoV1 serotype capsid.

97. The method of embodiment 95 or 96, wherein the ITR and the capsid of the rAAV viral particle are derived from the same AAV serotype.

98. The method of embodiment 95 or 96, wherein the ITR and the capsid of the rAAV viral particles are derived from different AAV serotypes.

99. The method of any one of embodiments 95-98, wherein the rAAV viral particle comprises AAV2 capsid.

100. The method of embodiment 99, wherein the rAAV viral particle comprises an AAV1 capsid, and wherein the vector comprises AAV2 ITRs.

101. A method of any one of embodiments 51-100, wherein the rAAV particle of any one of embodiments 95-100 is in a composition.

102. The method of embodiment 101, wherein the composition further comprises a pharmaceutically acceptable carrier.

EXAMPLES

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: shmiRNA Reduces Human SNCA Target In Vitro

To demonstrate reduction of SNCA expression in vitro, HEK293T cells were transfected with plasmids encoding candidate RNAi sequences and a plasmid encoding the human SNCA cDNA A (NM_000345.3) under the control of a cytomegalovirus enhancer and hEF1a promoter/intron and followed by a Tbgh polyA sequence. SNCA cDNA and miRNA plasmids were co-transfected.

Methods siRNAs and Plasmids

RNAi sequences were designed internally to have maximum homology to human/macaque/mouse SNCA, while balancing this with low-off targeting potential. Conventional siRNAs were synthesized by Sigma. Off targets in the human transcriptome were predicted using the siSPOTR algorithm (world wide web at https://sispotr.icts.uiowa.edu/sispotr/tools.html).

Plasmids expressing RNAi sequences targeting SNCA were embedded within the murine mir155 scaffold driven by a cytomegalovirus enhancer and hEF1a promoter/intron. RNAi sequences can be found in Table 1.

In Vitro Cell Culture and Transfections

HEK293T cells were grown to ~70-90% confluency in DMEM+10% FBS+pen/strep. Cells were transfected with Lipfectamine 2000 (for miRNA format plasmids) or RNAiMAX (for siRNA format). Three days post-transfection, cells were rinsed with phosphate buffered saline, whole cell extracts were prepared by cell lysis in reducing Laemmli buffer and were boiled for 5 minutes before storage at −20° C.

Western Blotting and Densitometry

Cell lysates were run on 4-12% SDS-PAGE (Bio-Rad TGX™). Proteins were transferred to nitrocellulose (Bio-Rad Transblot®), blocked in 5% nonfat milk, and incubated with primary antibodies overnight at 4° C. Primary antibodies were washed off, incubated with HRP-tagged secondary antibody, and HRP activity was detected using Femto ECL substrate (Bio-Rad) and imaged on a Bio-Rad GelDoc™ imager. Bands were quantified using ImageJ software (NIH). Alpha-synuclein protein levels were normalized to GAPDH or beta-tubulin to control for protein loading. Antibodies used: Alpha-synuclein (BD 610787), GAPDH (Sigma G8795), Tubulin (BioLegend MMS-435P-100). HRP-goat anti-mouse or rabbit (CST 7076).

Results

As shown in FIG. 2, shmiRNAs reduced human SNCA protein levels in vitro. With 19/27 sequences showing more than 50% reduction in protein levels.

Example 2: shmiRNA Reduces Mouse SNCA Target In Vitro

Figure 3:
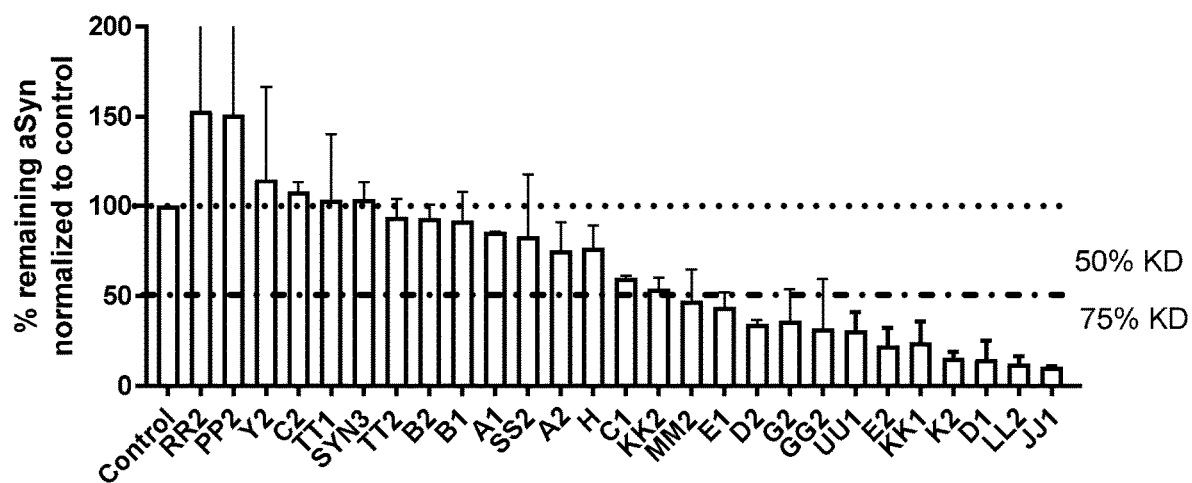
FIG. 3 shows RNAi-mediated reduction of mouse SNCA in vitro. Quantification of SNCA in whole cell extracts of HEK293T cells 72 hours post-transfection with plasmids encoding the indicated RNAi sequences in miRNA format and mouse SNCA cDNA. SNCA levels were normalized to GAPDH loading control, and normalized to control (non-targeting control RNAi) to calculate percent knockdown.

Analogous methods were used in this experiment as in Example 1 with the exception that HEK293T cells were transfected with plasmids encoding the indicated RNAi sequences and mouse SNCA cDNA Results As shown in FIG. 3, the indicated miRNAs reduced mouse SNCA protein levels in vitro with 14/27 sequences showing greater than 50% reduction in protein levels.

Example 3: siRNA Reduces Human and Mouse SNCA Target In Vitro

Additional experiments using the siRNA format were performed for A1, A2, B1, B2, C1, C2, D1, D2, E1 and E2 to provide additional data on target reduction because these were designed with the added feature of having complete, or significant, homology to rat SNCA which enables flexibility in choosing future animal models of neurodegeneration that may require rat SNCA reduction.

Methods

In Vitro Cell Culture and Transfections

HEK293T cells were grown to ~70-90% confluency in DMEM+10% FBS+pen/step. Cells were transfected with Lipfectamine 2000 (for miRNA format plasmids) or RNAiMAX (for siRNA format). Three days post-transfection, cells were rinsed with phosphate buffered saline, whole cell extracts were prepared by cell lysis in reducing Laemmli buffer and were boiled for 5 minutes before storage at −20° C.

Western Blotting and Densitometry

Cell lysates were run on 4-12% SDS-PAGE (Bio-Rad TGX™). Proteins were transferred to nitrocellulose (Bio-Rad Transblot®), blocked in 5% nonfat milk, and incubated with primary antibodies overnight at 4C. Primary antibodies were washed off, incubated with HRP-tagged secondary, and HRP activity was detected using Femto ECL substrate (Bio-Rad) and imaged on a Bio-Rad GelDoc™ imager. Bands were quantified using ImageJ software (NIH). Alpha-synuclein protein levels were normalized to GAPDH or beta-tubulin to control for protein loading. Antibodies used: Alpha-synuclein (BD 610787), GAPDH (Sigma G8795), Tubulin (BioLegend MMS-435P-100). HRP-goat anti-mouse or rabbit (CST 7076).

Results

As shown in FIGS. 4A-4D, the indicated siRNAs reduced human and mouse SNCA levels in vitro as would be expected based on their performance in the miRNA format.

Example 4: Toxicity and Neuroprotection Properties of RNAi Indicated

The toxicity and neuroprotection properties of candidate shmiRNAs were evaluated using Lund human mesencephalic (LUHMES) cells differentiated to mature dopamine-like neurons (10).

Methods

In Vitro Cell Culture and Transfections

LUHMES cells (ATCC CRL-2927) cells were grown and differentiated as described in (10) with some modifications to allow for electroporation of plasmid DNA. Briefly, LUHMES cells were subcultured in proliferation media (10) on flasks coated with poly-L-ornithine and fibronectin. Differentiation into dopaminergic cells was initiated by the addition differentiation media (10). Cells were dissociated 2 days later, electroporated (LONZA 4D Nucleofector™ X system according to the manufacturer's instructions) with the desired DNA, and replated in 96 well plates in recovery media to minimize electroporation toxicity. 4 hours post transfection, media was changed back to differentiation media. Cells were treated and collected at the indicated days post-transfection for specific experiments.

In Vitro Neuroprotection Assay

LUHMES cells prepared as above were treated with the indicated concentrations of rotenone at day 6 of differentiation (day 4 of transfection). Cell viability was measured using the Cell Titer Blue® assay as per manufacturer's instructions (Promega) 48 hours following treatment with rotenone. Reactive oxygen species (ROS) production was measured via the DCFDA kit (Abcam) 24 hours following treatment. Values were normalized to untreated, Control transfected cells.

Statistical Analysis

Data from the cell viability experiments were compiled to rank % SNCA mRNA knockdown using D1 and E1 sequences against % neuroprotection against rotenone induced toxicity. Percent SNCA knockdown was significantly correlated with the degree of neuroprotection, as calculated using Graphpad Prism® (v6).

Results

Figure 5A:
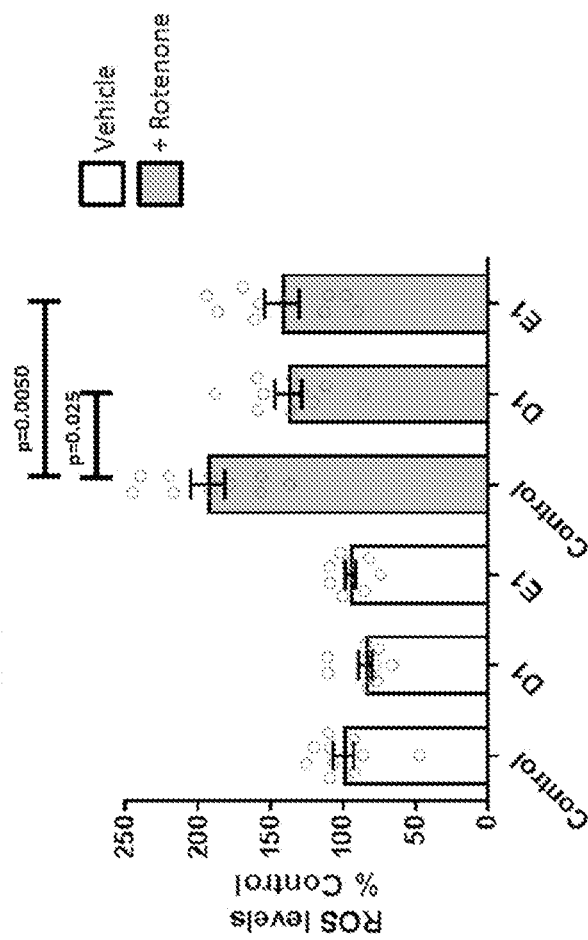
FIGS. 5A-B shows the toxicity of indicated RNAi sequences in transfected LUHMES cells. LUHMES cells were transfected with the indicated RNAi sequences in miRNA format, and then treated with rotenone to induce cell toxicity.
Figure 5B:
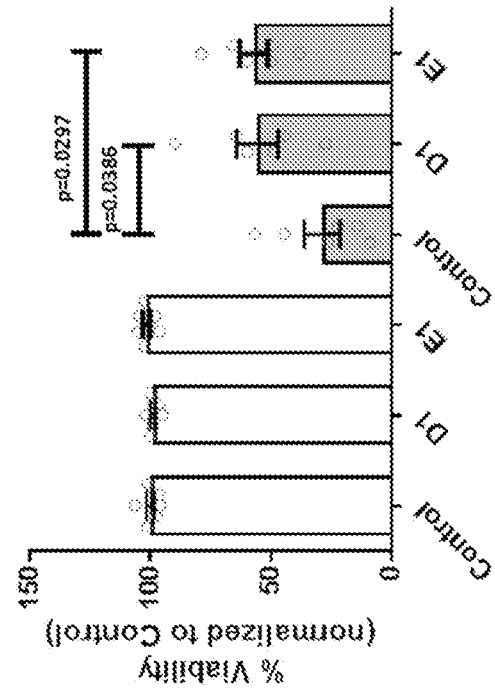

As shown in FIGS. 5A and 5B, SNCA knockdown is not toxic on its own, and significantly protects against cell death (FIG. 5A) and lowers rotenone-dependent ROS production (FIG. 5B). Control, D1 and E1 sequences did not alter cell viability on their own. Rotenone treatment of Control transfected cells resulted in ~75% cell death, but transfection with SNCA knockdown vectors significantly protected against this toxicity.

Figure 6:
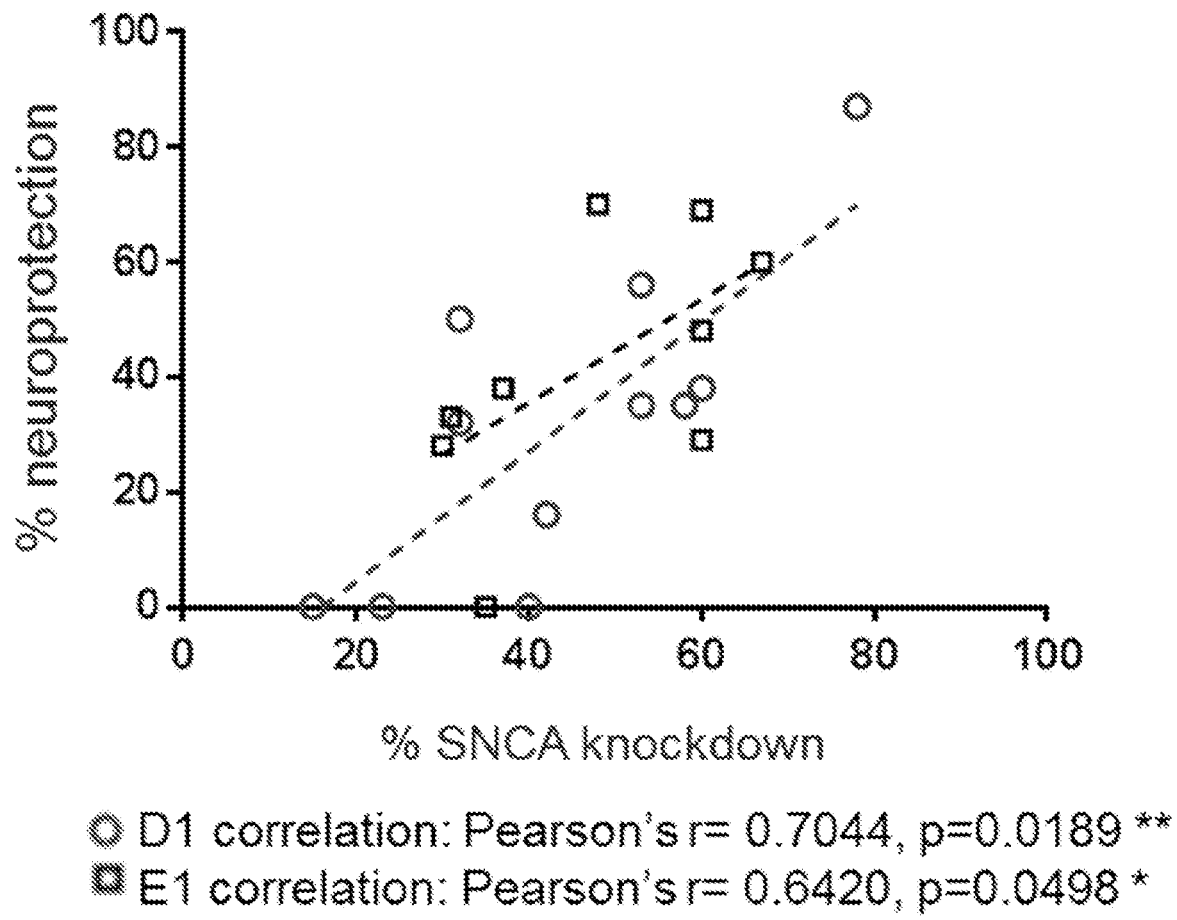
FIG. 6 shows the positive correlation of SNCA knockdown with neuroprotection. Percent neuroprotection (as cell viability) from FIG. 5 were plotted vs the level of knockdown from D1 or E1 in each respective experiment. Both RNAi sequences showed significant, positive correlation (Pearson's) of percent knockdown with the level of neuroprotection in rotenone-treated LUHMES cells.

As shown in FIG. 6, data from the cell viability experiments were compiled to rank % SNCA mRNA knockdown using D1 and E1 sequences vs percent neuroprotection against rotenone induced toxicity. The degree of SNCA knockdown was significantly positively correlated with the degree of neuroprotection demonstrating that reduction of SNCA mRNA using D1 and E1 sequences is a valid neuroprotection strategy.

Example 5: In Vivo Target Knockdown by D1 and E1 Vectors

To determine in vivo knockdown of SNCA, AAV vectors encoding D1, E1 or control RNAi sequences were injected into the SNc of wild type mice. SNc tissue was collected 1 month post-injection. RNA was isolated and levels of SNCA mRNA quantified via Taqman qPCR. Relative levels of transcript were normalized to GAPDH.

Methods

Viral Vectors

To generate rAAV viruses for in vivo testing, the mir155 cassette was cloned into an AAV2 ITR plasmid containing the 1.6 kb CAG promoter for AAV virus production using a modified AAV2HBKO capsid (WO 2015168666 A2). All viral vectors were produced by the triple-transfection method in 293 cells, and purified as described (11). Titers were determined via qPCR and are expressed as genome copies (GC)/mL or as total vector genomes (vg)

Animals

Male C57BL/6J mice (10-12 weeks of age) were purchased from Charles River Laboratories, France. Animals were housed in group of four in each cage with free access to food and water, with controlled room temperature, humidity and under a 12:12 h light/dark cycle.

Stereotaxic Injection

Mice were deeply anesthetized with an intraperitoneal injection of mixture (volume 10 mL/Kg): ketamine (100 mg/kg; Imalgene®; Merial, France) and xylazine (10 mg/Kg; Rompun®; Bayer, France). Before positioned the animal in the stereotaxic frame (Kopf Instruments, USA), the mouse scalp was shaved and disinfected with Vetidine (Vetoquinol® France), a local anesthetic bupivacaine (2 mg/kg at a volume of 5 ml/kg; Aguettant, France) was injected subcutaneously on the skin of the skull and Em1a (Lidocaïne, Astrazeneca) was applied into the ears. During surgery, the eyes were protected from light by vitamin A Dulcis and the body temperature was kept constant at 37° C. by a heating blanket.

A small hole was made in the skull-bone above the injection coordinate. A cannula 33 gauge (OD 0.254 mm; Phymep), connected with flexible Plastic tubing to a syringe of 25 µL, which is in turn is connected to a microperfusion pump, was inserted unilaterally into the left substantia nigra pars compacta (SNpc) at the following coordinates: AP=−2.92 mm from bregma; ML=1.25 mm; DV:−4.5 mm from dura, according to the mouse atlas of Paxinos and Watson (2008). After randomization, the mice (n=10/group) were injected with AAV. Infusion was performed at a rate of 0.2 µL/min and a final volume of 1 µL was injected.

After the final injection, the cannula was maintained in the SNpc for an additional 5 min to avoid backflow. It was then slowly removed from the mouse brain and the scalp was closed by suturing. Mice were monitored daily and after surgery they received subcutaneous injection of carprofen (5 mg/kg sc; volume 5 ml/kg; Rimadyl®, Zoetis) and intraperitoneal injection of about 200 µL of sterile saline to prevent dehydration. The animals are then placed in Medi-Heat® Warming Cabinet until they are completely awake. One-month post injection, the animals were anesthetized with isoflurane 4% and the brains were processed for immunohistochemical and biochemical analysis. All the experiments have been done in blind.

Statistical Analysis

Statistics were performed using Prism software (Version 6, Graphpad®) using one-way ANOVA, with multiple comparisons (Dunnett's test) when applicable.

Results

Figure 7:
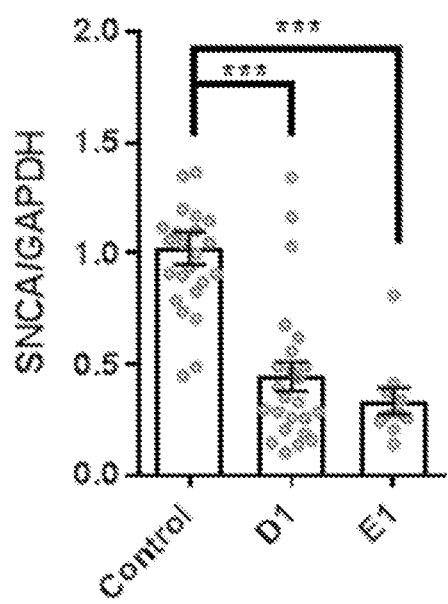
FIG. 7 shows target mRNA knockdown by indicated RNAi in miRNA format in vivo. Bars indicate the mean+/− SEM. Circles represent individual animals. Significance assessed via one-way ANOVA with multiple comparisons.

As shown in FIG. 7, D1 and E1 vectors showed 55% and 66% knockdown of SNCA mRNA, respectively, relative to Control RNAi demonstrating significant target mRNA knockdown in vivo in the target structure using AAV-mediated delivery of SNCA-targeting miRNA.

Figure 8:
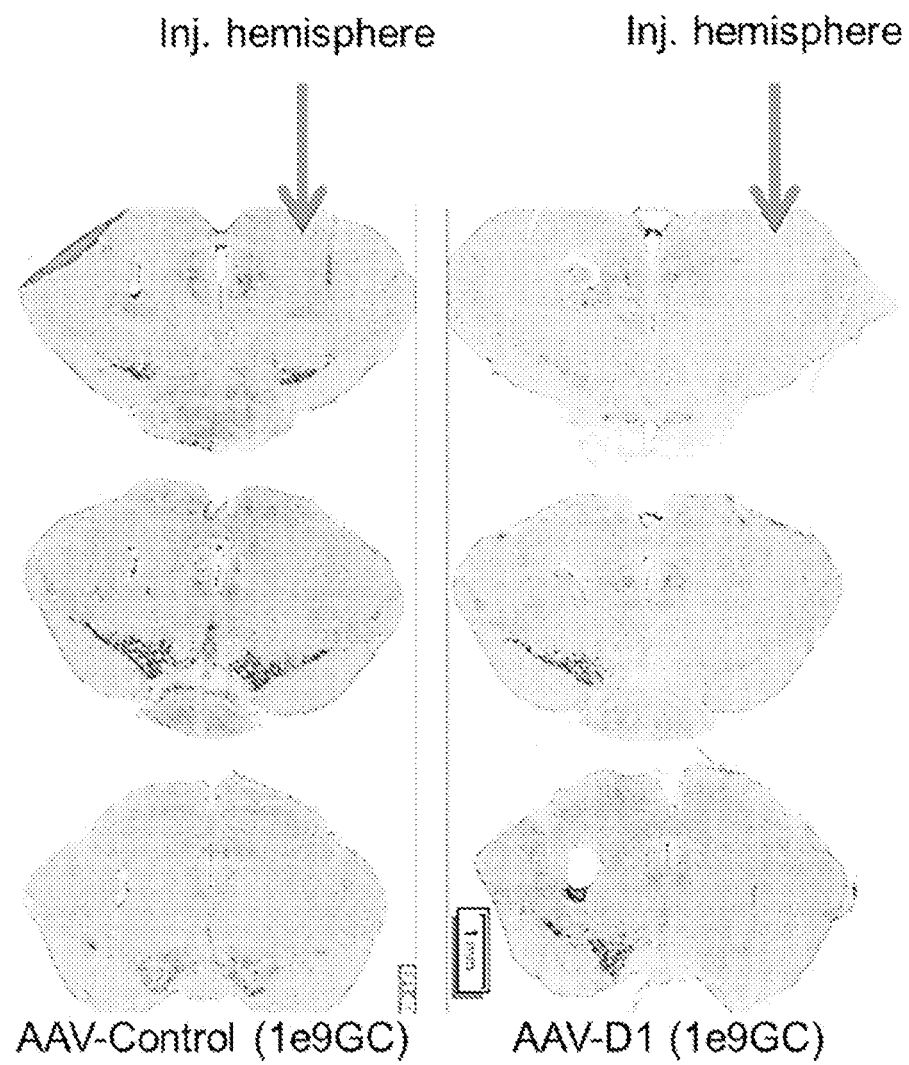
FIG. 8 shows reduction of SNCA mRNA throughout the midbrain in mice after injection of AAV-D1 vector. Mice were injected unilaterally with 1e10 GC control or D1 virus. Tissue was collected and processed for in situ hybridization 1 month later. The SNCA anti-sense probe clearly shows target reduction at three different anatomical levels rostal to caudal relative to the contralateral hemisphere. The control RNAi virus did not show any decrease in SNCA mRNA relative to the uninjected hemisphere.
Figure 9:
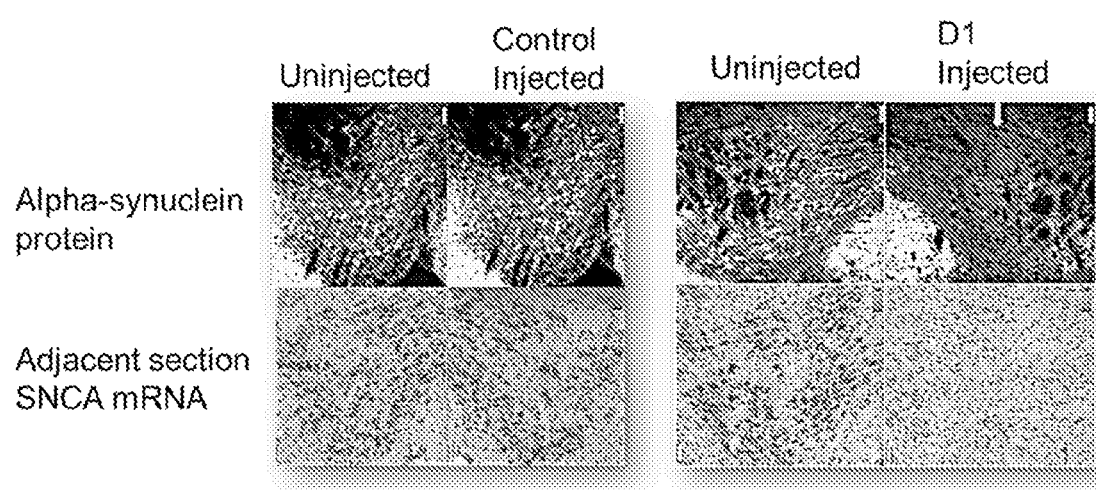
FIG. 9 shows reduction of SNCA protein and mRNA in mice via SNc immunohistochemistry and in situ hybridization.

As shown in FIG. 8, The SNCA anti-sense probe clearly shows target reduction at three different anatomical levels rostal to caudal relative to the contralateral hemisphere. The control RNAi virus did not show any decrease in SNCA mRNA relative to the uninjected hemisphere demonstrating the specificity of the effect. As shown in FIG. 9, alpha-synuclein protein signal in the VTA needed to be saturated to observe somal synuclein expression, precluding any determination of SNCA reduction in that brain region.

Example 6: AAV-D1 Vector Reduces SNCA mRNA in Mice by SNc Immunohistochemistry

Mice were injected unilaterally with 1e9 GC of Control or D1 AAV vector as described in Example 5. Tissue was collected and coronal sections were processed for immunohistochemistry (IHC) one month later to assess alpha-synuclein protein levels in the substantia nigra pars *compacta*.

Additional Methods

Immunohistochemistry and ISH

Brains were immersion-fixed in 4% formaldehyde for at least 2 days at 4° C. and cryopreserved in 30% sucrose solution, then frozen. Frozen brains were cut into serial coronal sections along the entire antero-posterior axis of the substantia nigra (sn). Sections were placed in pbs-0.4% sodium azide and stored at 4° C.

Randomly selected series of 20 µm-thick free-floating sections were used to perform immunolabelling with primary mouse monoclonal antibody against α-syn (mouse monoclonal, 1:2000, clone 42, BD transductions laboratories). This antibody can detect endogenous levels of mouse α-syn protein predominantly with localization at synaptic membranes but also within da neuronal cell bodies of ventral tegmental area (VTA) and SN.

Sections were rinsed 3 times in 0.1m pbs-0.15% triton, 0.2% gelatin from bovine skin (Sigma, G9391) solution and pretreated in blocking buffer (i.e., 0.1m PBS-10% albumin from bovine serum, Sigma, A8022) for 30 min. They were then incubated overnight with primary antibody solution in 0.1m PBS at room temperature. After rinsing in 0.1m PBS-0.15% triton, 0.2% gelatin, fluorochome-conjugated antibody (goat anti-mouse 647, Abcam 150119) was used as secondary antibody (1:400 in 0.1m PBS, 90 min incubation in the dark, room temperature). Sections were rinsed 2 times in 0.1m PBS-0.2% gelatin solution, 1 time in PBS 0.1m and mounted (flex slides, Dako). Sections were coverslipped with prolong gold antifade reagent (Invitrogen p36931).

Qualitative image analysis of fluorescent immunolabelling was performed on a slide scanner system (Olympus DotSlide system equipped with a BX61 microscope with fluorescence capability).

Results

As shown in FIG. 9, compared to the contralateral SNc of the same animal or Control injected animal, SNCA protein in the cell body is clearly reduced by D1. ISH images from adjacent brain sections (bottom panels, processed as per example 5) show the parallel reduction in SNCA mRNA by the D1 RNAi vector but not Control vector. These data demonstrate the AAV-delivery of miRNAs targeting SNCA show durable mRNA knockdown in the desired brain region.

Example 7: In Vivo Target Knockdown by E1 in the Vector AAVrh.10

To determine in vivo knockdown of SNCA and demonstrate that the knockdown of the SNCA is not dependent of the AAV serotype, AAV.rh10 vectors encoding E1 or control RNAi sequences were injected into the SNc of wild type mice. Mice were injected unilaterally with 10e9 GC of Control or AAV.rh10 E1 vector as described previously. SNc tissue was collected 1 month post-injection. SNCA mRNA expression was quantified by In Situ Hybridization and SNCA protein was detected by Immunohistochemistry Methods Viral Vectors To generate rAAV viruses for in vivo testing, the mir155 cassette was cloned into an AAV2 ITR plasmid containing the 1.6 kb CAG promoter for AAV virus production using a the capsid of an rh. 10 serotype of AAV (Gao, G. P. et al., 2002, *Proc. Natl. Acad. Sci. USA* 99:11854-11859.). All viral vectors were produced by the triple-transfection method in 293 cells, and purified as described (11). Titers were determined via qPCR and are expressed as genome copies (GC)/mL or as total vector genomes (vg).

Animals

Male C57BL/6J mice (10-12 weeks of age) were purchased from Charles River Laboratories, France. Animals were housed in group of four in each cage with free access to food and water, with controlled room temperature, humidity and under a 12:12 h light/dark cycle.

Stereotaxic Injection

Mice were deeply anesthetized with an intraperitoneal injection of mixture (volume 10 mL/Kg): ketamine (100 mg/kg; Imalgene®; Merial, France) and xylazine (10 mg/Kg; Rompun®; Bayer, France). Before positioned the animal in the stereotaxic frame (Kopf Instruments, USA), the mouse scalp was shaved and disinfected with Vetidine (Vetoquinol®, France), a local anesthetic bupivacaine (2 mg/kg at a volume of 5 ml/kg; Aguettant, France) was injected subcutaneously on the skin of the skull and Emla (Lidocaïne, Astrazeneca) was applied into the ears. During surgery, the eyes were protected from light by vitamin A *Dulcis* and the body temperature was kept constant at 37° C. by a heating blanket.

A small hole was made in the skull-bone above the injection coordinate. A cannula 33 gauge (OD 0.254 mm; Phymep), connected with flexible Plastic tubing (Tygon 0.254*0.762, ref.AAD04091) to a syringe of 25 µL (Exmire, ref.MS*GF25), which is in turn is connected to a microperfusion pump (CMA 4004), was inserted unilaterally into the left substantia nigra pars compacta (SNpc) at the following coordinates: AP=−2.92 mm from bregma; ML=1.25 mm;

DV:−4.5 mm from dura, according to the mouse atlas of Paxinos and Watson (2008). After randomization, the mice (n=10/group) were injected with AAV. Infusion was performed at a rate of 0.2 µL/min and a final volume of 1 µL was injected. After the final injection, the cannula was maintained in the SNpc for an additional 5 min to avoid backflow. It was then slowly removed from the mouse brain and the scalp was closed by suturing. Mice were monitored daily and after surgery they received subcutaneous injection of carprofen (5 mg/kg sc; volume 5 ml/kg; Rimadyl, Zoetis) and intraperitoneal injection of about 200 µL of sterile saline to prevent dehydration. The animals are then placed in MediHeat® Warming Cabinet (Peco services) until they are completely awake. One-month post injection, the animals were anesthetized with isoflurane 4% and the brains were processed for immunohistochemical and biochemical analysis. All the experiments have been done in blind.

Immunohistochemistry and ISH

Brains were immersion-fixed in 4% Formaldehyde for at least 2 days at 4° C. and cryopreserved in 30% sucrose solution, then frozen. Frozen brains were cut into serial coronal sections along the entire antero-posterior axis of the substantia nigra (SN). Sections were placed in PBS-0.4% sodium azide and stored at 4° C.

Randomly selected series of 20 µm-thick free-floating sections were used to perform immunolabelling with primary mouse monoclonal antibody against α-Syn (mouse monoclonal, 1:2000, clone 42, BD Transductions laboratories). This antibody can detect endogenous levels of mouse α-Syn protein predominantly with localization at synaptic membranes but also within DA neuronal cell bodies of ventral tegmental area (VTA) and SN.

For enzymatic revelation of α-syn IHC, after incubation in primary antibody solution, sections were incubated at room temperature with Biotinylated mouse IgG (BA 9200 Vector Lot S0913, dilution 1/400) for 90 min and then with peroxidase-coupled avidin complex (Vectastain® ABC kit Elite, Vector PK 6100, dilution 1/200) for 30 min. Sections were briefly incubated in peroxidase substrate solution (containing 0.003% hydrogen peroxide, 0.05% diaminobenzidine tetrahydrochloride in 0.1 M PBS) and finally rinsed in NaCl 0.9% solution. Sections were finally mounted on slides and dried at room temperature, dehydrated and coverslipped using Eukitt.

For α-syn ISH studies, fully automated RNAscope assay (that improve the signal-to-noise ratio of RNA ISH by amplifying target-specific signals but not background noise from nonspecific hybridization).on 20 µm thick cryostat sections mounted over slides was run on Roche Ventana Medical Systems DISCOVERY XT (VS) automate. (RNAscope® 2.5 VS antisense probe-Hs-SNCA (Cat No. 313289) and control sense probe (Cat No.511079) were hybridized for 2 h at 43° C. followed by RNAscope amplification and Red chromogen detection using VS detection reagents. RNAscope probe design as described hereby. Stained slides were scanned with the VS120 Olympus system using the 40× objective.

Statistical Analysis

Statistics were performed using Prism software (Version 6, Graphpad®) using one-way ANOVA, with multiple comparisons (Dunnett's test) when applicable.

Results

Figure 10:
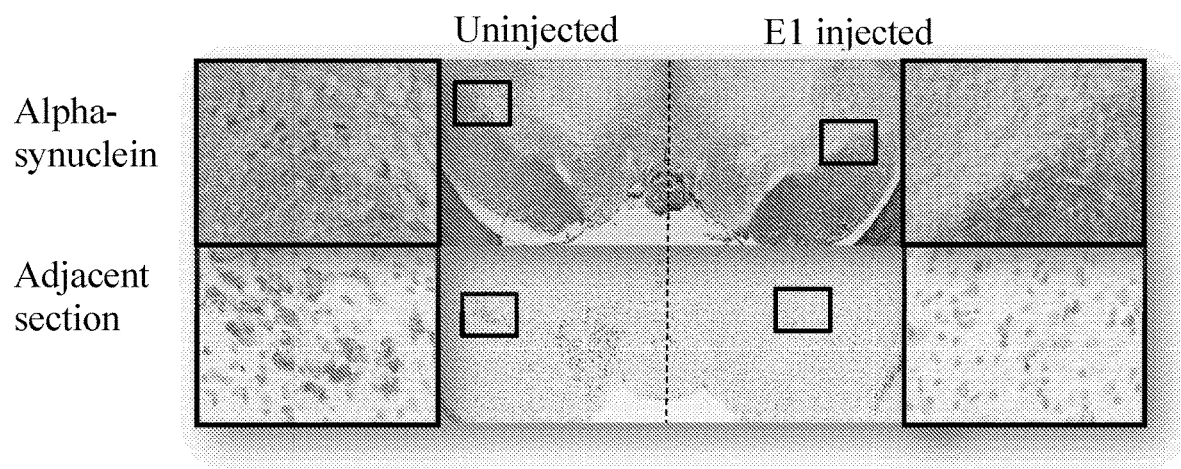
FIG. 10 shows reduction of SNCA protein and mRNA in mice via SNc immunohistochemistry and in situ hybridization following delivery of an AAV.rh10-E1 vector.

As shown in FIG. 10, compared to the contralateral SNc of the same animal or Control injected animal, SNCA protein in the cell bodies is clearly reduced by the construct E1 in AAVrh.10 capsid (upper panel). ISH images from adjacent brain sections (bottom panels) show the parallel target reduction in SNCA mRNA by AAVrh.10 but not in the contralateral hemisphere. The control RNAi virus did not show any decrease in SNCA mRNA relative to the uninjected hemisphere demonstrating the specificity of the effect. Herein it is demonstrated that the efficiency of knock down of SNCA by E1 is not dependent of the serotype of the capsid at least after intranigral injection of the vector.

Example 8: Potential Off-Targets of D1 and E1

Lund Human Mesencephalic (LUHMES) cells were differentiated in culture then transfected with plasmids expressing the D1, E1, or CTL3 (control) microRNA on the optimized murine endogenous miR-155 scaffold (ThermoFisher). Total RNA was isolated from the cells using the miRNeasy® kit (Qiagen), and next-generation sequencing libraries prepared using the TruSeq stranded Total RNA Library Prep kit (Illumina), followed by sequencing on an Illumina HiSeq instrument (Genewiz, Plainfield NJ).

Figure 11:
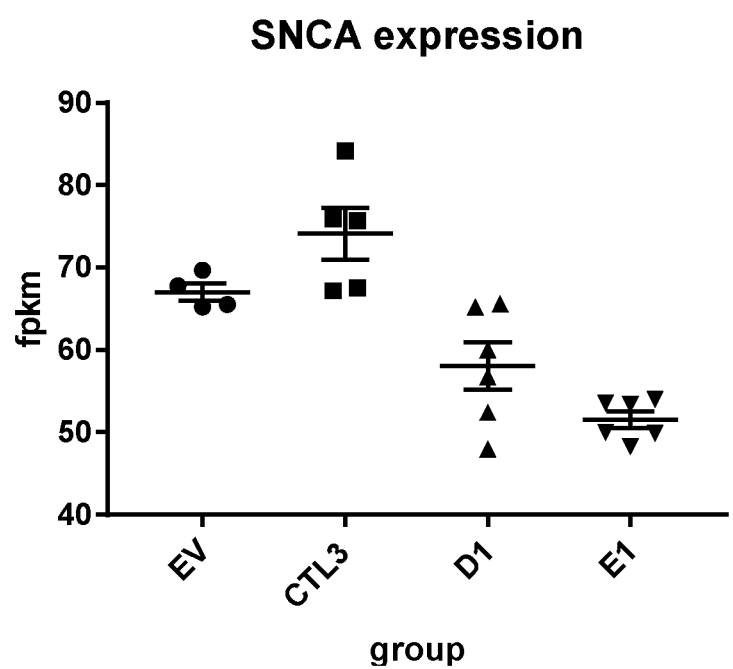
FIG. 11 shows α-synuclein normalized expression in individual biological replicates for each sample group; EV stands for "empty vector".

Sequencing analysis was performed in the Genomics group at Sanofi using Array Studio (Omicsoft, A Qiagen Company). Low quality reads were removed and the remaining reads mapped to the human genome, followed by One-way ANOVA to determine significantly differentially expressed genes (DEGs) among the treatment groups. Genes down-regulated by both D1 and E1 versus CTL3 with p-values less than 0.05 were considered to be consequences of knocking down alpha-Synuclein, and the remaining genes down-regulated by at least 1.2-fold with p-values <0.05 were categorized as potential off-targets. Alpha-Synuclein was knocked down 22% by D1 and 30% by E1 with individual data points shown below in FIG. 11. Potential off-targets for D1 and E1 are listed in Tables 2 and 3. TNFRSF6B on the D1 list is a predicted tumor suppressor in the NCKU database only, and none of the genes in the E1 list are predicted to be tumor suppressors in either the NCKU or TSGene database. Both D1 and E1 lists of potential off-targets were overlapped with predicted targets for the D1 and E1 microRNAs identified using the miRanda, siSPOTR, and TargetRank (data not included) algorithms.

TABLE 2

POTENTIAL D1 OFF-TARGETS

| GeneName | GeneDescription | D1_CTL3_fold | p-value |
|---|---|---|---|
| AC005943.1 | novel transcript, readthrough between UQCR11 and MBD3 | 0.51 | 0.0478 |
| LRRC4B | leucine rich repeat containing 48 | 0.74 | 0.0139 |
| NPIPA7 | nuclear pore complex interacting protein family member A7 | 0.74 | 0.003 |
| SNURF | SNRPN upstream reading frame | 0.75 | 0.0106 |
| ZNFS80 | zinc finger protein 580 | 0.77 | 0.0239 |
| CBWD3 | COBW domain containing 3 | 0.77 | 0.0072 |
| AC092647.5 | novel zinc finger protein 713 (ZNF713) and mitochondrial ribosomal protein S17 (MRPS17) protein | 0.78 | 0.0068 |
| FAM71F2 | family with sequence similarity 71 member F2 | 0.78 | 0.0157 |
| HIST4H4 | histone cluster 4 H4 | 0.79 | 0.0028 |
| RTEL1-TNFRSF6B | RTEL1-TNFRSF68 readthrough (NMD candidate) | 0.80 | 0.0028 |
| PDF | peptide deformylase (mitochondrial) | 0.80 | 0.0423 |
| HAGHL | hydroxyacylglutathione hydrolase-like | 0.82 | 0.0426 |
| KISS1R | KISS1 receptor | 0.82 | 0.0203 |

TABLE 3

POTENTIAL E1 OFF-TARGETS

| GeneName | GeneDescription | E1_CTL3_fold | p-value |
|---|---|---|---|
| AC010616.2 | novel protein, ATP1A3-RABAC1 readthrough | −2.21 | 0.0014 |
| AC117378.1 | novel protein | −1.43 | 0.0362 |
| AL662899,2 | novel protein | −1.28 | 0.0099 |
| NUDCD2 | NudC domain containing 2 | −1.24 | 0.0106 |
| SYNJ2BP-COX16 | SYNJ2BP-COX16 readthrough | −1.23 | 0.0231 |
| AL109811.4 | novel protein | −1.22 | 0.0104 |

REFERENCES

1. S. T. Baek et al., Off-target effect of doublecortin family shRNA on neuronal migration associated with endogenous microRNA dysregulation. *Neuron* 82, 1255-1262 (2014).
2. W. Dauer et al., Resistance of alpha-synuclein null mice to the parkinsonian neurotoxin MPTP. *Proceedings of the National Academy of Sciences of the United States of America* 99, 14524-14529 (2002).
3. R. E. Drolet, B. Behrouz, K. J. Lookingland, J. L. Goudreau, Mice lacking alpha-synuclein have an attenuated loss of striatal dopamine following prolonged chronic MPTP administration. *Neurotoxicology* 25, 761-769 (2004).
4. D. Alvarez-Fischer et al., Characterization of the striatal 6-OHDA model of Parkinson's disease in wild type and alpha-synuclein-deleted mice. *Experimental neurology* 210, 182-193 (2008).
5. P. Klivenyi et al., Mice lacking alpha-synuclein are resistant to mitochondrial toxins. *Neurobiology of disease* 21, 541-548 (2006).
6. S. Mittal et al., beta2-Adrenoreceptor is a regulator of the alpha-synuclein gene driving risk of Parkinson's disease. *Science* 357, 891-898 (2017).
7. H. Javed et al., Development of Nonviral Vectors Targeting the Brain as a Therapeutic Approach For Parkinson's Disease and Other Brain Disorders. *Molecular therapy: the journal of the American Society of Gene Therapy* 24, 746-758 (2016).
8. K. Ubhi et al., Alpha-synuclein deficient mice are resistant to toxin-induced multiple system atrophy. *Neuroreport* 21, 457-462 (2010).
9. Y. Lim et al., alpha-Syn suppression reverses synaptic and memory defects in a mouse model of dementia with Lewy bodies. *The Journal of neuroscience: the official journal of the Society for Neuroscience* 31, 10076-10087 (2011).
10. S. Schildknecht et al., Generation of genetically-modified human differentiated cells for toxicological tests and the study of neurodegenerative diseases. *Altex* 30, 427-444 (2013).
11. X. Xiao, J. Li, R. J. Samulski, Production of high-titer recombinant adeno-associated virus vectors in the absence of helper adenovirus. *Journal of virology* 72, 2224-2232 (1998).

Sequences

All polypeptide sequences are presented as N-terminal to C-terminal unless indicated otherwise. All nucleic acid sequences are presented as 5' to 3' unless indicated otherwise.

D1-loop-passenger -RNA (SEQ ID NO: 61)

UGCUCUUUGGUCUUCUCAGCCGUUUUGGCCACUGACUGACGGCUGAGAACCAAAGAGUA

D1-loop-passenger -DNA (SEQ ID NO: 62)

TGCTCTTTGGTCTTCTCAGCCGTTTTGGCCACTGACTGACGGCTGAGAACCAAAGAGTA

E1-loop-passenger -RNA (SEQ ID NO: 63)

UGGGCACAUUGGAACUGAGCAGUUUUGGCCACUGACUGACUGCUCAGUCAAUGUGCCUA

E1-loop-passenger -DNA (SEQ ID NO: 64)

TGGGCACATTGGAACTGAGCAGTTTTGGCCACTGACTGACTGCTCAGTCAATGTGCCTA

D1 Vector Genome Sequence (SEQ ID NO: 65)

TTGGCCACTCCCTCTCTGCGCGCTCGCTCGCTCACTGAGGCCGCCCGGGCAAAGCCCGGGCGTCGGGCGACCTTTGGTCGCCCGGCCTCAGTGAGCGAGCGAGCGCGCAGAGAGGGAGTGGCCAACTCCATCACTAGGGGTTCCTTACGTACAATTGGGATCCCGGACCGTCGACATTGATTATTGACTAGTTATTAATAGTAATCAATTACGGGGTCATTAGTTCATAGCCCATATATGGAGTTCCGCGTTACATAACTTACGGTAAATGGCCCGCCTGGCTGACCGCCCAACGACCCCCGCCCATTGACGTCAATAATGACGTATGTTCCCATAGTAACGCCAATAGGGACTTTCCATTGACGTCAATGGGTGGAGTATTTACGGTAAATGCCCACTTGGCAGTACATCAAGTGTATCATATGCCAAGTACGCCCCCTATTGACGTCAATGACGGTAAATGGCCCGCCTGGCATTATGCCCAGTACATGACCTTATGGGACTTTCCTACTTGGCAGTACATCTACGTATTAGTCATCGCTATTACCATGGTCGAGGTGAGCCCCACGTTCTGCTTCACTCTCCCCATCTCCCCCCCCTCCCACCCCCAATTTTGTATTTATTTATTTTTTAATTATTTTGTGCAGCGATGGGGGCGGGGGGGGGGGGGGCGCGCGCCAGGCGGGGCGGGCGGGGCGAGGGGCGGGCGGGCGAGGCGGAGAGGTGCGGCGGCAGCCAATCAGAGCGGCGCGCTCCGAAAGTTTCCTTTTATGGCGAGGCGGCGGCGGCGGCGGCCCTATAAAAAGCGAAGCGCGCGGCGGGGGGAGTCGCTGCGACGCTGCCTTCGCCCCGTGCCCCGCTCCGCCGCCGCCTCGCGCCGCCCGCCCCGGCTCTGACTGACCGCGTTACTCCCACAGGTGAGCGGGCGGGACGGCCCTTCTCCTCCGGGCTGTAATTAGCGCTTGGTTTAATGACGGCTTGTTTCTTTTCTGTGGCTGCGTGAAAGCCTTGAGGGGCTCCGGGAGGGCCCTTTGTGCGGGGGGAGCGGCTCGGGGGGTGCGTGCGTGTGTGTGTGCGTGGGGAGCGCCGCGTGCGGCTCCGCGCTGCCCGGCGGCTGTGAGCGCTGCGGGCGCGGCGGGCTTTGTGCGCTCCGCAGTGTGCGCGAGGGGAGCGCGGCCGGGGGCGGTGCCCCGCGGTGCGGGGGGGGCTGCGAGGGGAACAAAGGCTGCGTGCGGGGTGTGTGCGTGGGGGGGTGAGCAGGGGGTGTGGGCGCGTCGGTCGGGCTGCAACCCCCCTGCACCCCCCTCCCCGAGTTGCTGAGCACGGCCCGGCTTCGGGTGCGGGGCTCCGTACGGGGCGTGGCGCGGGGCTCGCCGTGCCGGGCGGGGGGTGGCGGCAGGTGGGGGTGCCGGGCGGGGGGGGGCGCCTCGGGCCGGGACGGCCTCGGGGAGGGGCGCGGCGGCCCCGGAGCGCCGGCGGCTGTCGAGGCGCGGCGAGCCGCAGCCATTGCCTTTTATGGTAATCGTGCGAGAGGGCGCAGGGACTTCCTTTGTCCCAAATCTGTGCGGAGCCGAAATCTGGGAGGCGCCGCCGCACCCCCTCTAGCGGGCGCGGGGCGAAGCGGTGCGGCGCCGGCAGGAAGGAAATGGGCGGGGAGGGCCTTCGTGCGTCGCCGCGCCGCCGTCCCCTTCTCCCTCTCCAGCCTCGGGGCTGTCCGCGGGGGGACGGCTGCCTTCGGGGGGACGGGGCAGGGCGGGGTTCGGCTTCTGGCGTGTGACCGGCGGCTCTAGAGCCTCTGCTAACCATGTTCATGCCTTCTTCTTTTTCCTACAGCTCCTGGGCAACGTGCTGGTTATTGTGCTGTCTCATCTTTTGGCAAAGAATTCTTCGAAAGATCTGCTAGCCTAGACTGGAGGCTTGCTGAAGGCTGTATGCTGTGCTCTTTGGTCTTCTCAGCCGTTTTGGCCACTGACTGACGGCTGAGAACCAAAGAGTACAGGACACAAGGCCTGTTACTAGCACTCACATGGAACAAATGGCCCAGATCTGGCCGCACTCGAGATCTCGCTGATCAGCCTCGACTGTGCCTTCTAGTTGCCAGCCATCTGTTGTTTGCCCCTCCCCCGTGCCTTCCTTGACCCTGGAAGGTGCCACTCCCACTGTCCTTTCCTAATAAAATGAGGAAATTGCATCGCATTGTCTGAGTAGGTGTCATTCTATTCTGGGGGGTGGGGTGGGGCAGGACAGCAAGGGGGAGGATTGGGAAGACAATAGCAGGCATGCTGGGGAGCCTAGAGTCGACCGGACCGGTGGAAGTCCTCTTCCTCGGTGTCCTTGACTTCAAAGGGTCTCTCCCATTTGCCTGGAGAGAGGGGAAGGTGGGCATCACCAGGGGTGAGTGAAGGTTTGGAAGAGTGTAGCAGAATAAGAAACCATGAGTCCCCTCCCTGAGAAGCCCTGAGCCCCCTTGACGACACACATCCCTCGAGGCTCAGCTTCATCATCTGTAAAAGGTGCTGAAACTGACCATCCAAGCTGCCGAAAAAGATTGTGTGGGGATAATTCAAAACTAGAGGAAGATGCAGAATTTCTACATCGTGGCGATGTCAGGCTAAGAGATGCCATCGTGGCTGTGCATTTTTATTGGAATCATATGTTTATTTGAGGGTGTCTTGGATATTACAAATAAAATGTTGGAGCATCAGGCATATTTGGTACCTTCTGTCTAAGGCTCCCTGCCCCTTGTTAATTGGCAGCTCAGTTATTCATCCAGGGCAAACATTCTGCTTACTATTCCTGAGAGCTTTCCTCATCCTCTAGATTGGCAGGGGAAATGCAGATGCCTGAGCAGCCTCCCCTCTGCCTACCAACAGAGCTTCACCATCGAGGCATGCAGAGTGGACAGGGGCCTCAGGACCCCTGATCCCAGCTTTCTCATTGGACAGAAGGAGGAGACTGGGGCTGGAGAGGGACCTGGGCCCCCACTAAGGCCACAGCAGAGCCAGGACTTTAGCTGTGCTGACTGCAGCCTGGCTTGCCTCCACTGCCCTCCTTTGCCTCAAGAGCAAGGGAGCCTCAGAGTGGAGGAAGCAGCCCCTGGCCTTGCCTCCCACCTCCCCTCCCCTATGCTGTTTTCCTGGGACAGTGGGAGCTGGCTTAGAATGCCCTGGGGCCCCAGGACCCTGGCATTTTAACCCCTCAGGGGCAGGAAGGCAGCCTGAGATACAGAAGAGTCCATCACCTGCTGTATGCCACACACCATCCCCACAGTCGACATTTAAATTGGCCACTCCCTCTCTGCGCGCTCGCTCGCTCACTGAGGCCGCCCGGGCAAGCCCGGGCGTCGGGCGACCTTTGGTCGCCCGGCCTCAGTGAGCGAGCGCGCAGAGAGGGAGTGGCCAA.

A1AT stuffer nucleic acid (SEQ ID NO: 66)

ATTGTCTGAGTAGGTGTCATTCTATTCTGGGGGGTGGGGTGGGGCAGGACAGCAAGGGGGAGGATTGGGAAGACAATAGCAGGCATGCTGGGGAGCTAGAGTCGACCGGACCGGTGGAAGTCCTCTTCCTCGGTGTCCTTGACTTCAAAGGGTCTCTCCCATTTGCCTGGAGAGAGGGGAAGGTGGGCATCACCAGGGGTGAGTGAAGGTTTGGAAGAGTGTAGCAGAATAAGAAACCATGAGTCCCCTCCCTGAGAAGCCCTGAGCCCCCTTGACGACACACATCCCTCGAGGCTCAGCTTCATCATCTGTAAAAGGTGCTGAAACTGACCATCCAAGCTGCCGAAAAAGATTGTGTGGGGATAATTCAAAACTAGAGGAAGATGCAGAATTTCTACATCGTGGCGATGTCAGGCTAAGAGATGCCATCGTGGCTGTGCATTTTTATTGGAATCATATGTTTATTTGAGGGTGTCTTGGATATTACAAATAAAATGTTGGAGCATCAGGCATATTTGGTACCTTCTGTCTAAGGCTCCCTGCCCCTTGTTAATTGGCAGCTCAGTTATTCATCCAGGGCAAACATTCTGCTTACTATTCCTGAGAGCTTTCCTCATCCTCTAGATTGGCAGGGGAAATGCAGATGCCTGAGCAGCCTCCCCTCTGCCTACCAACAGAGCTTCACCATCGAGGCATGCAGAGTGGACAGGGGCCTCAGGACCCCTGATCCCAGCTTTCTCATTGGACAGAAGGAGGAGACTGGGGCTGGAGAGGGACCTGGGCCCCCACTAAGGCCACAGCAGAGCCAGGACTTTAGCTGTGCTGACTGCAGCCTGGCTTGCCTCCACTGCCCTCCTTTGCCTCAAGAGCAAGGGAGCCTCAGAGTGGAGGAAGCAGCCCCTGGCCTTGCCTCCCACCTCCCCTCCCCTATGCTGTTTTCCTGGGACAGTGGGAGCTGGCTTAGAATGCCCTGGGGCCCCAGGACCCTGGCATTTTAACCCCTCAGGGGCAGGAAGGCAGCCTGAGATACAGAAGAGTCCATCACCTGCTGTATGCCACACACCATCCCCACAGTCGACATTTAAATT

---

What is claimed is:

1. An RNAi comprising a first strand and a second strand, wherein:
   a) the first strand and the second strand form a duplex;
   b) the first strand comprises a guide region, wherein the guide region comprises a nucleic acid having the sequence 5'-ACUGCGCACAUUGGAACUGAG-3' (SEQ ID NO: 29); and
   c) the second strand comprises a non-guide region.

2. The RNAi of claim 1, wherein the first strand and the second strand are linked by means of a RNA linker; wherein the RNA linker is capable of forming a loop structure.

3. The RNAi of claim 2, wherein the RNA linker comprises from 4 to 50 nucleotides or 4 to 20 nucleotides.

4. The RNAi of claim 1, wherein the RNAi is a small inhibitory RNA (siRNA), a microRNA (miRNA), or a small hairpin RNA (shRNA).

5. The RNAi of claim 1, wherein the RNAi targets RNA encoding a polypeptide associated with a neurodegenerative synucleinopathy wherein the neurodegenerative synucleinopathy is Parkinson's disease (PD), multiple system atropy (MSA), or dementia with Lewy bodies (DLB).

6. An expression construct comprising nucleic acid encoding the RNAi of claim 1.

7. A vector comprising the expression construct of claim 6.

8. The vector of claim 7, wherein the vector is a recombinant adeno-associated virus (rAAV) vector.

9. A cell comprising the rAAV vector of claim 8.

10. A recombinant AAV particle comprising the rAAV vector of claim 7.

11. The RNAi of claim 1, wherein the second strand comprises a nucleic acid having at least 90% identity to the sequence 5'-CUCAGUUCAUGUGCGCAGU-3' (SEQ ID NO 58).

12. The RNAi of claim 1, wherein the second strand comprises a nucleic acid sequence 5'-CUCAGUUCAUGUGCGCAGU-3' (SEQ ID NO: 58).

* * * * *

SEQUENCE LISTING

<160> NUMBER OF SEQ ID NOS: 70

<210> SEQ ID NO 1
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1
caucggaacu gagcacuugu a            21

```
<210> SEQ ID NO 2
<211> LENGTH: 22
<212> TYPE: RNA
<213> ORGANISM: Artificial Sequence
<220> FEATURE:
<223> OTHER INFORMATION: Synthetic Construct

<400> SEQUENCE: 2
agguucguag ucuugauacc cu                                                  22

<210> SEQ ID NO 3
<211> LENGTH: 22
<212> TYPE: RNA
<213> ORGANISM: Artificial Sequence
<220> FEATURE:
<223> OTHER INFORMATION: Synthetic Construct

<400> SEQUENCE: 3
uuaaccgcca cuucuaacc uu                                                   22

<210> SEQ ID NO 4
<211> LENGTH: 21
<212> TYPE: RNA
<213> ORGANISM: Artificial Sequence
<220> FEATURE:
<223> OTHER INFORMATION: Synthetic Construct

<400> SEQUENCE: 4
acguuggaac ugagcacuug u                                                   21

<210> SEQ ID NO 5
<211> LENGTH: 21
<212> TYPE: RNA
<213> ORGANISM: Artificial Sequence
<220> FEATURE:
<223> OTHER INFORMATION: Synthetic Construct

<400> SEQUENCE: 5
uuccaacauu ugucacuugc u                                                   21

<210> SEQ ID NO 6
<211> LENGTH: 21
<212> TYPE: RNA
<213> ORGANISM: Artificial Sequence
<220> FEATURE:
<223> OTHER INFORMATION: Synthetic Construct

<400> SEQUENCE: 6
ucguccaaca uuugucacuu g                                                   21

<210> SEQ ID NO 7
<211> LENGTH: 21
<212> TYPE: RNA
<213> ORGANISM: Artificial Sequence
<220> FEATURE:
<223> OTHER INFORMATION: Synthetic Construct

<400> SEQUENCE: 7
ugggcgcauu ggaacugagc a                                                   21

<210> SEQ ID NO 8
<211> LENGTH: 21
<212> TYPE: RNA
<213> ORGANISM: Artificial Sequence
<220> FEATURE:
<223> OTHER INFORMATION: Synthetic Construct
```

```
<400> SEQUENCE: 8
ugggcacauu ggaacugagc a                                              21

<210> SEQ ID NO 9
<211> LENGTH: 21
<212> TYPE: RNA
<213> ORGANISM: Artificial Sequence
<220> FEATURE:
<223> OTHER INFORMATION: Synthetic Construct

<400> SEQUENCE: 9
gucgucgaau ggccacuccc a                                              21

<210> SEQ ID NO 10
<211> LENGTH: 22
<212> TYPE: RNA
<213> ORGANISM: Artificial Sequence
<220> FEATURE:
<223> OTHER INFORMATION: Synthetic Construct

<400> SEQUENCE: 10
gguucguagu cuugauaccc uu                                             22

<210> SEQ ID NO 11
<211> LENGTH: 21
<212> TYPE: RNA
<213> ORGANISM: Artificial Sequence
<220> FEATURE:
<223> OTHER INFORMATION: Synthetic Construct

<400> SEQUENCE: 11
uagcagcagc cacaacuccc u                                              21

<210> SEQ ID NO 12
<211> LENGTH: 21
<212> TYPE: RNA
<213> ORGANISM: Artificial Sequence
<220> FEATURE:
<223> OTHER INFORMATION: Synthetic Construct

<400> SEQUENCE: 12
uucgaacauu ugucacuugc u                                              21

<210> SEQ ID NO 13
<211> LENGTH: 21
<212> TYPE: RNA
<213> ORGANISM: Artificial Sequence
<220> FEATURE:
<223> OTHER INFORMATION: Synthetic Construct

<400> SEQUENCE: 13
uagccgccac aacucccucc u                                              21

<210> SEQ ID NO 14
<211> LENGTH: 21
<212> TYPE: RNA
<213> ORGANISM: Artificial Sequence
<220> FEATURE:
<223> OTHER INFORMATION: Synthetic Construct

<400> SEQUENCE: 14
ugcgcuuugg ucuucucagc c                                              21

<210> SEQ ID NO 15
<211> LENGTH: 21
```

```
<212> TYPE: RNA
<213> ORGANISM: Artificial Sequence
<220> FEATURE:
<223> OTHER INFORMATION: Synthetic Construct

<400> SEQUENCE: 15
uagccgcagc cacaacuccc u                                              21

<210> SEQ ID NO 16
<211> LENGTH: 21
<212> TYPE: RNA
<213> ORGANISM: Artificial Sequence
<220> FEATURE:
<223> OTHER INFORMATION: Synthetic Construct

<400> SEQUENCE: 16
uagcagccac aacucccucc u                                              21

<210> SEQ ID NO 17
<211> LENGTH: 21
<212> TYPE: RNA
<213> ORGANISM: Artificial Sequence
<220> FEATURE:
<223> OTHER INFORMATION: Synthetic Construct

<400> SEQUENCE: 17
ucggcacauu ggaacugagc a                                              21

<210> SEQ ID NO 18
<211> LENGTH: 21
<212> TYPE: RNA
<213> ORGANISM: Artificial Sequence
<220> FEATURE:
<223> OTHER INFORMATION: Synthetic Construct

<400> SEQUENCE: 18
augacggggc acauuggaac u                                              21

<210> SEQ ID NO 19
<211> LENGTH: 21
<212> TYPE: RNA
<213> ORGANISM: Artificial Sequence
<220> FEATURE:
<223> OTHER INFORMATION: Synthetic Construct

<400> SEQUENCE: 19
augacugggc acauuggaac u                                              21

<210> SEQ ID NO 20
<211> LENGTH: 21
<212> TYPE: RNA
<213> ORGANISM: Artificial Sequence
<220> FEATURE:
<223> OTHER INFORMATION: Synthetic Construct

<400> SEQUENCE: 20
uaagucguag ucacuuaggu g                                              21

<210> SEQ ID NO 21
<211> LENGTH: 21
<212> TYPE: RNA
<213> ORGANISM: Artificial Sequence
<220> FEATURE:
<223> OTHER INFORMATION: Synthetic Construct

<400> SEQUENCE: 21
```
cuccgcagca gccacaacuc c                                              21

<210> SEQ ID NO 22
<211> LENGTH: 21
<212> TYPE: RNA
<213> ORGANISM: Artificial Sequence
<220> FEATURE:
<223> OTHER INFORMATION: Synthetic Construct

<400> SEQUENCE: 22
ucaugacugg gcacauugga a                                              21

<210> SEQ ID NO 23
<211> LENGTH: 21
<212> TYPE: RNA
<213> ORGANISM: Artificial Sequence
<220> FEATURE:
<223> OTHER INFORMATION: Synthetic Construct

<400> SEQUENCE: 23
aaauacgugg uagucacuua g                                              21

<210> SEQ ID NO 24
<211> LENGTH: 21
<212> TYPE: RNA
<213> ORGANISM: Artificial Sequence
<220> FEATURE:
<223> OTHER INFORMATION: Synthetic Construct

<400> SEQUENCE: 24
ugcucuuugg ucuucucagc c                                              21

<210> SEQ ID NO 25
<211> LENGTH: 21
<212> TYPE: RNA
<213> ORGANISM: Artificial Sequence
<220> FEATURE:
<223> OTHER INFORMATION: Synthetic Construct

<400> SEQUENCE: 25
aacguuuguc acuugcucuu u                                              21

<210> SEQ ID NO 26
<211> LENGTH: 21
<212> TYPE: RNA
<213> ORGANISM: Artificial Sequence
<220> FEATURE:
<223> OTHER INFORMATION: Synthetic Construct

<400> SEQUENCE: 26
aaauaagugg uagucacuua g                                              21

<210> SEQ ID NO 27
<211> LENGTH: 21
<212> TYPE: RNA
<213> ORGANISM: Artificial Sequence
<220> FEATURE:
<223> OTHER INFORMATION: Synthetic Construct

<400> SEQUENCE: 27
uuagaaauaa gugguaguca c                                              21

<210> SEQ ID NO 28
<211> LENGTH: 21
<212> TYPE: RNA
<213> ORGANISM: Artificial Sequence

```
<220> FEATURE:
<223> OTHER INFORMATION: Synthetic Construct

<400> SEQUENCE: 28 aauacgguggu agucacuuag g                                             21

<210> SEQ ID NO 29
<211> LENGTH: 21
<212> TYPE: RNA
<213> ORGANISM: Artificial Sequence
<220> FEATURE:
<223> OTHER INFORMATION: Synthetic Construct

<400> SEQUENCE: 29
acugcgcaca uuggaacuga g                                              21

<210> SEQ ID NO 30
<211> LENGTH: 19
<212> TYPE: RNA
<213> ORGANISM: Artificial Sequence
<220> FEATURE:
<223> OTHER INFORMATION: Synthetic Construct

<400> SEQUENCE: 30
uacaagugca guuccgaug                                                 19

<210> SEQ ID NO 31
<211> LENGTH: 20
<212> TYPE: RNA
<213> ORGANISM: Artificial Sequence
<220> FEATURE:
<223> OTHER INFORMATION: Synthetic Construct

<400> SEQUENCE: 31
aagguuagaa uggcgguuaa                                                20

<210> SEQ ID NO 32
<211> LENGTH: 20
<212> TYPE: RNA
<213> ORGANISM: Artificial Sequence
<220> FEATURE:
<223> OTHER INFORMATION: Synthetic Construct

<400> SEQUENCE: 32
aagguuagaa uggcgguuaa                                                20

<210> SEQ ID NO 33
<211> LENGTH: 19
<212> TYPE: RNA
<213> ORGANISM: Artificial Sequence
<220> FEATURE:
<223> OTHER INFORMATION: Synthetic Construct

<400> SEQUENCE: 33
acaagugcag uuccaacgu                                                 19

<210> SEQ ID NO 34
<211> LENGTH: 19
<212> TYPE: RNA
<213> ORGANISM: Artificial Sequence
<220> FEATURE:
<223> OTHER INFORMATION: Synthetic Construct

<400> SEQUENCE: 34
agcaagugaa auguuggaa                                                 19
```

```
<210> SEQ ID NO 35
<211> LENGTH: 19
<212> TYPE: RNA
<213> ORGANISM: Artificial Sequence
<220> FEATURE:
<223> OTHER INFORMATION: Synthetic Construct

<400> SEQUENCE: 35
caagugacau guuggacga                                                      19

<210> SEQ ID NO 36
<211> LENGTH: 19
<212> TYPE: RNA
<213> ORGANISM: Artificial Sequence
<220> FEATURE:
<223> OTHER INFORMATION: Synthetic Construct

<400> SEQUENCE: 36
ugcucaguca augcgccua                                                      19

<210> SEQ ID NO 37
<211> LENGTH: 19
<212> TYPE: RNA
<213> ORGANISM: Artificial Sequence
<220> FEATURE:
<223> OTHER INFORMATION: Synthetic Construct

<400> SEQUENCE: 37
ugcucaguca augugccua                                                      19

<210> SEQ ID NO 38
<211> LENGTH: 19
<212> TYPE: RNA
<213> ORGANISM: Artificial Sequence
<220> FEATURE:
<223> OTHER INFORMATION: Synthetic Construct

<400> SEQUENCE: 38
ugggagugca uucgacgau                                                      19

<210> SEQ ID NO 39
<211> LENGTH: 20
<212> TYPE: RNA
<213> ORGANISM: Artificial Sequence
<220> FEATURE:
<223> OTHER INFORMATION: Synthetic Construct

<400> SEQUENCE: 39
aaggguauca acuacgaacc                                                     20

<210> SEQ ID NO 40
<211> LENGTH: 19
<212> TYPE: RNA
<213> ORGANISM: Artificial Sequence
<220> FEATURE:
<223> OTHER INFORMATION: Synthetic Construct

<400> SEQUENCE: 40
agggaguugg cugcugcua                                                      19

<210> SEQ ID NO 41
<211> LENGTH: 19
<212> TYPE: RNA
<213> ORGANISM: Artificial Sequence
<220> FEATURE:
<223> OTHER INFORMATION: Synthetic Construct
```

<400> SEQUENCE: 41
agcaagugaa auguucgaa                                                19

<210> SEQ ID NO 42
<211> LENGTH: 19
<212> TYPE: RNA
<213> ORGANISM: Artificial Sequence
<220> FEATURE:
<223> OTHER INFORMATION: Synthetic Construct

<400> SEQUENCE: 42
aggagggaug uggcggcua                                                19

<210> SEQ ID NO 43
<211> LENGTH: 19
<212> TYPE: RNA
<213> ORGANISM: Artificial Sequence
<220> FEATURE:
<223> OTHER INFORMATION: Synthetic Construct

<400> SEQUENCE: 43
ggcugagaac caaagcgua                                                19

<210> SEQ ID NO 44
<211> LENGTH: 19
<212> TYPE: RNA
<213> ORGANISM: Artificial Sequence
<220> FEATURE:
<223> OTHER INFORMATION: Synthetic Construct

<400> SEQUENCE: 44
agggaguugg cugcggcua                                                19

<210> SEQ ID NO 45
<211> LENGTH: 19
<212> TYPE: RNA
<213> ORGANISM: Artificial Sequence
<220> FEATURE:
<223> OTHER INFORMATION: Synthetic Construct

<400> SEQUENCE: 45
aggagggaug uggcugcua                                                19

<210> SEQ ID NO 46
<211> LENGTH: 19
<212> TYPE: RNA
<213> ORGANISM: Artificial Sequence
<220> FEATURE:
<223> OTHER INFORMATION: Synthetic Construct

<400> SEQUENCE: 46
ugcucaguca augugccga                                                19

<210> SEQ ID NO 47
<211> LENGTH: 19
<212> TYPE: RNA
<213> ORGANISM: Artificial Sequence
<220> FEATURE:
<223> OTHER INFORMATION: Synthetic Construct

<400> SEQUENCE: 47
aguuccaaug ccccgucau                                                19

<210> SEQ ID NO 48

```
<211> LENGTH: 19
<212> TYPE: RNA
<213> ORGANISM: Artificial Sequence
<220> FEATURE:
<223> OTHER INFORMATION: Synthetic Construct

<400> SEQUENCE: 48
aguuccaaug cccagucau                                                         19

<210> SEQ ID NO 49
<211> LENGTH: 19
<212> TYPE: RNA
<213> ORGANISM: Artificial Sequence
<220> FEATURE:
<223> OTHER INFORMATION: Synthetic Construct

<400> SEQUENCE: 49
caccuaagac uacgacuua                                                         19

<210> SEQ ID NO 50
<211> LENGTH: 19
<212> TYPE: RNA
<213> ORGANISM: Artificial Sequence
<220> FEATURE:
<223> OTHER INFORMATION: Synthetic Construct

<400> SEQUENCE: 50
ggaguugucu gcugcggag                                                         19

<210> SEQ ID NO 51
<211> LENGTH: 19
<212> TYPE: RNA
<213> ORGANISM: Artificial Sequence
<220> FEATURE:
<223> OTHER INFORMATION: Synthetic Construct

<400> SEQUENCE: 51
uuccaaugcc cagucauga                                                         19

<210> SEQ ID NO 52
<211> LENGTH: 19
<212> TYPE: RNA
<213> ORGANISM: Artificial Sequence
<220> FEATURE:
<223> OTHER INFORMATION: Synthetic Construct

<400> SEQUENCE: 52
cuaagugaac cacguauuu                                                         19

<210> SEQ ID NO 53
<211> LENGTH: 19
<212> TYPE: RNA
<213> ORGANISM: Artificial Sequence
<220> FEATURE:
<223> OTHER INFORMATION: Synthetic Construct

<400> SEQUENCE: 53
ggcugagaac caaagagua                                                         19

<210> SEQ ID NO 54
<211> LENGTH: 19
<212> TYPE: RNA
<213> ORGANISM: Artificial Sequence
<220> FEATURE:
<223> OTHER INFORMATION: Synthetic Construct

<400> SEQUENCE: 54
```
aaagagcaug acaaacguu                                              19

<210> SEQ ID NO 55
<211> LENGTH: 19
<212> TYPE: RNA
<213> ORGANISM: Artificial Sequence
<220> FEATURE:
<223> OTHER INFORMATION: Synthetic Construct

<400> SEQUENCE: 55
cuaagugaac cacuuauuu                                              19

<210> SEQ ID NO 56
<211> LENGTH: 19
<212> TYPE: RNA
<213> ORGANISM: Artificial Sequence
<220> FEATURE:
<223> OTHER INFORMATION: Synthetic Construct

<400> SEQUENCE: 56
gugacuaccu uauuucuaa                                              19

<210> SEQ ID NO 57
<211> LENGTH: 19
<212> TYPE: RNA
<213> ORGANISM: Artificial Sequence
<220> FEATURE:
<223> OTHER INFORMATION: Synthetic Construct

<400> SEQUENCE: 57
ccuaagugua ccacguauu                                              19

<210> SEQ ID NO 58
<211> LENGTH: 19
<212> TYPE: RNA
<213> ORGANISM: Artificial Sequence
<220> FEATURE:
<223> OTHER INFORMATION: Synthetic Construct

<400> SEQUENCE: 58
cucaguucau gugcgcagu                                              19

<210> SEQ ID NO 59
<211> LENGTH: 19
<212> TYPE: DNA
<213> ORGANISM: Artificial Sequence
<220> FEATURE:
<223> OTHER INFORMATION: Synthetic Construct

<400> SEQUENCE: 59
gttttggcca ctgactgac                                              19

<210> SEQ ID NO 60
<211> LENGTH: 19
<212> TYPE: RNA
<213> ORGANISM: Artificial Sequence
<220> FEATURE:
<223> OTHER INFORMATION: Synthetic Construct

<400> SEQUENCE: 60
guuuuggcca cugacugac                                              19

<210> SEQ ID NO 61
<211> LENGTH: 59
<212> TYPE: RNA

<213> ORGANISM: Artificial Sequence
<220> FEATURE:
<223> OTHER INFORMATION: Synthetic Construct

<400> SEQUENCE: 61
ugcucuuugg ucuucucagc cguuuuggcc acugacugac ggcugagaac caaagagua         59

<210> SEQ ID NO 62
<211> LENGTH: 59
<212> TYPE: DNA
<213> ORGANISM: Artificial Sequence
<220> FEATURE:
<223> OTHER INFORMATION: Synthetic Construct

<400> SEQUENCE: 62
tgctctttgg tcttctcagc cgttttggcc actgactgac ggctgagaac caaagagta         59

<210> SEQ ID NO 63
<211> LENGTH: 59
<212> TYPE: RNA
<213> ORGANISM: Artificial Sequence
<220> FEATURE:
<223> OTHER INFORMATION: Synthetic Construct

<400> SEQUENCE: 63
ugggcacauu ggaacugagc aguuuuggcc acugacugac ugcucaguca augugccua         59

<210> SEQ ID NO 64
<211> LENGTH: 59
<212> TYPE: DNA
<213> ORGANISM: Artificial Sequence
<220> FEATURE:
<223> OTHER INFORMATION: Synthetic Construct

<400> SEQUENCE: 64
tgggcacatt ggaactgagc agttttggcc actgactgac tgctcagtca atgtgccta         59

<210> SEQ ID NO 65
<211> LENGTH: 3455
<212> TYPE: DNA
<213> ORGANISM: Artificial Sequence
<220> FEATURE:
<223> OTHER INFORMATION: Synthetic Construct

<400> SEQUENCE: 65

| | | |
|---|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttccttacgt acaattggga tcccggaccg tcgacattga | 180 |
| ttattgacta gttattaata gtaatcaatt acggggtcat tagttcatag cccatatatg | 240 |
| gagttccgcg ttacataact tacggtaaat ggcccgcctg gctgaccgcc caacgacccc | 300 |
| cgcccattga cgtcaataat gacgtatgtt cccatagtaa cgccaatagg gactttccat | 360 |
| tgacgtcaat gggtggagta tttacggtaa actgcccact tggcagtaca tcaagtgtat | 420 |
| catatgccaa gtacgccccc tattgacgtc aatgacggta atggcccgc ctggcattat | 480 |
| gcccagtaca tgaccttatg gactttcct acttggcagt acatctacgt attagtcatc | 540 |
| gctattacca tggtcgaggt gagccccacg ttctgcttca ctctccccat ctccccccc | 600 |
| tccccacccc caattttgta tttatttatt ttttaattat tttgtgcagc gatggggcg | 660 |
| ggggggggg ggggcgcgc gccaggcggg gcggggcggg gcgaggggcg ggcggggcg | 720 |
| aggcggagag gtgcggcggc agccaatcag agcggcgcgc tccgaaagtt tccttttatg | 780 |

```
gcgaggcggc ggcggcggcg gccctataaa aagcgaagcg cgcggcgggc ggggagtcgc    840
tgcgacgctg ccttcgcccc gtgccccgct ccgccgccgc ctcgcgccgc ccgccccggc    900
tctgactgac cgcgttactc ccacaggtga gcgggcggga cggccttct cctccgggct     960 gtaattagcg cttggtttaa tgacggcttg tttcttttct gtggctgcgt gaaagcttg    1020 aggggctccg ggagggccct tgtgcgggg ggagcggctc gggggtgcg tgcgtgtgtg    1080 tgtgcgtggg gagcgccgcg tgcggctccg cgctgcccgg cggctgtgag cgctgcgggc    1140
gcggcgcggg gctttgtgcg ctccgcagtg tgcgcgaggg gagcgcggcc ggggcggtg    1200 ccccgcggtg cgggggggc tgcgagggga acaaaggctg cgtgcggggt gtgtgcgtgg    1260
gggggtgagc aggggggtgtg ggcgcgtcgg tcggctgca accccccctg cacccccctc    1320
cccgagttgc tgagcacggc ccggcttcgg gtgcggggct ccgtacgggg cgtgcgcgg    1380 ggctcgccgt gccgggcggg gggtggcggc aggtggggt gccgggcggg gcggggccgc    1440
ctcgggccgg ggagggctcg ggggagggc gcggcggccc ccggagcgcc ggcggctgtc    1500
gaggcgcggc gagccgcagc cattgccttt tatggtaatc gtgcgagagg gcgcagggac    1560
ttcctttgtc ccaaatctgt gcggagccga atctgggag gcgccgccgc accccctcta    1620
gcgggcgcgg ggcgaagcgg tgcggcgccg gcaggaagga aatgggcggg gagggccttc    1680
gtgcgtcgcc gcgccgccgt ccccttctcc ctctccagcc tcggggctgt ccgcgggggg    1740
acggctgcct tcggggggga cggggcaggg cggggttcgg cttctggcgt gtgaccggcg    1800
gctctagagc ctctgctaac catgttcatg ccttcttctt tttcctacag ctcctgggca    1860
acgtgctggt tattgtgctg tctcatcatt ttggcaaaga attcttcgaa agatctgcta    1920
gcctagactg gaggcttgct gaaggctgta tgctgtgctc tttggtcttc tcagccgttt    1980
tggccactga ctgacggctg agaaccaaag agtacaggac acaaggcctg ttactagcac    2040
tcacatggaa caaatggccc agatctggcc gcactcgaga tatcgagctc gctgatcagc    2100
ctcgactgtg ccttctagtt gccagccatc tgttgtttgc ccctcccccg tgccttcctt    2160
gaccctggaa ggtgccactc ccactgtcct ttcctaataa aatgaggaaa ttgcatcgca    2220
ttgtctgagt aggtgtcatt ctattctggg ggtgggtg gggcaggaca gcaagggga    2280 ggattgggaa gacaatagca ggcatgctgg ggagctagag tcgaccggac cggtggaagt    2340
cctcttcctc ggtgtccttg acttcaaagg gtctctccca tttgcctgga gagagggaa    2400 ggtgggcatc accaggggtg agtgaaggtt tggaagagtg tagcagaata agaaaccatg    2460
agtcccctcc ctgagaagcc ctgagccccc ttgacgacac acatccctcg aggctcagct    2520
tcatcatctg taaaaggtgc tgaaactgac catccaagct gccgaaaaag attgtgtggg    2580
gataattcaa aactagagga agatgcagaa tttctacatc gtggcgatgt caggctaaga    2640
gatgccatcg tggctgtgca ttttattgg aatcatatgt ttatttgagg gtgtcttgga    2700
tattacaaat aaaatgttgg agcatcaggc atatttggta ccttctgtct aaggctccct    2760
gccccttgtt aattggcagc tcagttattc atccagggca acattctgc ttactattcc    2820 tgagagcttt cctcatcctc tagattggca ggggaaatgc agatgcctga gcagcctccc    2880
ctctgccata ccaacagagc ttcaccatcg aggcatgcag agtggacagg ggcctcaggg    2940
acccctgatc ccagctttct cattggacag aaggaggaga ctgggctgg agaggaccct    3000 gggcccccac taaggccaca gcagagccag gactttagct gtgctgactg cagcctggct    3060
tgcctccact gccctccttt gcctcaagag caagggagcc tcagagtgga ggaagcagcc    3120
```

```
cctggccttg cctcccacct cccctcccct atgctgtttt cctgggacag tgggagctgg    3180
cttagaatgc cctggggccc ccaggaccct ggcattttaa cccctcaggg gcaggaaggc    3240
agcctgagat acagaagagt ccatcacctg ctgtatgcca cacaccatcc ccacagtcga    3300
catttaaatt aggaacccct agtgatggag ttggccactc cctctctgcg cgctcgctcg    3360
ctcactgagg ccgcccgggc aaagcccggg cgtcgggcga cctttggtcg cccggcctca    3420
gtgagcgagc gagcgcgcag agagggagtg gccaa                              3455
```

<210> SEQ ID NO 66
<211> LENGTH: 1091
<212> TYPE: DNA
<213> ORGANISM: Artificial Sequence
<220> FEATURE:
<223> OTHER INFORMATION: Synthetic Construct

<400> SEQUENCE: 66

```
attgtctgag taggtgtcat tctattctgg ggggtggggt ggggcaggac agcaaggggg      60
aggattggga agacaatagc aggcatgctg ggagctaga gtcgaccgga ccggtggaag     120
tcctcttcct cggtgtcctt gacttcaaag ggtctctccc atttgcctgg agagagggga    180
aggtgggcat caccagggt gagtgaaggt ttggaagagt gtagcagaat aagaaaccat     240
gagtcccctc cctgagaagc cctgagcccc cttgacgaca cacatccctc gaggctcagc    300
ttcatcatct gtaaaaggtg ctgaaactga ccatccaagc tgccgaaaaa gattgtgtgg    360
ggataattca aaactagagg aagatgcaga atttctacat cgtggcgatg tcaggctaag    420
agatgccatc gtggctgtgc attttttattg gaatcatatg tttatttgag ggtgtcttgg    480
atattacaaa taaaatgttg gagcatcagg catatttggt accttctgtc taaggctccc    540
tgccccttgt taattggcag ctcagttatt catccagggc aaacattctg cttactattc    600
ctgagagctt tcctcatcct ctagattggc aggggaaatg cagatgcctg agcagcctcc    660
cctctgccat accaacagag cttcaccatc gaggcatgca gagtggacag gggcctcagg    720 gaccccctgat cccagctttc tcattggaca gaaggaggag actggggctg gagagggacc    780
tgggccccca ctaaggccac agcagagcca ggactttagc tgtgctgact gcagcctggc    840
ttgcctccac tgccctcctt tgcctcaaga gcaagggagc ctcagagtgg aggaagcagc    900
ccctggcctt gcctcccacc tcccctcccc tatgctgttt tcctgggaca gtgggagctg    960
gcttagaatg ccctggggcc cccaggaccc tggcatttta accctcagg ggcaggaagg    1020 cagcctgaga tacagaagag tccatcacct gctgtatgcc acacaccatc cccacagtcg    1080
acatttaaat t                                                        1091
```

<210> SEQ ID NO 67
<211> LENGTH: 72
<212> TYPE: DNA
<213> ORGANISM: Artificial Sequence
<220> FEATURE:
<223> OTHER INFORMATION: Synthetic Construct

<400> SEQUENCE: 67

```
ctggaggctt gctgaaggct gtatgctgca ggacacaagg cctgttacta gcactcacat     60
ggaacaaatg gc                                                         72
```

<210> SEQ ID NO 68
<211> LENGTH: 128
<212> TYPE: DNA
<213> ORGANISM: Artificial Sequence

```
<220> FEATURE:
<223> OTHER INFORMATION: Synthetic Construct

<400> SEQUENCE: 68
ctggaggctt gctgaaggct gtatgctgta cgatctaata tcgctcgttt tggccactga      60
ctgacgagcg atatgatcgt acgacaggac acaaggcctg ttactagcac tcacatggaa     120
caaatggc                                                              128

<210> SEQ ID NO 69
<211> LENGTH: 78
<212> TYPE: DNA
<213> ORGANISM: Artificial Sequence
<220> FEATURE:
<223> OTHER INFORMATION: Synthetic Construct

<400> SEQUENCE: 69
cactccctct ctgcgcgctc gctcgctcac tgaggccggg cgaccaaagg tcgcccacgc      60
ccgggctttg cccgggcg                                                    78

<210> SEQ ID NO 70
<211> LENGTH: 145
<212> TYPE: DNA
<213> ORGANISM: Artificial Sequence
<220> FEATURE:
<223> OTHER INFORMATION: Synthetic Construct

<400> SEQUENCE: 70
ttggccactc cctctctgcg cgctcgctcg ctcactgagg ccgcccggc aaagcccggg       60 cgtcgggcga cctttggtcg cccggcctca gtgagcgagc gagcgcgcag agagggagtg    120
gccaactcca tcactagggg ttcct                                          145
```